United States Patent
Ackermann et al.

[11] Patent Number: 6,140,353
[45] Date of Patent: Oct. 31, 2000

[54] N-(4-CARB-AMIMIDOPHENYL) GLYCINEAMIDE DERIVATIVES

[75] Inventors: Jean Ackermann, Riehen; Katrin Gröbke, Basel, both of Switzerland; Yu-Hua Ji, San Mateo, Calif.; Sabine Wallbaum, Lörrach; Lutz Weber, Grenzach-Wyhlen, both of Germany

[73] Assignee: Hoffmann-La Roche Inc., Nutley, N.J.

[21] Appl. No.: 09/204,373

[22] Filed: Dec. 2, 1998

[30] Foreign Application Priority Data

Dec. 4, 1997 [EP] European Pat. Off. .............. 97121285
Nov. 10, 1998 [EP] European Pat. Off. .............. 98121374

[51] Int. Cl.$^7$ ..................... C07C 233/01; C07D 213/02; A61K 31/165; A61K 31/44
[52] U.S. Cl. ........................ 514/357; 514/620; 546/330; 546/332; 546/335; 546/337; 564/164
[58] Field of Search ................................ 546/330, 332, 546/335, 337; 564/164; 514/357, 620

[56] References Cited

FOREIGN PATENT DOCUMENTS 0 739 886   10/1996   European Pat. Off. .
WO 96/37464  11/1996   WIPO .
WO 97/30971   8/1997   WIPO .

OTHER PUBLICATIONS

Weber et al., Angew. Chem. Int. Ed. Engl., 34(20):2280–2282 (1995).
Wu et al., J. Agric Food Chem., 25(4):692–698 (1977).
Burrows et al., J. Am. Chem. Soc., 56:1720–1724 (1934).
Somei et al., Chem. Pharm. Bull., 34(10)4116–4125 (1986).
Kaslow et al., J. Org. Chem., 18:55–58 (1952).
Casiraghi et al., J.C.S. Perkin I, 1862–1865 (1980).
Kompis et al., Eur. J. Med. Chem.—Chimica Therapeutica, 12:531–536 (1977).
Borsche, Ann. Chem., 390:1–29 (1912).

*Primary Examiner*—Zinna Northington Davis
*Attorney, Agent, or Firm*—George W. Johnston; William H. Epstein; John P. Parise

[57] ABSTRACT

N-(4-carbamimidophenylamino) phenylglycineamide derivative compounds having the formula:

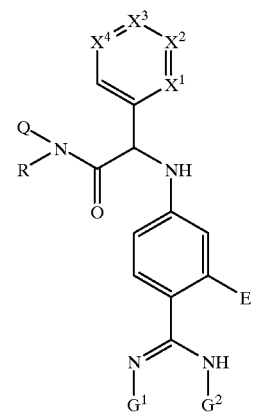

in which E, $g^1$, $g^2$, Q, R and $X^1$ to $X^4$ are each as defined in the description, and hydrates or solvates and physiologically acceptable salts thereof can be used as inhibitors of the formation of the coagulation factors Xa, IXa and thrombin induced by the factor VIIa and by the tissue factor. These compounds can be used as medicaments for the treatment and/or prevention of thromboses, apoplexy, cardiac infarction, inflammation and arteriosclerosis or as antitumor agents.

45 Claims, No Drawings

N-(4-CARB-AMIMIDOPHENYL) GLYCINEAMIDE DERIVATIVES

BACKGROUND OF THE INVENTION

The invention relates the field of N-(4-carbamimidophenyl)glycineamide derivatives. In particular, the invention relates to novel N-(4-carbamimidophenyl) glycineamide derivatives that are useful for inhibiting the coagulation factors Xa, IXa, and thrombin induced by the factor VIIa and the tissue factor. Thus, these novel compounds can inhibit the formation of thrombi and are useful in treating diseases such as thrombisis, apoplexy, cardiac infarction, inflammation and arteriosclerosis.

SUMMARY OF THE INVENTION

The subject invention provides a compound of the formula:

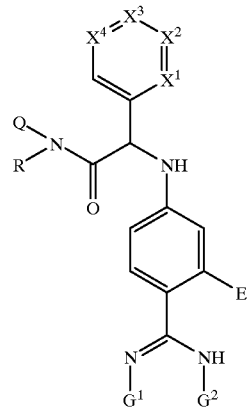

I wherein
- E is hydrogen or OH;
- Q is hydrogen or alkyl;
- R is aryl, cycloalkyl, or alkyl substituted by $R^1$, $R^2$ and $R^3$;
- $R^1$ is hydrogen, COOH, COO-alkyl, or aryl;
- $R^2$ is hydrogen, aryl, cycloalkyl, or heteroaryl;
- $R^3$ is hydrogen, aryl, or (in a position different from the α-position to the nitrogen atom to which the alkyl group R is attached) OH, alkoxy, amino, or protected amino; or
- N(Q,R) is COOH- or COO-alkyl-substituted pyrrolidino, piperidino, or 1,2,3,4-tetrahydroisoquinolin-3-yl;
- three of $X^1$ to $X^4$, independent of one another, are a group $C(R^a)$, $C(R^b)$ or $C(R^c)$, and the fourth is a group $C(R^d)$ or N,
- $R^a$ to $R^d$ independent of one another are H, OH, $NO_2$, dialkylamino, halogen, alkyl, alkoxy, aryloxy, aralkyloxy, heteroarylalkyloxy, heterocyclylalkyloxy, COOH, COO-alkyl, $NHSO_2$-alkyl, $NHSO_2$-aryl, NHCO-alkyl, NHCO-aryl, NHCOO-alkyl, NHCO-alkyl-$NH_2$, NHCO-alkyl-NH—G, aralkyl-CONH, alkyl-O-alkyl-CONH, aryl-O-alkyl-CONH, alkyl-COOH, alkyl-COO-alkyl, O-alkyl-COOH, or O-alkyl-COO-alkyl, or
  - two adjacent groups $R^a$ to $R^d$ together are alkylenedioxy, where not more than three of the groups $R^a$ to $R^d$ shall have the same meaning and $X^1$ shall not be CCOOH or CCOO-alkyl;
- one of $G^1$ and $G^2$ is hydrogen and the other is hydrogen, alkyl, OH, alkoxy, aroyl, alkanoyl-$OCH_2$, aroyl-$OCH_2$ or a group COO—$R^g$ or OCO—$R^g$, where $R^g$ is alkyl or alkyl substituted by halogen, OH, alkoxy, COOH or COO-alkyl; and
- its hydrates or solvates, and physiologically acceptable salts thereof.

Preferred compounds include E, $G^2$ and Q being hydrogen; R being alkyl, aryl, aralkyl, benzhydryl, cycloalkylalkyl, or heteroarylalkyl; $G^1$ being hydrogen, OH, or COO-alkyl; $X^1$ to $X^4$ being a group $C(R^a)$ to $C(R^d)$ and $R^a$ to $R^d$ independent of one another being H, OH, $NO_2$, dialkylamino, halogen, alkyl, alkoxy, aryloxy, aralkyloxy, heteroarylalkyloxy, heterocyclylalkyloxy, COO-alkyl, $NHSO_2$-alkyl, or $NHSO_2$-aryl, where not more than three of $R^a$ to $R^d$ have the same meaning; and $X^1$ is not COO-alkyl. Also preferred are compounds where E, $G^1$, $G^2$ and Q are all hydrogen, and compounds where R is alkyl which is substituted by $R^1$, $R^2$ and $R^3$, and $R^1$ is aryl or COOH, $R^2$ is hydrogen or aryl, and $R^3$ is hydrogen, especially where $R^1$ is phenyl or COOH, $R^2$ is hydrogen or phenyl, and $R^3$ is hydrogen.

$X^1$ to $X^4$ are preferably each a group $C(R^a)$ to $C(R^d)$, with $R^a$ being H, aralkyloxy, $NHSO_2$-aryl, $NHSO_2$-alkyl, aralkyl-CONH, or O-alkyl-COOH; $R^b$ being H or alkoxy; $R^c$ being H, alkoxy or aralkyloxy; and $R^d$ being H or alkoxy. Especially preferred are compounds where $R^a$ is H, carboxybenzyloxy; phenylsulphonylamino; methylsulphonylamino, phenylacetylamino, or carboxymethoxy; $R^b$ is H, methoxy, or ethoxy; $R^c$ is H, methoxy; or benzyloxy; and $R^d$ is H or methoxy.

The subject invention also provides preferred compounds having the formula:

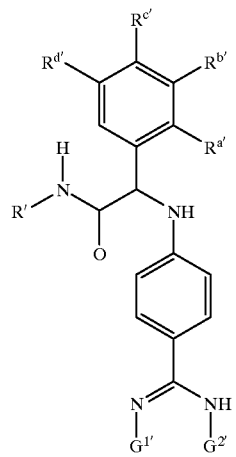

Ia wherein
- R' is $CH_2C_6H_5$, $CH(C_6H_5)COOH$ or $C(C_6H_5)_2COOH$;
- $R^{a'}$ H, carboxybenzyloxy; phenylsulphonylamino; methylsulphonylamino, phenylacetylamino, or carboxymethoxy;
- $R^{b'}$ is H, methoxy, or ethoxy;
- $R^{c'}$ is H, methoxy; or benzyloxy;
- $R^{d'}$ is H or methoxy; and
- one of $G^{1'}$ and $G^{2'}$ is H and the other is H, OH, or $COOCH_3$; and
- its hydrate or solvate, and a physiologically acceptable salt thereof.

In the case of compounds of the formula Ia, it is preferred that $R^{a'}$ is H, phenylsulphonylamino; or methylsulphonylamino, $R^{b'}$ is H or ethoxy, $G^{1'}$ is H or OH, $R^{c'}$ is benzyloxy, and $R^{d'}$ is H, such as (R,S)-N-benzyl-2-(4-benzyloxy-3-ethoxyphenyl)-2-(4-carbamimidoylphenylamino)acetamide and (R,S)-N-benzyl-2-(4-benzyloxy-3-ethoxyphenyl)-2-[4-(N-hydroxycarbamimidoyl)phenylamino]acetamide, or methoxy, such as 2-(2-phenylsulphonylamino-4-benzyloxy-5-methoxyphenyl)-N-benzyl-2-[4-(N-hydroxycarbamimidoyl)phenylamino]acetamide or N-benzyl-2-(4-benzyloxy-2-methanesulphonylamino-5-methoxyphenyl)-2-[4-(N-hydroxycarbamimidoyl)phenylamino]acetamide.

The above compounds can be used in pharmaceutical compositions incorporating an effective amount of the compound and a pharmaceutically acceptable carrier. These compositions can be used in a method of treating or preventing thromboses, apoplexy, cardiac infarction, inflammation and arteriosclerosis, or tumors influenced by the coagulation factors Xa, IXa, or thrombin. The method of treatment or prevention involves administering to a subject in need of such treatment or prevention an effective amount of one or more of the above compounds.

The subject invention also provides a process for manufacturing the above compounds which generates the following unique intermediates having the substituents described above for the subject compounds:

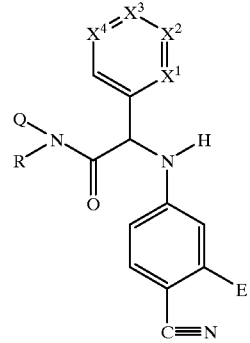

IV

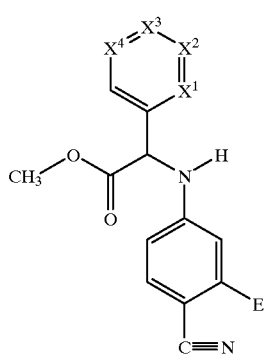

V

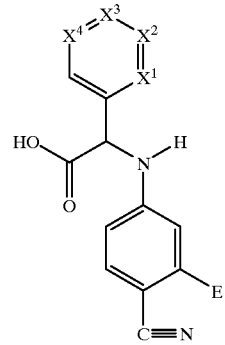

VI

The process for preparing the subject compounds involves:

(a) (i) reacting an aldehyde of the formula:

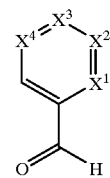

II with an isonitrile of the formula $R^1NC$ and a 4-aminobenzamidine of the formula:

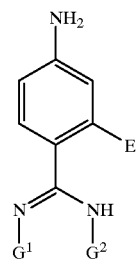

III or
(ii) converting the cyano group contained in a nitrile of the formula:

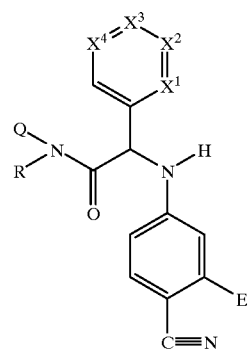

IV into an amidino group $C(N-G^1)NH-G^2$;

(b) in the case of a compound of formula I having a functionally derivatized group, then functionally derivatizing a reactive group of the compound produced in step (a) to yield a compound of formula I having such functionally derivatized group; and (c) in the case of a compound of formula I being a hydrate or solvate, or a physiologically acceptable salt thereof, then hydrating, solvating, or salinating the compound produced in step (a) or (b) to yield the hydrate or solvate, or physiologically acceptable salt thereof, of the compound of formula I.

DETAILED DESCRIPTION OF THE PREFERRED EMBODIMENTS

The subject invention will now be described in terms of its preferred embodiments. These embodiments are set forth to aid in understanding the invention but are not to be construed as limiting.

The invention relates to novel N-(4-carbamimidophenyl) glycineamide derivatives, in particular to those of the formula

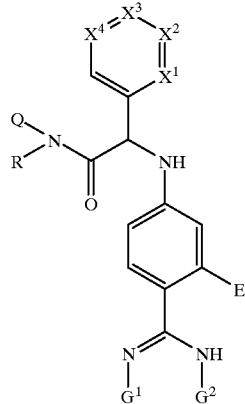

I in which

| | |
|---|---|
| E | is hydrogen or OH, |
| Q | is hydrogen or alkyl, |
| R | is aryl, cycloalkyl or alkyl which is substituted by $R^1$, $R^2$ and $R^3$, |
| $R^1$ | is hydrogen, COOH, COO-alkyl or aryl, |
| $R^2$ | is hydrogen, aryl, cycloalkyl or heteroaryl, |
| $R^3$ | is hydrogen, aryl or (in a position different from the α-position to the nitrogen atom to which the alkyl group R is attached) OH, alkoxy or optionally protected amino, |

N(Q,R) is COOH- or COO-alkyl-substituted pyrrolidino, piperidino or 1,2,3,4-tetrahydroisoquinolin-3-yl, three of the radicals $X^1$ to $X^4$ independently of one another are a group $C(R^a)$, $C(R^b)$ or $C(R^c)$ and the fourth radical is a group $C(R^d)$ or N, $R^a$ to $R^d$ independently of one another are H, OH, $NO_2$, dialkylamino, halogen, alkyl, alkoxy, aryloxy, aralkyloxy, heteroarylalkyloxy, heterocyclylalkyloxy, COOH, COO-alkyl, $NH-SO_2$-alkyl, $NHSO_2$-aryl, NHCO-alkyl, NHCO-aryl, NHCOO-alkyl, NHCO-alkyl-$NH_2$, NHCO-alkyl-NH—G, aralkyl-CONH, alkyl-O-alkyl-CONH, aryl-O-alkyl-CONH, alkyl-COOH, alkyl-COO-alkyl, O-alkyl-COOH or O-alkyl-COO-alkyl, or two adjacent groups $R^a$ to $R^d$ together are alkylenedioxy, where not more than three of the radicals $R^a$ to $R^d$ shall have the same meaning and $X^1$ shall not be CCOOH or CCOO-alkyl, G is an amino protective group and one of the radicals $G^1$ and $G^2$ is hydrogen and the other radical is hydrogen, alkyl, OH, alkoxy, aroyl, alkanoyl-$OCH_2$, aroyl-$OCH_2$ or a group COO—$R^g$ or OCO—$R^g$, $R^g$ is optionally halogen-, OH-, alkoxy-, COOH- or COO-alkyl-substituted alkyl, and hydrates or solvates and physiologically acceptable salts thereof.

Furthermore, the invention relates to processes for preparing the above compounds, to pharmaceutical preparations comprising such compounds, and to the use of these compounds in the preparation of pharmaceutical preparations.

Examples of physiologically acceptable salts of these compounds of the formula I are salts with physiologically tolerable mineral acids, such as hydrochloric acid, sulphuric acid, sulphurous acid or phosphoric acid; or with organic acids, such as methanesulphonic acid, p-toluenesulphonic acid, acetic acid, trifluoroacetic acid, citric acid, fumaric acid, maleic acid, tartaric acid, succinic acid or salicylic acid.

The compounds of the formula I can be solvated, in particular hydrated.

Hydration can occur during the preparation process or slowly as a consequence of hygroscopic properties of an initially anhydrous compound of the formula I.

The compounds of the formula I contain at least one asymmetric carbon atom and can therefore be present as a mixture of enantiomers or as optically pure compounds.

In the context of the present invention, "alkyl", on its own or in combination, such as in COO-alkyl, alkoxy, dialkylamino, aralkyloxy, heteroarylalkyloxy, heterocyclylalkyloxy, $NHSO_2$-alkyl, NHCO-alkyl, aralkyl-CONH, alkyl-O-alkyl-CONH, alkyl-COOH, CCOO-alkyl, alkanoyl and the like, denotes a straight-chain or branched group containing from 1 to 6, preferably 1 to 4, carbon atoms. Examples include methyl, ethyl and butyl.

"Aryl", on its own or in combination, such as in aryloxy, aralkyl, $NHSO_2$-aryl, NHCO-aryl, aralkyl-CONH, aryl-O-alkyl-CONH, aroyl and the like, denotes groups such as phenyl or naphthyl which can be substituted, for example by halogen (e.g. bromine, fluorine or chlorine); alkoxy (e.g. methoxy, ethoxy or propoxy); alkylenedioxy (e.g. methylenedioxy); hydroxyl, nitro, amino, amidino, sulphamoyl, phenyl, phenoxy, COOH or COO-alkyl (e.g. $COOCH_3$ or $COOC_2H_5$). Examples of aryl groups include phenyl and amidinophenyl, of aralkyl groups: benzyl, phenethyl, naphthylmethyl, mono- or dimethoxybenzyl, aminobenzyl or nitrobenzyl, of aryloxy groups: phenoxy or methoxycarbonylphenoxy, of aralkyloxy groups: benzyloxy, nitrobenzyloxy, bromobenzyloxy, dichlorobenzyloxy, methoxybenzyloxy, phenoxybenzyloxy, phenethoxy or biphenylylmethoxy.

"Cycloalkylalkyl" denotes saturated groups having 3 to 7 carbon atoms which are attached via an alkyl group (e.g. cyclopropylmethyl).

"Heteroarylalkyl", on its own or in "heteroarylalkoxy", denotes a 5- to 10-membered aromatic group that is attached via the alkyl or alkoxy group, respectively, and which consists of one or two rings and contains one or more nitrogen atoms. Examples of heteroarylalkyl include imidazolylethyl and indolylethyl. Examples of heteroarylalkoxy include pyridinylmethoxy, indolylmethoxy, quinolylmethoxy, and isoquinolylmethoxy.

"Heterocyclylalkoxy" denotes a 5- to 10-membered saturated or unsaturated non-aromatic group which is attached via an alkoxy group and comprises one or two rings and contains one or more heteroatoms selected from the group consisting of N, O and S. Examples of these are morpholinylethoxy, thiomorpholinylethoxy and tetrahydroquinolylmethoxy. Examples of the groups COO-alkyl, $NHSO_2$-alkyl and $NHSO_2$-aryl are $COOCH_3$, $NHSO_2CH_3$ and $NHSO_2C_6H_5$, respectively. An example of an alkylenedioxy group is methylenedioxy.

Preferred compounds of formula I are those in which $R^1$ is aryl, in particular phenyl or amidino-phenyl; aralkyl, in particular benzyl, phenethyl, naphthylmethyl, mono- or dimethoxybenzyl, aminobenzyl or nitrobenzyl; benzhydryl; cycloalkylalkyl, in particular cyclopropylmethyl; or heteroarylalkyl, in particular imidazolylethyl or indolylethyl.

Preferred compounds of the formula I are furthermore those in which Q is hydrogen or methyl, and/or in which R is aryl, such as phenyl, amidinophenyl or carboxyphenyl, or in which R is alkyl which is substituted by $R^1$, $R^2$ and $R^3$ and in which $R^1$ is a group COOH or COO-alkyl, $R^2$ is aryl or H, and $R^3$ is aryl, H, amino or protected amino, or in which $R^1$ is H, $R^2$ is aryl or heteroaryl and $R^3$ is H or OH.

Preferred $R^1$-, $R^2$- and $R^3$-substituted alkyl groups R are methyl, ethyl, propyl and isopropyl.

Preferred aryl groups R, $R^1$, $R^2$ or $R^3$ are phenyl groups which are substituted by COOH or COO-alkyl, such as $COOCH_3$ or $COOC_2H_5$; $NO_2$, $NH_2$, $SO_2NH_2$ or by one or two groups OH or alkoxy, such as $OCH_3$ or $OC_2H_5$.

Preferred cycloalkyl groups R or $R^2$ are optionally COOH- or COO-alkyl-substituted cyclopentyl groups.

Preferred heteroaryl groups $R^2$ are imidazolyl, indolyl and pyridinyl.

Preferred COO-alkyl groups $R^1$ are $COOCH_3$ and $COOC_2H_5$.

A preferred protected amino group $R^3$ is NH-Boc (t-butoxycarbonylamino).

Preferred compounds of the formula I are furthermore those in which one of the radicals $g^1$ or $g^2$ is a group OH or COO-alkyl, such as $COOCH_3$ or $COOC_2H_5$.

Preferred compounds of the formula I are furthermore those in which $X^1$ is a group $C(R^a)$ in which $R^a$ is H, OH, $NO_2$, halogen, in particular fluorine; alkoxy, in particular methoxy; $NHSO_2$-alkyl or $NHSO_2$-aryl, in particular methanesulphonylamino or phenylsulphonylamino and/or in which $X^2$ is a group $C(R^b)$ in which $R^b$ is H, OH, $NO_2$, alkyl, in particular methyl; alkoxy, in particular methoxy, ethoxy or butoxy; aryloxy, in particular phenoxy; aralkyloxy, in particular benzyloxy, and/or in which $X^3$ is a group $C(R^c)$ in which $R^c$ is H, OH, $NO_2$, dialkylamino, in particular dimethylamino; halogen, in particular bromine; alkyl, in particular methyl; alkoxy, in particular methoxy, ethoxy or propoxy; aryloxy, in particular methoxycarbonylphenoxy; aralkyloxy, in particular benzyloxy, nitrobenzyloxy, bromobenzyloxy, dichlorobenzyloxy, methoxybenzyloxy, phenoxybenzyloxy, phenethoxy or biphenylylmethoxy; heteroarylalkyloxy, in particular pyridinylmethoxy, indolylmethoxy, quinolylmethoxy or isoquinolylmethoxy; or heterocyclylalkyloxy, in particular morpholinylethoxy, thiomorpholinylethoxy or tetrahydroquinolinylmethoxy, or in which $R^b$ and $R^c$ together form an alkylenedioxy group, in particular the methylenedioxy group, and/or in which $X^4$ is a group $C(R^d)$ in which $R^d$ is H, $NO_2$, alkoxy, in particular methoxy; or aralkoxy, in particular benzyloxy.

Preferred compounds of the formula I are those in which $X^1$ to $X^4$, independent of one another, are a group $C(R^a)$ to $C(R^d)$ in which $R^a$ to $R^d$ are NHCO-alkyl, such as NH-acetyl, NHCO-aryl, such as NH-benzoyl, NHCOO-alkyl, such as $NHCOOCH_3$, NHCO-alkyl-(optionally protected amino), such as $NHCOCH_2NH_2$, $NHCOCH_2CH_2NH_2$ and $NHCOCH_2NH$-Boc; aralkyl-CONH, such as benzyl-CONH, alkyl-O-alkyl-CONH, such as $CH_3OCH_2CONH$, alkyl-COOH, such as $CH_2CH_2COOH$, O-alkyl-COOH, such as $O(CH_2)_{1\ or\ 3}COOH$ and $OCH(CH_3)$ COOH, aryloxy, such as $OC_6H_4COOH$ and aralkyloxy, such as $OCH_2C_6H_4COOH$, where instead of a group COOH a group COO-alkyl, such as $COO(CH_3$ or $C_2H_5)$ may be present.

Preferred compounds of formula I are furthermore those in which one of the radicals $X^1$ to $X^4$ is a nitrogen atom and the other three independently of one another are a group $C(R^a)$, $C(R^b)$ or $C(R^c)$, in particular in which one group of $R^a$, $R^b$ and $R^c$ denotes H and the other two denote lower alkoxy, such as methoxy or ethoxy.

Preferred compounds of formula I are furthermore those in which one of the groups $g^1$ and $g^2$ is hydrogen and the other group is aroyl, in particular optionally halogen-substituted benzoyl, such as fluorobenzoyl, alkyl-$COOCH_2$-benzoyl or phenyl-$COOCH_2$-benzoyl, or is haloalkyl-OCO, such as trichloroethyl-OCO.

Preference is given to the compounds in which E, $g^1$, $g^2$ and Q are each hydrogen, and/or in which R is $R^1$-, $R^2$- and $R^3$-substituted alkyl, in particular methyl or ethyl, in particular where $R^1$ is aryl, specifically phenyl, or COOH, $R^2$ is hydrogen or aryl, specifically phenyl, and $R^3$ is hydrogen, and/or in which $X^1$ to $X^4$ are a group $C(R^a)$ to $C(R^d)$, in particular a group in which $R^a$ is H, aralkyloxy, specifically carboxybenzyloxy; $NHSO_2$-aryl, specifically phenylsulphonylamino; aralkyl-CONH, specifically phenylacetylamino, or O-alkyl-COOH, specifically carboxymethoxy, $R^b$ is H or alkoxy, specifically methoxy or ethoxy, $R^c$ is H, alkoxy, specifically methoxy, or aralkyloxy, specifically benzyloxy, and $R^d$ is H or alkoxy, specifically methoxy.

Examples of such compounds are:

(R,S)-N-benzyl-2-(4-benzyloxy-3-ethoxyphenyl)-2-(4-carbamimidoylphenylamino)acetamide, 2-(2-phenylsulphonylamino-4-benzyloxy-5-methoxyphenyl)-N-benzyl-2-(4-carbamimidoylphenylamino)acetamide and furthermore (RS)-[2-(4-benzyloxy-3-methoxyphenyl)-2-(4-carbamimidoylphenylamino)acetylamino] diphenylacetic acid, (RS)- and (SR)-3-[(RS)-2-(4-benzyloxy-3-methoxyphenyl)-2-(4-carbamimidoylphenylamino) acetylamino]-3-phenyl-propionic acid, (S)-[(R)-2-(4-benzyloxy-3-methoxyphenyl)-2-(4-carbamimidoylphenylamino)acetylamino]phenylacetic acid, (S)-[(S)-2-(4-carbamimidoylphenylamino)-2-(3,5-dimethoxyphenyl)acetylamino]phenylacetic acid, (RS)-3-[2-[benzylcarbamoyl-(4-carbamimidoylphenylamino)methyl]-4,5-dimethoxyphenoxymethyl]benzoic acid, (RS)-[2-[benzylcarbamoyl-(4-carbamimidoylphenylamino)-methyl]-4,5-dimethoxyphenoxy]acetic acid, (S)-[(R)-2-(2-phenylsulphonylamino-4-benzyloxy-5-methoxyphenyl)-2-(4-carbamimidoylphenylamino) acetylamino]-phenylacetic acid, (S)-[(S)-2-(2-phenylsulphonylamino-4-benzyloxy-5-methoxyphenyl)-2-(4-carbamimidoylphenylamino)acetylamino]-phenylacetic acid, (S)-[(R)-2-(4-benzyloxy-5-methoxy-2-phenylacetylaminophenyl)-2-(4-carbamimidoylphenylamino)acetylamino]-phenylacetic acid, (S)-[(S)-2-(4-benzyloxy-5-methoxy-2-phenylacetylaminophenyl)-2-(4-carbamimidoylphenylamino)acetylamino]phenylacetic acid.

Further examples of compounds of the formula I are the compounds below:

(S)-2-[(R)-2-(4-benzyloxy-3-methoxyphenyl)-2-(4-carbamimidoylphenylamino)acetylamino]propionic acid, (S)-2-[(S)-2-(4-benzyloxy-3-methoxyphenyl)-2-(4-carbamimidoylphenylamino)acetylamino]propionic acid, (S)-2-[(R)-2-(4-benzyloxy-3-methoxyphenyl)-2-(4-carbamimidoylphenylamino)acetylamino]-3-phenylpropionic acid, (S)-2-[(S)-2-(4-benzyloxy-3-methoxyphenyl)-2-(4-carbamimidoylphenylamino)acetylamino]-3-phenylpropionic acid, (S)-2-[(R)-2-(4-benzyloxy-3-methoxyphenyl)-2-(4-carbamimidoylphenylamino)acetylamino]-3-(4-hydroxyphenyl)-propionic acid, (S)-2-[(S)-2-(4-benzyloxy-3-methoxyphenyl)-2-(4-carbamimidoylphenylamino)acetylamino]-3-(4-hydroxyphenyl)-propionic acid, (S)-1-[(R)- and -[(S)-(4-benzyloxy-3-methoxyphenyl)-(4-carbamimidoylphenylamino)acetyl]pyrrolidine-2-carboxylic acid, (RS)-2-[2-(4-benzyloxy-3-methoxyphenyl)-2-(4-carbamimidoyl)phenylamino)acetylamino]-2-methylpropionic acid, (S)-[[(R)-(4-benzyloxy-3-methoxyphenyl)-(4-carbamimidoylphenylamino)acetyl]methylamino]phenylacetic acid, (S)-[[(S)-(4-benzyloxy-3-methoxyphenyl)-(4-carbamimidoylphenylamino)acetyl]methylamino]phenylacetic acid, (RS)- and (SR)-1-[(RS)-(4-benzyloxy-3-methoxyphenyl)-(4-carbamimidoylphenylamino)acetyl]pyrrolidine-3-carboxylic acid, (RS)- or (SR)-2-[(RS)-(4-benzyloxy-3-methoxyphenyl)-(4-carbamimidoylphenylamino)acetyl]-1,2,3,4-tetrahydroisoquinoline-3-carboxylic acid, (RS)-1-[2-(4-benzyloxy-3-methoxyphenyl)-2-(4-carbamimidoylphenylamino)acetylamino]cyclopentanecarboxylic acid, (S)-2-[(R)-2-(4-benzyloxy-3-methoxyphenyl)-2-(4-carbamimidoylphenylamino)acetylamino]-4-tert-butoxycarbonylaminobutyric acid, (S)-2-[(S)-2-(4-benzyloxy-3-methoxyphenyl)-2-(4-carbamimidoylphenylamino)acetylamino]-4-tert-butoxycarbonylaminobutyric acid, (S)-2-[(R)-2-(4-benzyloxy-3-methoxyphenyl)-2-(4-carbamimidoylphenylamino)acetylamino]-3-tert-butoxycarbonylaminopropionic acid, (S)-2-[(S)-2-(4-benzyloxy-3-methoxyphenyl)-2-(4-carbamimidoylphenylamino)acetylamino]-3-tert-butoxycarbonylaminopropionic acid, (RS)-2-[2-(4-benzyloxy-3-methoxyphenyl)-2-(4-carbamimidoylphenylamino)acetylamino]benzoic acid, (RS)-3-[2-(4-benzyloxy-3-methoxyphenyl)-2-(4-carbamimidoylphenylamino)acetylamino]benzoic acid, (RS)-4-[2-(4-benzyloxy-3-methoxyphenyl)-2-(4-carbamimidoylphenylamino)acetylamino]benzoic acid, (E)- and/or (Z)-(S)-2-[(R)- and -[(S)-2-(4-benzyloxy-3-methoxyphenyl)-2-[4-(N-hydroxycarbamimidoyl)phenylamino]acetylamino]-propionic acid, (E)- and/or (Z)-(S)-2-[(R)-2-(4-benzyloxy-3-methoxyphenyl)-2-[4-(N-hydroxycarbamimidoyl)phenylamino]acetylamino]-3-phenylpropionic acid, (E)- and/or (Z)-(S)-2-[(S)-2-(4-benzyloxy-3-methoxyphenyl)-2-[4-(N-hydroxycarbamimidoyl)phenylamino]acetylamino]-3-phenylpropionic acid, (E)- and/or (Z)-(S)-2-[(R)- and -[(S)-2-(4-benzyloxy-3-methoxyphenyl)-2-[4-(N-hydroxycarbamimidoyl)phenylamino]acetylamino]-3-(4-hydroxyphenylpropionic acid, (E)- and/or (Z)-(S)-1-[(R)- and -[(S)-(4-benzyloxy-3-methoxyphenyl)-[4-(N-hydroxycarbamimidoyl)phenylamino]acetyl]pyrrolidine-2-carboxylic acid, (E)- and/or (Z)-(RS)-2-[2-(4-benzyloxy-3-methoxyphenyl)-2-[4-(N-hydroxycarbamimidoyl)phenylamino]acetylamino]-2-methylpropionic acid, (E)- and/or (Z)-(S)[[(R)- and -[[(S)-(4-benzyloxy-3-methoxyphenyl)-[4-(N-hydroxycarbamimidoyl)phenylamino]acetyl]methyiamino]phenylacetic acid, (E)- and/or (Z)-(RS)- and -(SR)-1-[(RS)-(4-benzyloxy-3-methoxyphenyl)-[4-(N-hydroxycarbamimidoyl)phenylamino]acetyl]pyrrolidine-3-carboxylic acid, (E)- and/or (Z)-(RS)- and -(SR)-2-[(RS)-(4-benzyloxy-3-methoxyphenyl)-[4-(N-hydroxycarbamimidoyl)phenylamino]acetyl]-1,2,3,4-tetrahydroisoquinoline-3-carboxylic acid, (E)- and/or (Z)-(RS)-1-[2-(4-benzyloxy-3-methoxyphenyl)-2-[4-(N-hydroxycarbamimidoyl)phenylamino]-acetylamino]cyclopentanecarboxylic acid, (E)- and/or (Z)-(RS)-[2-(4-benzyloxy-3-methoxyphenyl)-2-[4-(N-hydroxycarbamimidoyl)phenylamino]acetylamino]diphenylacetic acid, (S)-2-[(R)- and -[(S)-2-(4-benzyloxy-3-methoxyphenyl)-2-[4-[(E)- and/or -[(Z)-N-hydroxycarbamimidoyl]phenylamino]acetylamino]-4-tert-butoxycarbonylaminobutyric acid, (S)-2-[(R)- and -[(S)-2-(4-benzyloxy-3-methoxyphenyl)-2-[4-[(E)- and/or -[(Z)-N-hydroxycarbamimidoyl]phenylamino]acetylamino]- 3-tert-butoxycarbonylaminopropionic acid, (E)- and/or (Z)-(RS)-3-(2-(4-benzyloxy-3-methoxyphenyl)-2-[4-(N-hydroxycarbamimidoyl)phenylamino]-acetylamino]-3-tert-butoxycarbonylaminopropionic acid, (E)- and/or (Z)-(RS)-4-[2-(4-benzyloxy-3-methoxyphenyl)-2-[4-(N-hydroxycarbamimidoyl)phenylamino]-acetylamino]benzoic acid, (E)- and/or (Z)-(RS)- and -(SR)-3-[(RS)-2-(4-benzyloxy-3-methoxyphenyl)-2-[4-(N-hydroxycarbamimidoyl)phenylamino]acetylamino]-3-phenylpropionic acid, (S)-4-amino-2-[(R)- and -[(S)-2-(4-benzyloxy-3-methoxyphenyl)-2-(4-carbamimidoylphenylamino)acetylamino]butyric acid, (S)-3-amino-2-[(R)- and -[(S)-2-(4-benzyloxy-3-methoxyphenyl)-2-(4-carbamimidoylphenylamino)acetylamino]propionic acid, (E)- and/or (Z)-(S)[(R)- or -[(S)-2-(4-benzyloxy-3-methoxyphenyl)-2-[4-(N-hydroxycarbamimidoyl)phenylamino]acetylamino-phenylacetic acid, (S)[(S)-2-(4-benzyloxy-3-methoxyphenyl)-2-(4-carbamimidoylphenylamino)acetylamino]phenylacetic acid, (R)[(R)-2-(4-benzyloxy-3-methoxyphenyl)-2-(4-carbamimidoylphenylamino)acetylamino]phenylacetic acid, (R)[(S)-2-(4-benzyloxy-3-methoxyphenyl)-2-(4-carbamimidoylphenylamino)acetylamino]phenylacetic acid, ethyl (E)- and/or (Z)-(S)-3-(4-aminophenyl)-2-[(R)- and -[(S)-2-(4-benzyloxy-3-methoxyphenyl)-2-[4-(N-hydroxycarbamimidoyl)phenylamino]acetylamino]propionate, ethyl (S)-3-(4-aminophenyl)-2-[(R)- and -[(S)-2-(4-benzyloxy-3-methoxyphenyl)-2-(4-carbamimidoylphenylamino)acetylamino]propionate, (S)-3-(4-aminophenyl)-2-[(R)-2-(4-benzyloxy-3-methoxyphenyl)-2-(4-carbamimidoylphenylamino)acetylamino]propionic acid, (S)-3-(4-aminophenyl)-2-[(S)-2-(4-benzyloxy-3-methoxyphenyl)-2-(4-carbamimidoylphenylamino)acetylamino]propionic acid, (S)-[(R)-2-(4-carbamimidoylphenylamino)-2-(3,5-dimethoxyphenyl)acetylamino]phenylacetic acid, (RS)-2-(4-benzyloxy-3-methoxyphenyl)-2-(4-carbamimidoylphenylamino)-N-[2-(3,4-dihydroxyphenyl)ethyl]acetamide, (RS)-N-benzyl-2-(4-benzyloxy-3-methoxyphenyl)-2-(4-carbamimidoylphenylamino)-N-methylacetamide, (RS)-2-(4-benzyloxy-3-methoxyphenyl)-2-(4-carbamimidoylphenylamino)-N-[2-(4-sulphamoylphenyl)ethyl]acetamide, (RS)-2-(4-benzyloxy-3-methoxyphenyl)-2-(4-carbamimidoylphenylamino)-N-(2-pyridin-2-ylethyl)acetamide, (RS)-N-[2-(4-aminophenyl)ethyl]-2-(4-benzyloxy-3-methoxyphenyl)-2-(4-carbamimidoylphenylamino)acetamide, (R)-2-(4-benzyloxy-3-methoxyphenyl)-2-(4-carbamimidoylphenylamino)-N-[(R)-2-hydroxy-1-phenylethyl]acetamide, (S)-2-(4-benzyloxy-3-methoxyphenyl)-2-(4-carbamimidoylphenylamino)-N-[(R)- 2-hydroxy-1-phenylethyl]acetamide, (R)-2-(4-benzyloxy-3-methoxyphenyl)-2-(4-carbamimidoylphenylamino)-N-[(S)- 2-hydroxy-1-phenylethyl]acetamide, (S)-2-(4-benzyloxy-3-methoxyphenyl)-2-(4-carbamimidoylphenylamino)-N-[(S)-2-hydroxy-1-phenylethyl]acetamide, (R)-2-(4-benzyloxy-3-methoxyphenyl)-2-(4-carbamimidoylphenylamino)-N-[(R)-1-phenylethyl]acetamide, (S)-2-(4-benzyloxy-3-methoxyphenyl)-2-(4-carbamimidoylphenylamino)-N-[(R)-1-phenylethyl]acetamide, (R)-2-(4-benzyloxy-3-methoxyphenyl)-2-(4-carbamimidoylphenylamino)-N-[(S)-1-phenylethyl]acetamide, (S)-2-(4-benzyloxy-3-methoxyphenyl)-2-(4-carbamimidoylphenylamino)-N-[(S)-1-phenylethyl]acetamide, (E)- and/or (Z)-(RS)-N-benzyl-2-(4-benzyloxy-3-methoxyphenyl)-2-[4-(N-hydroxycarbamimidoyl)phenylamino]-N-methylacetamide, E)- and/or (Z)-(RS)-2-(4-benzyloxy-3-methoxyphenyl)-2-[4-(N-hydroxycarbamimidoyl)phenylamino]-N-[2-(4-sulphamoylphenyl)ethyl]acetamide, (E)- and/or (Z)-(RS)-2-(4-benzyloxy-3-methoxyphenyl)-2-[4-(N-hydroxycarbamimidoyl)phenylamino]-N-(2-pyridin-2-ylethyl)acetamide, (E)- and/or (Z)-(RS)-2-(4-benzyloxy-3-methoxyphenyl)-2-[4-(N-hydroxycarbamimidoyl)phenylamino]-N-[2-(4-nitrophenyl)ethyl]acetamide, (E)- and/or (Z)-(R)-2-(4-benzyloxy-3-methoxyphenyl)-2-[4-(N-hydroxycarbamimidoyl)phenylamino]-N-[(R)-(2-hydroxy-1-phenylethyl]acetamide, (E)- and/or (Z)-(S)-2-(4-benzyloxy-3-methoxyphenyl)-2-[4-(N-hydroxycarbamimidoyl)phenylamino]-N-(R)-(2-hydroxy-1-phenylethyl]acetamide, (E)- and/or (Z)-(R)-2-(4-benzyloxy-3-methoxyphenyl)-2-[4-(N-hydroxycarbamimidoyl)phenylamino]-N-[(S)-2-hydroxy-1-phenylethyl]acetamide, (E)- and/or (Z)-(S)-2-(4-benzyloxy-3-methoxyphenyl)-2-[4-(N-hydroxycarbamimidoyl)phenylamino]-N-[(S)-2-hydroxy-1-phenylethyl]acetamide, (E)- and/or (Z)-(R)-2-(4-benzyloxy-3-methoxyphenyl)-2-[4-(N-hydroxycarbamimidoyl)phenylamino]-N-[(R)-1-phenylethyl]acetamide, (E)- and/or (Z)-(S)-2-(4-benzyloxy-3-methoxyphenyl)-2-[4-(N-hydroxycarbamimidoyl)phenylamino]-N-[(R)-1-phenylethyl]acetamide, (E)- and/or (Z)-(R)-2-(4-benzyloxy-3-methoxyphenyl)-2-[4-(N-hydroxycarbamimidoyl)phenylamino]-N-[(S)-1-phenylethyl]acetamide, (E)- and/or (Z)-(S)-2-(4-benzyloxy-3-methoxyphenyl)-2-[4-(N-hydroxycarbamimidoyl)phenylamino]-N-[(S)-1-phenylethyl]acetamide, (RS)-N-[2-(benzylcarbamoyl-(4-carbamimidoylphenylamino)methyl]-5-benzyloxy-4-methoxyphenyl]benzamide acetate, methyl (RS)-[2-[benzylcarbamoyl-(4-carbamimidoylphenylamino)methyl]-5-benzyloxy-4-methoxyphenyl]carbamate acetate, (RS)-2-(2-acetylamino-4-benzyloxy-5-methoxyphenyl)-N-benzyl-2-(4-carbamimidoylphenylamino)acetamide, (RS)-N-benzyl-2-(4-benzyloxy-5-methoxy-2-phenylacetylaminophenyl)-2-(4-carbamimidoylphenylamino)acetamide, (RS)-N-benzyl-2-(4-carbamimidoylphenylamino)-2-(4,5-dimethoxy-2-phenylacetylaminophenyl)acetamide, methyl (RS)-[2-[benzylcarbamoyl-(4-carbamimidoylphenylamino)methyl]-4,5-dimethoxyphenyl]carbamate, (RS)-N-[2-[benzylcarbamoyl-(4-carbamimidoylphenylamino)methyl]-4,5-dimethoxyphenyl]benzamide, (RS)-N-[2-[benzylcarbamoyl-(4-carbamimidoylphenylamino)methyl]-4-methoxyphenyl]benzamide, (RS)-2-(2-benzenesulphonylamino-5-methoxyphenyl)-N-benzyl-2-(4-carbamimidoylphenylamino)acetamide, (RS)-N-(2-[benzylcarbamoyl-[4-(N-hydroxycarbamimidoyl)phenylamino]methyl]-5-benzyloxy-4-methoxyphenyl)benzamide, methyl (RS)-(2-[benzylcarbamoyl-[4-(N-hydroxycarbamimidoyl)phenylamino]methyl]-5-benzyloxy-4-methoxyphenyl)carbamate, (E)- and/or (Z)-(RS)-2-(2-acetylamino-4-benzyloxy-5-methoxyphenyl)-N-benzyl-2-[4-(N-hydroxycarbamimidoyl)phenylamino]acetamide, (E)- and/or (Z)-(RS)-N-benzyl-2-(4-benzyloxy-5-methoxy-2-phenylacetylaminophenyl)-2-[4-(N-hydroxycarbamimidoyl)phenylamino]acetamide, (E)- and/or (Z)-(RS)-N-benzyl-2-(4,5-dimethoxy-2-phenylacetylaminophenyl)-2-[4-(N-hydroxycarbamimidoyl)phenylamino]acetamide, methyl (E)- and/or (Z)-(RS)-[2-[benzylcarbamoyl-[4-(N-hydroxycarbamimidoyl)phenylamino]methyl]-4,5-dimethoxyphenyl]carbamate, (E)- and/or (Z)-(RS)-N-[2-[benzylcarbamoyl-[4-(N-hydroxycarbamimidoyl)phenylamino]methyl]-4,5-dimethoxyphenyl]benzamide, (E)- and/or (Z)-(RS)-N-[2-[benzylcarbamoyl-[4-(N-hydroxycarbamimidoyl)phenylamino]methyl]-4-methoxyphenyl]benzamide, (E)- and/or (Z)-(RS)-2-(2-phenylsulphonylamino-5-methoxyphenyl)-N-benzyl-2-[4-(N-hydroxycarbamimidoyl)phenylamino]acetamide, (RS)-N-benzyl-2-[4-benzyloxy-5-methoxy-2-(2-methoxyacetylamino)phenyl]-2-[4-(N-hydroxycarbamimidoyl)phenylamino]acetamide, (RS)-N-benzyl-2-[4-benzyloxy-5-methoxy-2-(2-methoxyacetylamino)phenyl]-2-(4-carbamimidoylphenylamino)acetamide, tert-butyl (RS)-[(2-[benzylcarbamoyl-[4-(N-hydroxycarbamimidoyl)phenylamino]methyl]-5-benzyloxy-4-methoxyphenylcarbamoyl)methyl]carbamate, (RS)-2-[2-(2-aminoacetylamino)-4-benzyloxy-5-methoxyphenyl]-N-benzyl-2-(4-carbamimidoylphenylamino)acetamide, (RS)-4-[2-[benzylcarbamoyl-(4-carbamimidoylphenylamino)methyl]-4,5-dimethoxyphenoxymethyl]benzoic acid, (RS)-4-[2-[benzylcarbamoyl-(4-carbamimidoylphenylamino)methyl]-4,5-dimethoxyphenoxy]butyric acid, (RS)-[2-[benzylcarbamoyl-(4-carbamimidoylphenylamino)methyl]-4-methoxyphenoxy]acetic acid, (RS)-[2-[benzylcarbamoyl-(4-carbamimidoylphenylamino)methyl]-4,6-dimethylphenoxy]acetic acid, (E)- and/or (Z)-(RS)-3-[2-[benzylcarbamoyl-[4-(N-hydroxycarbamimidoyl)phenylamino]methyl]-4,5-dimethoxyphenoxymethyl]benzoic acid, (E)- and/or (Z)-(RS)-[2-[benzylcarbamoyl-[4-(N-hydroxycarbamimidoyl)phenylamino]methyl]-4,5-dimethoxyphenoxy]acetic acid, (E)- and/or (Z)-(RS)-4-[2-[benzylcarbamoyl-[4-(N-hydroxycarbamimidoyl)phenylamino]methyl]-4,5-dimethoxyphenoxymethyl]benzoic acid, (E)- and/or (Z)-(RS)-4-[2-[benzylcarbamoyl-[4-(N-hydroxycarbamimidoyl)phenylamino]methyl]-4,5-dimethoxyphenoxy]butyric acid, (E)- and/or (Z)-(RS)-[2-[benzylcarbamoyl-[4-(N-hydroxycarbamimidoyl)phenylamino]methyl]-4-methoxyphenoxy]acetic acid, (E)- and/or (Z)-(RS)[2-[benzylcarbamoyl-[4-(N-hydroxycarbamimidoyl)phenylamino]methyl]-4,6-dimethyl-phenoxy]acetic acid, (E)- and/or (Z)-(R)-2-[2-[(R)-benzylcarbamoyl-[4-(N-hydroxycarbamimidoyl)phenylamino]methyl]-4,5-dimethoxyphenoxy]propionic acid, (E)- and/or (Z)-(R)-2-[2-[(S)-benzylcarbamoyl-[4-(N-hydroxycarbamimidoyl)phenylamino]methyl]-4,5-dimethoxyphenoxy]propionic acid, (R)-2-[2-[(R)-benzylcarbamoyl-(4-carbamimidoylphenylamino)methyl]-4,5-dimethoxyphenoxy]propionic acid, (R)-2-[2-[(S)-benzylcarbamoyl-(4-carbamimidoylphenylamino)methyl]-4,5-dimethoxyphenoxy]propionic acid, (E)- and/or (Z)-(S)-2-[2-[(R)-benzylcarbamoyl-[4-(N-hydroxycarbamimidoyl)phenylamino]methyl]-4,5-dimethoxyphenoxy]propionic acid, (E)- and/or (Z)-(S)-2-[2-[(S)-benzylcarbamoyl-[4-(N-hydroxycarbamimidoyl)phenylamino]methyl]-4,5-dimethoxyphenoxy]propionic acid, (S)-2-[2-[(R)-benzylcarbamoyl-(4-carbamimidoylphenylamino)methyl]-4,5-dimethoxyphenoxy]propionic acid, (S)-2-[2-[(S)-benzylcarbamoyl-(4-carbamimidoylphenylamino)methyl]-4,5-dimethoxyphenoxy]propionic acid, (RS)-3-[4-[benzylcarbamoyl-(4-carbamimidoylphenylamino)methyl]-2-methoxyphenoxy]benzoic acid, (RS)-2-[4-[benzylcarbamoyl-(4-carbamimidoylphenylamino)methyl]-2-methoxyphenoxy]benzoic acid, (RS)-4-[4-[benzylcarbamoyl-(4-carbamimidoylphenylamino)methyl]-2-methoxyphenoxy]benzoic acid, (RS)-3-(4-[benzylcarbamoyl-[4-(N-hydroxycarbamimidoyl)phenylamino]methyl]-2-methoxyphenoxy)benzoic acid, (RS)-4-(4-[benzylcarbamoyl-[4-(N-hydroxycarbamimidoyl)phenylamino]methyl]-2-methoxyphenoxy)benzoic acid, methyl (RS)-5-[benzylcarbamoyl-[4-(N-hydroxycarbamimidoyl)phenylamino]methyl]-2,3-dimethoxybenzoate, methyl (RS)-5-[benzylcarbamoyl-(4-carbamimidoylphenylamino)methyl]-2,3-dimethoxybenzoate, (RS)-5-[benzylcarbamoyl-(4-carbamimidoylphenylamino)methyl]-2,3-dimethoxybenzoic acid, (RS)-2-(4-[benzylcarbamoyl-[4-(N-hydroxycarbamimidoyl)phenylamino]methyl]-2-methoxyphenoxy)benzoic acid, (E)- and/or (Z)-(RS)-3-[2-[benzylcarbamoyl-[4-(N-hydroxycarbamimidoyl)phenylamino]methyl]-4,5-dimethoxyphenyl]propionic acid, (RS)-3-[2-[benzylcarbamoyl-(4-carbamimidoylphenylamino)methyl]-4,5-dimethoxyphenyl]propionic acid, (E)- and/or (Z)-(RS)-2-(3-acetylaminophenyl)-N-benzyl-2-[4-(N-hydroxycarbamimidoyl)phenylamino]acetamide, (RS)-2-(3-acetylaminophenyl)-N-benzyl-2-(4-carbamimidoylphenylamino)acetamide, (RS)-N-benzyl-2-(4-carbamimidoylphenylamino)-2-(3-nitrophenyl)acetamide, (RS)-N-benzyl-2-(4-carbamimidoylphenylamino)-2-(2,6-dimethoxypyridin-4-yl)acetamide, (RS)-N-benzyl-2-(4-carbamimidoylphenylamino)-2-(4,6-dimethoxypyridin-2-yl)acetamide, (RS)-N-benzyl-2-(4-benzyloxy-3,5-dimethylphenyl)-2-(4-carbamimidoylphenylamino)acetamide, (RS)-N-benzyl-2-(3-benzyloxy-5-propoxyphenyl)-2-(4-carbamimidoylphenylamino)acetamide hydrochloride, (RS)-N-benzyl-2-(3,5-bisbenzyloxyphenyl)-2-(4-carbamimidoylphenylamino)acetamide hydrochloride, (RS)-N-benzyl-2-(4-carbamimidoylphenylamino)-2-(2,6-diethoxypyridin-4-yl)acetamide, (RS)-N-benzyl-2-(4-benzyloxy-3-ethoxyphenyl)-2-[3-hydroxy-4-(N-hydroxycarbamimidoyl)phenylamino]acetamide, (RS)-N-benzyl-2-(4-benzyloxy-3-ethoxyphenyl)-2-(4-carbamimidoyl-3-hydroxyphenylamino)acetamide, (S)[(R)- and -[(S)-2-(2-phenylsulphonylamino-4-benzyloxy-5-methoxyphenyl)-2-[4-[(E)- and/or -[(Z)-N-hydroxycarbamimidoyl)phenylamino]acetylamino]phenylacetic acid, (S)[(R)- and -[(S)-2-(4-benzyloxy-5-methoxy-2-phenylacetylaminophenyl)-2-]4-[(E)- and/or -[(Z)-N-hydroxycarbamimidoyl]phenylamino]acetylamino]phenylacetic acid, (S)-[(R)-2-(2-acetylamino-4-benzyloxy-5-methoxyphenyl)-2-(4-carbamimidoylphenylamino)acetylamino]phenylacetic acid acetate, (S)-[(S)-2-(2-acetylamino-4-benzyloxy-5-methoxyphenyl)-2-(4-carbamimidoylphenylamino)acetylamino]phenylacetic acid, (RS)-N-[amino-(4-[[benzylcarbamoyl-(4-benzyloxy-3-ethoxyphenyl)methyl]amino]phenyl)methylene]-4-fluorobenzamide, (RS)-2-[[amino-(4-[[benzylcarbamoyl-(4-benzyloxy-3-ethoxyphenyl)methyl]amino]phenyl)methylene]carbamoyl]benzyl benzoate, 2,2,2-trichloroethyl (RS)-[amino-(4-[[benzylcarbamoyl-(4-benzyloxy-3-ethoxyphenyl)methyl]amino]phenyl)methylene]carbamate, methyl (RS)-[amino-(4-[[benzylcarbamoyl-(4-benzyloxy-3-ethoxyphenyl)methyl]amino]phenyl)methylene]carbamate.

The compounds of the formula I according to the invention can be prepared by a) reacting an aldehyde of the formula

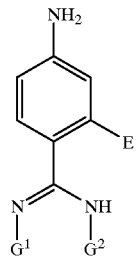

II with an isonitrile of the formula $R^1NC$ and a 4-aminobenzamidine of the formula

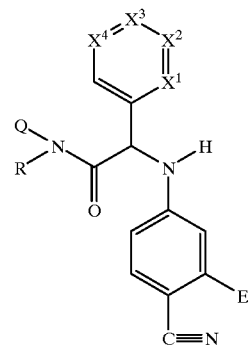

III or b) by converting the cyano group CN contained in an appropriate nitrile of the formula below

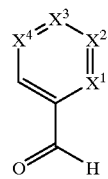

IV into an amidino group $C(N—G^1)NH—G^2$, c) functionally derivatizing, if desired, a reactive group contained in a compound I, and d) converting, if desired, a compound of the formula I into a physiologically acceptable salt or converting a salt of a compound I into the free acid or base.

The reaction of a substituted benzaldehyde of the formula II, an isonitrile of the formula RNC and a 4-aminobenzamidine of the formula III is advantageously carried out in a solvent (e.g. methanol, isopropanol, ethanol, dioxane, or tetrahydrofuran), or in a solvent mixture (e.g. tetrahydrofuran and water or isopropanol and water), advantageously by using an inorganic acid (e.g. hydrochloric acid, sulphuric acid or boron trifluoride etherate), or an organic acid (e.g. toluenesulphonic acid), or in acidic ion exchanger (e.g. Amberlyst K10) as catalyst, at a temperature between 0° C. and 100° C., giving compounds of the formula I. The reaction of a substituted aldehyde of the formula II, of an isonitrile of the formula $R^1NC$ and 4-aminobenzonitrile under similar reaction conditions leads to compounds of the formula IV in which Q is hydrogen.

Compounds of the formula IV are also obtained a) by reaction of an aldehyde of the formula II, the benzylisonitrile and an optionally 2-hydroxylated 4-aminobenzonitrile in anhydrous methanol and boron trifluoride etherate, b) subsequent treatment with water, c) hydrolysis of the resulting compound of the formula

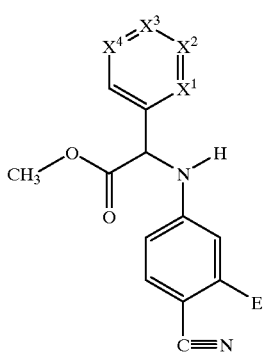

V for example advantageously in THF using lithium hydroxide, and then d) conversion of the resulting acid of the formula

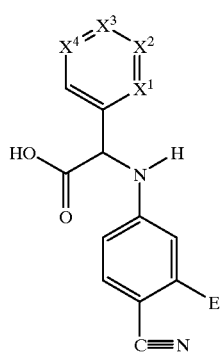

VI into a corresponding nitrile of the formula IV by reaction with an amine of the formula HN(R,Q) in a solvent, such as DMF or dichloromethane, with addition of a coupling reagent, such as benzotriazol-1-yloxytris(dimethylamino) phosphonium hexafluorophosphate (BOP) in the presence of a carbodiimide, such as diisopropylcarbodiimide or dicyclohexylcarbodiimide, and, if appropriate, a tertiary amine (e.g. diisopropylamine).

Compounds of the formula IV can also be obtained by converting a compound IV in which one of the groups $X^2$, $X^3$ and $X^4$ is C—O-allyl or C—O-benzyl into the corresponding phenol, followed, if desired, by alkylation. The allyl group is preferably removed in an aprotic solvent [e.g. tetrahydrofuran ("THF")], using a palladium(O) catalyst [e.g. tetrakis(triphenylphosphine)palladium in THF], in the presence of a reducing agent (e.g. sodium borohydride). The benzyl group is preferably removed by catalytic hydrogenation (Pd/C) in a solvent (e.g. ethanol and dioxane). The resulting phenol can then, if desired, be alkylated in a solvent, such as THF, using triphenylphosphine and diethyl azodicarboxylate as catalyst, and in an appropriate alcohol. The alkylation can also be carried out using a suitable alkyl bromide in acetone or DMF in the presence of $K_2CO_3$.

Reactive groups present in the compounds of the formulas I and IV to VI can be functionally derivatized for example as follows:

A C—$NO_2$ group $X^1$, $X^2$, $X^3$ or $X^4$ can be reduced by catalytic hydrogenation (Pd, Pt or Ni) in a solvent, for example ethyl acetate and ethanol, to give the group C—$NH_2$.

A C—$NH_2$ group $X^1$, $X^2$, $X^3$ or $X^4$ can be acylated, for example, in THF in the presence of diisopropylethylamine using an acyl chloride, such as benzoyl chloride, to give the group C—NH-acyl. It is possible to employ the corresponding acid instead of the acyl chloride. In this case, the procedure is as described above for the reaction of an amine HN(R,Q) with an acid of the formula VI.

A C—Br group $X^1$, $X^2$, $X^3$ or $X^4$ can be converted into a C-alkyl group or a group $X^1$, $X^2$, $X^3$ or $X^4$ which is attached via alkyl. In a first step, for example, a bromide IV is converted in dimethylacetamide using a terminally unsaturated compound, such as $CH_2$=CH-alkyl-COOH, triethylamine, Pd acetate and tri-o-tolyl phosphine into the corresponding compound IV in which $X^1$, $X^2$, $X^3$ or $X^4$ denotes CCH=CH-alkyl-COOH. The resulting unsaturated acid IV is hydrogenated, for example, in ethanol and THF using hydrochloric acid and Pd/C to give the corresponding acid IV in which $X^1$, $X^2$, $X^3$ or $X^4$ is $CCH_2CH_2$-alkyl-COOH.

A group COO-alkyl present in a group R can be hydrolysed in THF using LiOH to give COOH.

To convert CN into a group $C(N—G^1)NH—G^2$ in which one of the groups $g^1$ and $g^2$ is H and the other is OH, the nitrile starting material of the formula IV is dissolved in a solvent such as DMF, ethanol or methanol and added to a reaction solution comprising a base, such as diisopropylethylamine or triethylamine, sodium hydride, sodium methoxide or sodium hydroxide, and hydroxylamine or a salt of hydroxylamine with an inorganic acid, such as hydroxylamine hydrochloride, advantageously at a temperature of up to 80° C.

To convert CN into $C(NH)NH_2$, the nitrile starting material can be gassed in a solvent (e.g. ethanol or methanol), or a solvent mixture (e.g. chloroform and methanol or chloroform and ethanol), using a dry stream of hydrogen chloride, advantageously at a temperature of below 10° C. The reaction solution is admixed with a solvent (e.g. diethyl ether), and the intermediate which is precipitated in this way is filtered off. The intermediate can then be dissolved in water, neutralized with a base (e.g. sodium carbonate or sodium hydroxide) and extracted from the aqueous phase using a solvent (e.g. dichloromethane, chloroform or ethyl acetate). The resulting material is treated in a solvent (e.g. methanol or ethanol) either with gaseous ammonia or an ammonium salt (e.g. ammonium chloride), advantageously at a temperature of up to 80° C. Alternatively, the intermediate is filtered off and immediately treated with gaseous ammonia or an ammonium salt in methanol or ethanol.

To convert CN into $C(NH)NH_2$, it is also possible to hydrogenate the amidoximes of the formula I which are obtained after conversion of CN into a group $C(N—G^1)$ $NH—G^2$, in which one of the groups $G^1$ and $G^2$ is H and the other is OH, in a solvent, such as ethanol, methanol, dioxane, THF or glacial acetic acid, or in a solvent mixture (e.g. ethanol and glacial acetic acid), using hydrogen and a catalyst (e.g. palladium, platinum or nickel). A nitro group $R^a$, $R^b$, $R^c$ or $R^d$ which is contained in a compound of the formula I is reduced to the amino group. If the hydrogenation is carried out using palladium, a benzyloxy group $R^a$, $R^b$, $R^c$ or $R^d$ which is contained in an amidoxime of the formula I is converted into the hydroxyl group.

Reacting a compound of the formula I, in which $G^1$ and $G^2$ are hydrogen, in a solvent such as dichloromethane, dioxane or DMF, or a solvent mixture such as dichloromethane and water or ethyl acetate and water in the presence of an organic base such as pyridine or triethylamine, or an inorganic base such as sodium hydroxide, sodium carbonate or potassium bicarbonate, with a chloroformate of the formula ClC(O)O—A or a 2,4- dinitrophenyl formate of the formula [2,4(NO$_2$)$_2$-C$_6$H$_3$]OC(O)O—A gives the corresponding compound in which G$^1$ or G$^2$ is the group C(O)O—A and A denotes alkyl.

Reacting a compound I in which G$^1$ and G$^2$ are hydrogen with an acyl chloride such as an aroyl chloride gives the corresponding compound of formula I in which one of the groups G$^1$ and G$^2$ is hydrogen and the other group is acyl. Analogously, it is possible to convert a compound I in which G$^1$ and G$^2$ are hydrogen with a p-nitrophenyl carbonate of the formula p-NO$_2$C$_6$H$_4$OCOO—R$^g$ into the corresponding compound I in which one of the groups G$^1$ and G$^2$ denotes COO—R$^g$. R$^g$ is optionally halogen-, OH-, alkoxy-, COOH- or COO-alkyl-substituted alkyl. To carry out the reaction, the acyl chloride or the p-nitrophenyl carbonate in THF and DMF is admixed first with N,N-diisopropylethylamine and then with the unsubstituted amidine of the formula I.

A protected amino group which is contained in a group R can be converted into the free amino group. Thus, a compound I which contains a Boc-protected amino group can be converted in methylene chloride with trifluoroacetic acid into the free amine I.

Moreover, some of the examples below contain details with respect to the preparation of certain starting materials and intermediates.

The compounds of the formulas IV, V and VI are novel and therefore also form part of the subject-matter of the present invention. The compounds of the formulas II and III are known or can be prepared analogously to the known compounds. Thus, the optionally 2-substituted 4-aminobenzamidines III are obtained from the corresponding 4-aminobenzonitriles via the 4-nitrobenzonitriles.

The compounds of the formula I and their solvates and salts inhibit the formation of the coagulation factors Xa, IXa and thrombin induced by the factor VIIa and the tissue factor. The compounds in question consequently influence both the platelet aggregation which is induced by these factors and plasmatic blood coagulation. They therefore inhibit the formation of thrombi and can be used for controlling or preventing diseases, such as thrombosis, apoplexy, cardiac infarction, inflammation and arteriosclerosis. Furthermore, these compounds have an effect on tumor cells and prevent metastases. They can therefore also be employed as antitumor agents.

The inhibition of the amidolytic activity of the factor VIIa/tissue factor complex by the compounds according to the invention was demonstrated with the aid of a chromogenic peptide substrate, as described below.

The measurements were carried out on microtiter plates at room temperature. To this end, per well of the plate, 100 µl of a solution of 26 nM of tissue factor, 9 nM of soluble factor VIIa and 8 mM of calcium chloride were added to 25 µl of a solution of the inhibitor in a buffer [pH 7.5, 100 mM, comprising 0.14 M NaCl, 0.1 M N(2-hydroxyethyl)piperazine-N'-(2-ethanesulphonic acid) (HEPES), 0.5 mg/l of fatty-acid-free BSA (bovine serum albumin) and 0.05% NaN$_3$]. After an incubation time of 15 minutes, the reaction was started by addition of 50 µl of chromogenic substrate Chromozym-tPA (3.5 mM, MeSO$_2$-D-Phe-Gly-Arg-paranitroanilide), and the hydrolysis of the substrate was followed spectrophotometrically on a kinetic microtiter plate reader over 10 minutes. Using the plot of the inhibition curves, the Ki values were determined according to the method described in *Biochem. J.*, 55:170–171 (1953). The results are shown in the table below (Ki in microM):

| Example | 1 | 2a | 5a | 5b | 5c | 5d | 5g | 6 | 7a |
|---|---|---|---|---|---|---|---|---|---|
| Ki | 0.057 | 0.283 | 0.281 | 0.195 | 0.169 | 0.116 | 0.044 | 0.22 | 0.19 |

| Example | 7e | 7f | 7h | 7n | 7s | 8 | 10 |
|---|---|---|---|---|---|---|---|
| Ki | 0.11 | 0.26 | 0.21 | 0.17 | 0.171 | 0.159 | 0.112 |

As mentioned at the outset, medicaments comprising a compound of the formula I, a solvate or a salt thereof also form part of the subject matter of the present invention. Furthermore, the subject matter also includes a process for preparing such medicaments, which is characterized in that one or more of such compounds, solvates or salts and, if desired, other therapeutically useful substances are prepared as pharmaceutical formulations. These medicaments can be administered orally, for example in the form of sugar-coated tablets, hard and soft gelatin capsules, solutions, emulsions or suspensions, or rectally, for example in the form of suppositories, or as a spray. However, administration can also be carried out parenterally, for example in the form of solutions for injection.

To prepare tablets, film tablets, sugar-coated tablets and hard gelatin capsules, the active ingredient can be mixed with pharmaceutically inert inorganic or organic excipients. Excipients which are suitable for tablets, film tablets, sugar-coated tablets and hard gelatin capsules include lactose, maize starch or derivatives thereof, talc, stearic acid or salts thereof. Excipients which are suitable for soft gelatin capsules include vegetable oils, waxes, fats, semi-solid and liquid polyols. Depending on the properties of the active ingredient, some soft gelatin capsules may not require any excipients at all. Excipients suitable for preparing solutions and syrups include water, polyols, sucrose, inverted sugar and glucose. Excipients suitable in solutions for injection include water, alcohols, polyols, glycerol and vegetable oils. Excipients suitable for use in suppositories are natural and hardened oils, waxes, fats, semi-liquid or liquid polyols. In addition, pharmaceutical preparations may also contain preservatives, solubilizers, stabilizers, wetting agents, emulsifiers, sweeteners, colorants, aromas, salts to modify the osmotic pressure, buffers, coatings or antioxidants.

The dosage of the active ingredient for the control and/or prevention of the diseases mentioned above can vary within wide limits and must of course be adapted to the individual circumstances in each individual case. In general, for oral or parenteral administration (e.g. intravenous or subcutaneous administration), a dose of about 0.1 to 20 mg/kg, preferably about 0.6 to 4 mg/kg, per day should be adequate for adults. The upper limit which has just mentioned may be exceeded or the dose may be lowered, should this be deemed appropriate by the administering physician.

The following examples have actually been performed.

EXAMPLE 1

At room temperature, 1 mmol of 4-aminobenzamidine dihydrochloride (208 mg), 1 mmol of triethylamine (101 mg), 1 mmol of benzylisonitrile (117 mg) and 1 mmol of 4-benzyloxy-3-methoxybenzaldehyde (260 mg) was stirred in a solvent mixture of 1.2 ml of isopropanol and 0.8 ml of water for 5 days. The mixture was then admixed with 0.5 ml of 25% strength hydrochloric acid and stirred at room temperature for 1 hour. The precipitated crystals was filtered off and washed with 5 ml of water. This yielded 218 mg (41%) of (R,S)-N-benzyl-2-(4-benzyloxy-3-methoxyphenyl)-2-(4-carbamimidoylphenylamino) acetamide hydrochloride as colorless crystals. ISP-MS: 495.5 ([M+H]$^+$, 100).

EXAMPLE 2

By the method of Example 1, the following compounds were prepared:

2.a) 4-aminobenzamidine dihydrochloride, triethylamine, benzylisonitrile and 3,4-dimethoxybenzaldehyde gave (R,S)-N-benzyl-2-(4-carbamimidoylphenylamino)- 2-(3,4-dimethoxyphenyl)acetamide hydrochloride as colorless crystals. ISP-MS: 455 ([M+H]$^+$, 100).

2.b) 4-aminobenzamidine dihydrochloride, triethylamine, benzylisonitrile and piperonylbenzaldehyde gave (R,S)-2-benzo[1,3]dioxol-5-yl-N-benzyl-2-(4-carbamimidoylphenylamino)acetamide hydrochloride as colorless crystals. ISP-MS: 439 ([M+H]$^+$, 100).

2.c) 4-aminobenzamidine dihydrochloride, triethylamine, benzylisonitrile and 2-hydroxy-4-methoxybenzaldehyde gave (R,S)-N-benzyl-2-(4-carbamimidoylphenylamino)-2-(2-hydroxy-4-methoxyphenyl)acetamide hydrochloride as colorless crystals. ISP-MS: 405 ([M+H]$^+$, 100).

2.d) 4-aminobenzamidine dihydrochloride, triethylamine, benzylisonitrile and 4-hydroxy-3-methoxy-5-nitrobenzaldehyde gave (R,S)-N-benzyl-2-(4-carbamimidoylphenylamino)-2-(4-hydroxy-3-methoxy-5-nitrophenyl)acetamide hydrochloride as colorless crystals. ISP-MS: 450 ([M+H]$^+$, 100).

2.e) 4-aminobenzamidine dihydrochloride, triethylamine, benzylisonitrile and 4-hydroxy-3,5-dimethoxybenzaldehyde gave (R,S)-N-benzyl-2-(4-carbamimidoylphenylamino)-2-(4-hydroxy-3,5-dimethoxyphenyl)acetamide hydrochloride as colorless crystals. ISP-MS: 435 ([M+H]$^+$, 100).

2.f) 4-aminobenzamidine dihydrochloride, triethylamine, benzylisonitrile and methyl 4-formylbenzoate gave methyl (R,S)-4-[benzylcarbamoyl-(4-carbamimidoylphenylamino) methyl]benzoate hydrochloride as colorless crystals. ISP-MS: 417 ([M+H]$^+$, 100).

2.g) 4-aminobenzamidine dihydrochloride, triethylamine, benzylisonitrile and 2,3,4-trimethoxybenzaldehyde gave (R,S)-N-benzyl-2-(4-carbamimidoylphenylamino)-2-(2,3,4-trimethoxyphenyl)acetamide hydrochloride as colorless crystals. ISP-MS: 449 ([M+H]$^+$, 100).

2.h) 4-aminobenzamidine dihydrochloride, triethylamine, benzylisonitrile and 3,4-dimethylbenzaldehyde gave (R,S)-N-benzyl-2-(4-carbamimidoylphenylamino)-2-(3,4-dimethylphenyl)acetamide hydrochloride as colorless crystals. ISP-MS: 387 ([M+H]$^+$, 100).

2.i) 4-aminobenzamidine dihydrochloride, triethylamine, benzylisonitrile and 4-methoxy3-methylbenzaldehyde gave (R,S)-N-benzyl-2-(4-carbamimidoyl phenylamino)-2-(4-methoxy-3-methylphenyl)acetamide hydrochloride as colorless crystals. ISP-MS: 403 ([M+H]$^+$, 100).

2.j) 4-aminobenzamidine dihydrochloride, triethylamine, benzylisonitrile and 4,5-dimethoxy2-nitrobenzaldehyde gave (R,S)-N-benzyl-2-(4-carbamimidoylphenylamino)-2-(4,5-dimethoxy-2-nitrophenyl)acetamide hydrochloride as colorless crystals. ISP-MS: 464 ([M+H]$^+$, 100).

2.k) 4-aminobenzamidine dihydrochloride, triethylamine, benzylisonitrile and 2,3-dimethoxybenzaldehyde gave (R,S)-N-benzyl-2-(4-carbamimidoylphenylamino)-2-(2,3-dimethoxyphenyl)acetamide hydrochloride as colorless crystals. ISP-MS: 419 ([M+H]$^+$, 100).

2.l) 4-aminobenzamidine dihydrochloride, triethylamine, benzylisonitrile and 2,4,5-trimethoxybenzaldehyde gave (R,S)-N-benzyl-2-(4-carbamimidoylphenylamino)-2-(2,4,5-trimethoxyphenyl)acetamide hydrochloride as colorless crystals. ISP-MS: 449 ([M+H]$^+$, 100).

2.m) 4-aminobenzamidine dihydrochloride, triethylamine, benzylisonitrile and 3-hydroxy-4-methoxybenzaldehyde gave (R,S)-N-benzyl-2-(4-carbamimidoylphenylamino)-2-(3-hydroxy-4-methoxyphenyl)acetamide hydrochloride as colorless crystals. ISP-MS: 405 ([M+H]$^+$, 100).

2.n) 4-aminobenzamidine dihydrochloride, triethylamine, benzylisonitrile and 2,4-dimethoxybenzaldehyde gave N-benzyl-2-(4-carbamimidoylphenylamino)-2-(2,4-dimethoxyphenyl)acetamide hydrochloride as colorless crystals. ISP-MS: 419 ([M+H]$^+$, 100).

2.o) 4-aminobenzamidine dihydrochloride, triethylamine, benzylisonitrile and 2-fluoro-4,5-dimethoxybenzaldehyde gave (R,S)-N-benzyl-2-(4-carbamimidoylphenylamino)-2-(2-fluoro-4,5-dimethoxyphenyl)acetamide hydrochloride as colorless crystals. ISP-MS: 437 ([M+H]$^+$, 100).

2.p) 4-aminobenzamidine dihydrochloride, triethylamine, cyclopropylmethylisonitrile and 3,4,5-trimethoxybenzaldehyde gave (R,S)-2-(4-carbamimidoylphenylamino)-N-cyclopropylmethyl-2-(3,4,5-trimethoxyphenyl)acetamide hydrochloride as colorless crystals. ISP-MS: 413 ([M+H]$^+$, 100).

2.q) 4-aminobenzamidine dihydrochloride, triethylamine, 3,4-dimethoxybenzylisonitrile and 3,4,5-trimethoxybenzaldehyde gave (R,S)-2-(4-carbamimidoylphenylamino)-N-(3,4-dimethoxybenzyl)-2-(3,4,5-trimethoxyphenyl)acetamide hydrochloride as colorless crystals. ISP-MS: 509 ([M+H]$^+$, 100).

2.r) 4-aminobenzamidine dihydrochloride, triethylamine, benzylisonitrile and methyl 2-(formyl-2-methoxyphenoxy) benzoate gave methyl (R,S)-2-{4-[benzylcarbamoyl-(4-carbamimidoylphenylamino)methyl]-2-methoxyphenoxy}benzoate hydrochloride as colorless crystals. ISP-MS: 539.4 ([M+H]$^+$, 100).

2.s) 4-aminobenzamidine dihydrochloride, triethylamine, 2-phenylethylisonitrile and 4-dimethylamino-3-nitrobenzaldehyde gave (R,S)-N-(2-phenylethyl)-2-(4-carbamimidoylphenylamino)-2-(4-dimethylamino-3-nitrophenyl)acetamide hydrochloride as colorless crystals. ISP-MS: 461.7 ([M+H]$^+$, 100).

2.t) 4-aminobenzamidine dihydrochloride, triethylamine, benzylisonitrile and 3,5-dimethoxy-4-methylbenzaldehyde gave (R,S)-N-benzyl-2-(4-carbamimidoylphenylamino)-2-(3,5-dimethoxy-4-methylphenyl)acetamide hydrochloride as colorless crystals. ISP-MS: 433 ([M+H]$^+$, 100).

2.u) 4-aminobenzamidine dihydrochloride, triethylamine, benzylisonitrile and 3-phenoxybenzaldehyde gave (R,S)-N-benzyl-2-(3-phenoxyphenyl)-2-(4-carbamimidoylphenylamino)acetamide hydrochloride as colorless crystals. ISP-MS: 451.6 ([M+H]$^+$, 100).

2.v) 4-aminobenzamidine dihydrochloride, triethylamine, benzylisonitrile and 3,5-bis-benzyloxybenzaldehyde gave (R,S)-N-benzyl-2-(3,5-bis-benzyloxyphenyl)-2-(4-carbamimidoylphenylamino)acetamide hydrochloride as colorless crystals. ISP-MS: 571 ([M+H]$^+$, 100).

2.w) 4-aminobenzamidine dihydrochloride, triethylamine, benzylisonitrile and 3-benzyloxy-4-hydroxybenzaldehyde gave (R,S)-N-benzyl-2-(3-benzyloxy-4-hydroxyphenyl)-2-(4-carbamimidoylphenylamino)acetamide hydrochloride as colorless crystals. ISP-MS: 481 ([M+H]$^+$, 100).

2.x) 4-aminobenzamidine dihydrochloride, triethylamine, benzylisonitrile and 4-bromo-3,5-dimethoxybenzaldehyde gave (R,S)-N-benzyl-2-(4-bromo-3,5-dimethoxyphenyl)-2-(4-carbamimidoylphenylamino)acetamide hydrochloride as colorless crystals. ISP-MS: 498 ([M+H]$^+$, 100).

2.y) 4-aminobenzamidine dihydrochloride, triethylamine, benzylisonitrile and 3,5-dimethoxy-4-nitrobenzaldehyde gave (R,S)-N-benzyl-2-(4-carbamimidoylphenylamino)-2-(3,5-dimethoxy-4-nitrophenyl)acetamide hydrochloride as colorless crystals. ISP-MS: 464 ([M+H]$^+$, 100).

EXAMPLE 3

10 mmol of 4-aminobenzamidine dihydrochloride (2.8 g), 10 mmol of triethylamine (1.01 g), 0.5 ml of water, 10 mmol of 4-benzyloxy-3-methoxybenzaldehyde (2.6 g) and 10 mmol of benzylisonitrile (1.2 ml) were initially charged in 40 ml of methanol, and 3.8 ml of boron trifluoride etherate (30 mmol) are then added dropwise with ice-bath cooling over a period of 2 hours. The mixture was stirred at room temperature for a further hour, the solvent was then removed under reduced pressure and the crude product was chromatographed over an RP-18 column using water/methanol as mobile phase. Alternatively, the crude product was, with ice-cooling, admixed with 5 ml of 25% strength hydrochloric acid, 10 ml of dichloromethane and 10 ml of water were added and the precipitated crystals were filtered off with suction after 5 hours. This gave 1.6 g (30%) of (R,S)-N-benzyl-2-(4-benzyloxy-3-methoxyphenyl)-2-(4-carbamimidoylphenylamino)acetamide hydrochloride as colorless crystals. ISP-MS: 495.5 ([M+H]$^+$, 100). Chromatography of the crude product over an RP-18 column using a mobile phase of methanol/water with 0.1% of trifluoroacetic acid gave 0.8 g (15%) of (R,S)-N-benzyl-2-(4-benzyloxy-3-methoxyphenyl)-2-(4-carbamimidoylphenylamino)acetamide trifluoroacetate as colorless crystals. ISP-MS: 495.2 ([M+H]$^+$, 100).

EXAMPLE 4

10 mmol of 4-aminobenzonitrile (1.2 g), 0.5 ml of water, 10 mmol of 4-benzyloxy-3-methoxybenzaldehyde (2.6 g) were initially charged in 40 ml of methanol and stirred at room temperature for one hour, and 10 mmol of benzylisonitrile (1.2 ml) are then added dropwise and, with ice-bath cooling and stirring, 3.8 ml of boron trifluoride etherate were added over a period of 2 hours. The mixture was stirred at room temperature for a further hour, the solvent was then removed under reduced pressure and the crude product was filtered over a silica gel column using hexane/ethyl acetate 1/1 as mobile phase. The main fraction was concentrated and the resulting crude (R,S)-N-benzyl-2-(4-benzyloxy-3-methoxyphenyl)-2-(4-cyanophenylamino)acetamide was dissolved in a solvent mixture of 20 ml of chloroform and 4 ml of methanol and, with stirring and at a temperature of below 5° C., gassed with dry hydrogen chloride for 20 minutes. The reaction mixture was then allowed to stand at 5° C. for 24 hours, 20 ml of diethyl ether are then added and the precipitated crystals were filtered off with suction and washed with diethyl ether and the residue was taken up in methanol which was saturated with ammonia. The ammonia solution was boiled under reflux for 2 hours and the solvent was then removed using a water pump vacuum. 5 ml of a 1 N solution of hydrochloric acid were then added to the residue, and the solvent was once more removed using a water pump vacuum. The resulting crude product was chromatographed over an RP-18 column using water/methanol as mobile phase. This gave 228 mg (43%) of (R,S)-N-benzyl-2-(4-benzyloxy-3-methoxyphenyl)-2-(4-carbamimidoylphenylamino)acetamide hydrochloride as colorless crystals. ISP-MS: 495.5 ([M+H]$^+$, 100).

EXAMPLE 5

By the method of Example 4, the following compounds were prepared:

5.a) 4-aminobenzonitrile, benzylisonitrile and 3,4,5-trimethoxybenzaldehyde gave (R,S)-N-benzyl-2-(4-carbamimidoylphenylamino)-2-(3,4,5-trimethoxyphenyl)acetamide hydrochloride as colorless crystals. ISP-MS: 449.2 ([M+H]$^+$, 100).

5.b) 4-aminobenzonitrile, benzylisonitrile and 3,5-dimethoxybenzaldehyde gave (R,S)-N-benzyl-2-(4-carbamimidoylphenylamino)-2-(3,5-dimethoxyphenyl)acetamide hydrochloride as colorless crystals. ISP-MS: 419 ([M+H]$^+$, 100).

5.c) 4-aminobenzonitrile, benzhydrylisonitrile and 3,4-dimethoxybenzaldehyde gave (R,S)-N-benzhydryl-2-(4-carbamimidoylphenylamino)-2-(3,4-dimethoxyphenyl)acetamide hydrochloride as colorless crystals. ISP-MS: 495 ([M+H]$^+$, 100).

5.d) 4-aminobenzonitrile, benzylisonitrile and 3,4-diethoxybenzaldehyde gave (R,S)-N-benzyl-2-(4-carbamimidoylphenylamino)-2-(3,4-diethoxyphenyl)acetamide hydrochloride as colorless crystals. ISP-MS: 447.2 ([M+H]$^+$, 100).

5.e) 4-aminobenzonitrile, benzhydrylisonitrile and 4-benzyloxy-3-methoxybenzaldehyde gave (R,S)-N-benzhydryl-2-(4-benzyloxy-3-methoxyphenyl)-2-(4-carbamimidoylphenylamino)acetamide hydrochloride as colorless crystals. ISP-MS: 571.4 ([M+H]$^+$, 100).

5.f) 4-aminobenzonitrile, benzhydryliso-nitrile and 4-benzyloxy-3-ethoxybenzaldehyde gave (R,S)-N-benzhydryl-2-(4-benzyloxy-3-ethoxyphenyl)-2-(4-carbamimidoylphenylamino)acetamide hydrochloride as colorless crystals. ISP-MS: 585.4 ([M+H]$^+$, 100).

5.g) 4-aminobenzonitrile, benzylisonitrile and 4-benzyloxy-3-ethoxybenzaldehyde gave (R,S)-N-benzyl-2-(4-benzyloxy-3-ethoxyphenyl)-2-(4-carbamimidoylphenylamino)acetamide hydrochloride as colorless crystals. ISP-MS: 509.4 ([M+H]$^+$, 100).

5.h) 4-aminobenzonitrile, 4-methoxybenzylisonitrile and 4-benzyloxy-3-methoxybenzaldehyde gave (R,S)-2-(4-benzyloxy-3-methoxyphenyl)-2-(4-carbamimidoylphenylamino)-N-(4-methoxybenzyl)acetamide hydrochloride as colorless crystals. ISP-MS: 525.2 ([M+H]$^+$, 100).

5.i) 4-aminobenzonitrile, naphthyl-1-yl-methylisonitrile and 4-benzyloxy-3-methoxybenzaldehyde gave (R,S)-2-(4-benzyloxy-3-methoxyphenyl)-2-(4-carbamimidoylphenylamino)-N-naphthalen-1-yl-methylacetamide hydrochloride as colorless crystals. ISP-MS: 545.3 ([M+H]$^+$, 100).

5.j) 4-aminobenzonitrile, benzylisonitrile and 3-butoxy-5-methoxybenzaldehyde gave (R,S)-N-benzyl-2-(3-butoxy-5-methoxyphenyl)-2-(4-carbamimidoyl-phenylamino)acetamide hydrochloride as colorless crystals. ISP-MS: 461.3 ([M+H]$^+$, 100).

5.k) 4-aminobenzonitrile, benzylisonitrile and 3-benzyloxy-5-ethoxybenzaldehyde gave (R,S)-N-benzyl-2-(3-benzyloxy-5-ethoxyphenyl)-2-(4-carbamimidoylphenylamino)acetamide hydrochloride as colorless crystals. ISP-MS: 509.4 ([M+H]$^+$, 100).

5.l) 4-aminobenzonitrile, benzylisonitrile and 3-benzyloxy-5-methoxybenzaldehyde gave (R,S)-N-benzyl- 2-(3-benzyloxy-5-methoxyphenyl)-2-(4-carbamimidoylphenylamino)acetamide hydrochloride as colorless crystals. ISP-MS: 495.3 ([M+H]$^+$, 100).

EXAMPLE 6

Under an atmosphere of argon, a NaOMe solution was freshly prepared from 130 mg (5.6 mmol) of sodium and 10 ml of MeOH, and the solution was admixed with 474 mg (6.8 mmol) of hydroxylamine hydrochloride. The suspension was stirred at room temperature for 30 min. 286 mg (0.6 mmol) of (R,S)-N-benzyl-2-(4-cyanophenylamino)-2-[3-methoxy-4-(3-methoxybenzyloxy)phenyl]acetamide (Example 18) were added and the reaction mixture was heated under reflux overnight. The solvent was subsequently distilled off under reduced pressure. The residue was taken up in water and extracted with EtOAc. The organic phase was washed with saturated NaCl solution, dried over MgSO$_4$, filtered and concentrated under reduced pressure.

The residue was taken up in 10 ml of ethanol, 1 ml of THF and 1 ml of HOAc and admixed with a spatula tip of Raney nickel. The reaction mixture was hydrogenated for 5 h. The catalyst was filtered off. The filtrate was concentrated under reduced pressure. The residue was purified by silica gel chromatography (EtOAc/acetone/H$_2$O/HOAc 6:2:1:1). This gave 191 mg (53%) of (R,S)-N-benzyl-2-(4-carbamimidoylphenylamino)-2-[3-methoxy-4-(3-methoxybenzyloxy)phenyl]) acetamide acetate as colorless crystals. ISP-MS: 525.2 ([M+H]).

EXAMPLE 7

By the method of Example 6, the following compounds were obtained:

7.a) (R,S)-N-benzyl-2-(4-cyanophenylamino)-2-[3-methoxy-4-(pyridin-4-ylmethoxy)phenyl]acetamide (Example 19.a) gave N-benzyl-2-(4-carbamimidoylphenylamino)-2-[3-methoxy-4-(pyridin-4-ylmethoxy)phenyl]acetamide acetate in a yield of 18%. Colorless solid. ISP-MS: 496.2 ([M+H]).

7.b) (R,S)-N-benzyl-2-(4-cyanophenylamino)-2-[3-methoxy-4-(2-morpholin-4-ylethoxy)phenyl]acetamide (Example 19.b) gave (R,S)-N-benzyl-2-(4-carbamimidoylphenylamino)-2-[3-methoxy-4-(2-morpholin-4-ylethoxy)phenyl]acetamide acetate in a yield of 15%. Colorless solid. ISP-MS: 518.3 ([M+H]).

7.c) (R,S)-N-benzyl-2-(4-cyanophenylamino)-2-[3-methoxy-4-(2-thiomorpholin-4-ylethoxy)phenyl]acetamide (Example 19.c) gave (R,S)-N-benzyl-2-(4-carbamimidoylphenylamino)-2-[3-methoxy-4-(2-thiomorpholin-4-ylethoxy)phenyl]) acetamide acetate in a yield of 22%. Yellow-green solid. ISP-MS: 534.3 ([M+H]).

7.d) (R,S)-N-benzyl-2-(4-cyanophenylamino)-2-[3-methoxy-4-(3-phenoxybenzyloxy)phenyl]acetamide (Example 19.d) gave (R,S)-N-benzyl-2-(4-carbamimidoylphenylamino)-2-[3-methoxy-4-(3-phenoxybenzyloxy)phenyl]acetamide acetate in a yield of 28%. Colorless solid. ISP-MS: 587.4 ([M+H]).

7.e) (R,S)-N-benzyl-2-(4-cyanophenylamino)-2-[4-(1H-indol-5-ylmethoxy)-3-methoxyphenyl]acetamide (Example 19.e) gave (R,S)-N-benzyl-2-(4-carbamimidoylphenylamino)-2-[4-(1H-indol-5-ylmethoxy)-3-methoxyphenyl]acetamide acetate in a yield of 23%. Colorless solid. ISP-MS: 534.3 ([M+H]).

7.f) (R,S)-N-benzyl-2-(4-cyanophenylamino)-2-[3-methoxy-4-(quinolin-7-ylmethoxy)phenyl]acetamide (Example 19.f) gave (R,S)-N-benzyl-2-(4-carbamimidoylphenylamino)-2-[3-methoxy-4-(1,2,3,4-tetrahydroquinolin-7-ylmethoxy)phenyl]acetamide acetate in a yield of 13%. Colorless solid. ISP-MS: 550.2 ([M+H]).

7.g) (R,S)-N-benzyl-2-(4-cyanophenylamino)-2-[3-methoxy-4-(quinolin-7-ylmethoxy)phenyl]acetamide (Example 19.f) gave (R,S)-N-benzyl-2-(4-carbamimidoylphenylamino)-2-[3-methoxy-4-(quinolin-7-ylmethoxy)phenyl]acetamide acetate in a yield of 16%. Slightly pink solid. ISP-MS: 546.3 ([M+H]).

7.h) (R,S)-N-benzyl-2-(4-cyanophenylamino)-2-[3-methoxy-4-phenethyloxyphenyl) acetamide (Example 19.g) gave (R,S)-N-benzyl-2-(4-carbamimidoylphenylamino)-2-[3-methoxy-4-phenethyloxyphenyl)acetamide acetate in a yield of 21%. Colorless solid. ISP-MS: 509.4 ([M+H]).

7.i) (R,S)-N-benzyl-2-[4-(biphenyl-4-ylmethoxy)-3-methoxyphenyl]-2-(4-cyanophenylamino)acetamide (Example 19.h) gave (R,S)-N-benzyl-2-[4-(biphenyl-4-ylmethoxy)-3-methoxyphenyl]-2-(4-carbamimidoylphenylamino)acetamide acetate in a yield of 58%. Colorless solid. ISP-MS: 571.3 ([M+H]).

7.j) (R,S)-N-benzyl-2-(4-cyanophenylamino)-2-[4-(2,6-dichlorobenzyloxy)-3-methoxyphenyl]acetamide (Example 19.i) gave (R,S)-N-benzyl-2-(4-carbamimidoylphenylamino)-2-[4-(2,6-dichlorobenzyloxy)-3-methoxyphenyl]) acetamide acetate in a yield of 58%. Colorless solid. ISP-MS: 563.3 ([M+H]).

7.k) (R,S)-N-benzyl-2-(4-cyanophenylamino)-2-[4-(3,5-dichlorobenzyloxy)-3-methoxyphenyl]acetamide (Example 19.j) gave (R,S)-N-benzyl-2-(4-carbamimidoylphenylamino)-2-[4-(3,5-dichlorobenzyloxy)-3-methoxyphenyl]acetamide acetate in a yield of 47%. Colorless solid. ISP-MS: 563.3 ([M+H]).

7.l) (R,S)-N-benzyl-2-[4-(3-bromobenzyloxy)-3-methoxyphenyl]-2-(4-cyanophenylamino)acetamide (Example 19.k) gave (R,S)-N-benzyl-2-[4-(3-bromobenzyloxy)-3-methoxyphenyl]-2-(4-carbamimidoylphenylamino)acetamide acetate in a yield of 35%. Colorless solid. ISP-MS: 573 ([M+H]).

7.m) (R,S)-N-benzyl-2-(4-cyanophenylamino)-2-[3-methoxy-4-(pyridin-2-ylmethoxy)phenyl]acetamide (Example 19.l) gave (R,S)-N-benzyl-2-(4-carbamimidoylphenylamino)-2-[3-methoxy-4-(pyridin-2-ylmethoxy)phenyl]acetamide acetate in a yield of 34%. Colorless solid. ISP-MS: 496.3 ([M+H]).

7.n) (R,S)-N-benzyl-2-(4-cyanophenylamino)-2-[4-(isoquinolin-6-ylmethoxy)-3-methoxyphenyl]acetamide (Example 19.m) gave (R,S)-N-benzyl-2-(4-carbamimidoylphenylamino)-2-[4-(isoquinolin-6-ylmethoxyphenyl]acetamide acetate in a yield of 11%. Colorless solid. ISP-MS: 546.3 ([M+H]).

7.o) (R,S)-2-(4-benzyloxy-3-methoxyphenyl)-2-(4-cyanophenylamino)-N-(3,4-dimethoxybenzyl)acetamide (Example 24.a) gave (R,S)-2-(4-benzyloxy-3-methoxyphenyl)-2-(4-carbamimidoylphenylamino)-N-[3,4-dimethoxybenzyl)acetamide acetate in a yield of 5%. Colorless solid. ISP-MS: 555.3 ([M+H]).

7.p) (R,S)-2-(4-benzyloxy-3-methoxyphenyl)-2-(4-cyanophenylamino)-N-phenethylacetamide (Example 23) gave (R,S)-2-(4-benzyloxy-3-methoxyphenyl)-2-(4-carbamimidoylphenylamino)-N-phenethylacetamide acetate in a yield of 30%. Colorless solid. ISP-MS: 555.3 ([M+H]).

7.q) (R,S)-2-(4-benzyloxy-3-methoxyphenyl)-2-(4-cyanophenylamino)-N-(4-nitrobenzyl)acetamide (Example 24.b) gave (R,S)-N-(4-aminobenzyl)-2-(4-benzyloxy-3-methoxyphenyl)-2-(4-carbamimidoylphenylamino)

acetamide acetate in a yield of 52%. Light-yellow solid. ISP-MS: 510.4 ([M+H]).

7.r) (R,S)-2-(4-benzyloxy-3-methoxyphenyl)-N-(4-cyanophenyl)-2-(4-cyanophenylamino)acetamide (Example 24.d) gave (R,S)-2-(4-benzyloxy-3-methoxyphenyl)-N-(4-carbamimidoylphenyl)-2-(4-carbamimidoylphenylamino) acetamide acetate in a yield of 30%. Colorless solid. ISP-MS: 523.3 ([M+H]).

7.s) (R,S)-2-(4-benzyloxy-3-methoxyphenyl)-2-(4-cyanophenylamino)-N-phenylacetamide (Example 24.c) gave (R,S)-2-(4-benzyloxy-3-methoxyphenyl)-2-(4-carbamimidoylphenylamino)-N-phenylacetamide acetate in a yield of 12%. Colorless solid. ISP-MS: 481.4 ([M+H]).

7.t) (R,S)-2-(4-benzyloxy-3-methoxyphenyl)-2-(4-cyanophenylamino)-N-[2-(3H-imidazol-4-yl)ethyl] acetamide (Example 24.e) gave (R,S)-2-(4-benzyloxy-3-methoxyphenyl)-2-(4-carbamimidoylphenylamino)-N-[2-(3H-imidazol-4-yl)ethyl]acetamide acetate in a yield of 9%. Colorless solid. ISP-MS: 482.4 ([M+H]).

7.u) (R,S)-2-(4-benzyloxy-3-methoxyphenyl)-2-(4-cyanophenylamino)-N-[2-(1H-indol-3-yl)ethyl]acetamide (Example 24.f) gave (R,S)-2-(4-benzyloxy-3-methoxyphenyl)-2-(4-carbamimidoylphenylamino)-N-[2-(1H-indol-3-yl)ethyl]acetamide acetate in a yield of 68%. Colorless solid. ISP-MS: 553.3 ([M+Na]), 548.3 ([M+NH4]), 531.3 ((M+H]).

EXAMPLE 8

440 mg of N-benzyl-2-(4-benzyloxy-2-phenylsulphonylamino-5-methoxyphenyl)-2-[4-(N-hydroxycarbamimidoyl)phenylamino]acetamide (0.66 mmol) (Example 14) were dissolved in 10 ml of MeOH, admixed with a drop of AcOH and admixed with 200 mg of 5% Pt/C. The reaction mixture was hydrogenated overnight. The catalyst was filtered off. The filtrate was concentrated under reduced pressure. The residue was purified by silica gel chromatography (EtOAc/acetone/H₂O/HOAc). This gave 263 mg of 2-(2-phenylsulphonylamino-4-benzyloxy-5-methoxyphenyl)-N-benzyl-2-(4-carbamimidoylphenylamino)acetamide acetate as a colorless solid. ISP-MS: 650 (M+H).

EXAMPLE 9

By the method of Example 8, N-benzyl-2-(4-benzyloxy-2-methanesulphonylamino-5-methoxyphenyl)-2-[4-(N-hydroxycarbamimidoyl)phenylamino]acetamide (Example 15) gave, after purification by HPLC over an RP-18 column using a mobile phase of CH₃CN/water with 0.1% of trifluoroacetic acid, N-benzyl-2-(4-benzyloxy-2-methanesulphonylamino-5-methoxyphenyl)-2-(4-carbamimidoylphenylamino)acetamide trifluoroacetate as a colorless solid. ISP-MS: 588 (M+H).

EXAMPLE 10

350 mg of N-benzyl-2-(4-benzyloxy-2-phenylsulphonylamino-5-methoxyphenyl)-2-[4-(N-hydroxycarbamimidoyl)phenylamino]acetamide (0.53 mmol) (Example 14) were dissolved in 3 ml of AcOH, admixed with 100 ml of Ac₂O and hydrogenated in the presence of 150 mg of 5% Pd/C overnight. The catalyst was filtered off. The filtrate was concentrated under reduced pressure. The residue was purified by silica gel chromatography (EtOAc/acetone/H₂O/HOAc). This gave 188 mg (64%) of 2-(2-phenylsulphonylamino-4-hydroxy-5-methoxyphenyl)-N-benzyl-2-(4-carbamimidoylphenylamino)acetamide acetate as a colorless solid. ISP-MS: 560 (M+H).

EXAMPLE 11

By the method of Example 10, N-benzyl-2-(4-benzyloxy-2-methanesulphonylamino-5-methoxyphenyl)-2-[4-(N-hydroxycarbamimidoyl)phenylamino]acetamide (Example 15) gave, after purification by HPLC over an RP-18 column using a mobile phase of CH₃CN/water with 0.1% of trifluoroacetic acid, N-benzyl-2-(4-carbamimidoylphenylamino)-2-(4-hydroxy-2-methanesulphonylamino-5-methoxyphenyl)acetamide trifluoroacetate as a colorless solid. ISP-MS: 498 (M+H).

EXAMPLE 12

Under an atmosphere of argon, an NaOMe solution was freshly prepared from 115 mg (5 mmol) of sodium and 15 ml of MeOH, and this solution was admixed with 420 mg (6 mmol) of hydroxylamine hydrochloride. The suspension was stirred at room temperature for 30 min. 261 mg (0.5 mmol) of (R,S)-N-benzyl-2-(4-cyanophenylamino)-2-[3-methoxy-4-(4-nitrobenzyloxy)phenyl]acetamide (Example 19.n) were added and the reaction mixture was then heated under reflux overnight. The solvent was subsequently distilled off under reduced pressure. The residue was taken up in water and extracted with EtOAc. The organic phase was washed with saturated NaCl solution, dried over MgSO₄, filtered and concentrated under reduced pressure. The residue was purified by silica gel chromatography (EtOAc). This gave 166 mg (60%) of (R,S)-N-benzyl-2-[4-(N-hydroxycarbamimidoyl)phenylamino]-2-[3-methoxy-4-(4-nitrobenzyloxy)phenyl]acetamide as a colorless solid foam. ISP-MS: 556.3 [M+H].

EXAMPLE 13

By the method of Example 12, 13.a) (R,S)-N-benzyl-2-(4-cyanophenylamino)-2-[3-methoxy-4-(pyridin-4-ylmethoxy)phenyl]acetamide (Example 19.a) gave (R,S)-N-benzyl-2-[4-(N-hydroxycarbamimidoyl)phenylamino]-2-[3-methoxy-4-(pyridin-4-ylmethoxy)phenyl]-acetamide in a yield of 35%. Colorless solid foam. ISP-MS: 512.4 ([M+H]).

13.b) (R,S)-N-benzyl-2-(4-cyanophenylamino)-2-[3-methoxy-4-(2-morpholin-4-ylethoxy)phenyl]acetamide (Example 19.b) gave (R,S)-N-benzyl-N-benzyl -2-[4-(N-hydroxycarbamimidoyl)phenylamino]-2-[3-methoxy-4-(2-morpholin-4-ylethoxy)phenyl]acetamide in a yield of 28%. Colorless solid foam. ISP-MS: 534.4 ([M+H]).

13.c) (R,S)-N-benzyl-2-(4-cyanophenylamino)-2-[3-methoxy-4-(3-phenoxybenzyloxy)phenyl]acetamide (Example 19.d) gave (R,S)-N-benzyl-2-[4-(N-hydroxycarbamimidoyl)phenylamino]-2-[3-methoxy-4-(4-phenoxybenzyloxy)phenyl]-acetamide in a yield of 40%. Slightly greyish solid foam. ISP-MS: 603.2 ([M+H]).

13.d) (R,S)-2-(4-benzyloxy-3-methoxyphenyl)-2-(4-cyanophenylamino)-N-(4-nitrobenzyl)acetamide (Example 24.b) gave (R,S)-2-(4-benzyloxy-3-methoxyphenyl)-2-[4-(N-hydroxycarbamimidoyl)phenylamino]-N-(4-nitrobenzyl)acetamide in a yield of 98%. Yellow oil. ISP-MS: 545.2 ([M+Na]), 540.3 ([M+NH₄]), 523.3 ([M+H]).

13.e) (R,S)-2-(4-benzyloxy-3-methoxyphenyl)-2-(4-cyanophenylamino)-N-[2-(3H-imidazol-4-yl)ethyl] acetamide (Example 24.e) gave (R,S)-2-(4-benzyloxy-3- methoxyphenyl)-2-[4-(N-hydroxycarbamimidoyl) phenylamino]-N-[2-(3H-imidazol-4-yl)ethyl]acetamide in a yield of 85%. A greyish-green solid foam. ISP-MS: 515.3 ([M+H]).

13.f) (R,S)-2-(4-benzyloxy-3-methoxyphenyl)-2-(4-cyanophenylamino)-N-[2-(1H-indol-3-yl)ethyl]acetamide (Example 24.f) gave (R,S)-2-(4-benzyloxy-3-methoxyphenyl)-2-[4-(N-hydroxycarbamimidoyl) phenylamino]-N-[1H-indol-3-yl)ethyl]acetamide in a yield of 85%. A greyish-green solid foam. ISP-MS: 564.4 ([M+H]).

13.g) (R,S)-N-benzyl-2-(4-cyanophenylamino)-2-(3,4,5-trimethoxyphenyl)acetamide (Example 17.a) gave (R,S)-N-benzyl-2-[4-(N-hydroxycarbamimidoyl)phenylamino]-2-(3,4,5-trimethoxyphenyl)acetamide as a colorless solid. ISP-MS: 465.6 ([M+H]$^+$, 100).

13.h) (R,S)-N-benzyl-2-(3,5-dimethoxyphenyl)-2-(4-cyanophenylamino)acetamide (Example 17.b) gave (R,S)-N-benzyl-2-(3,5-dimethoxyphenyl)-2-[4-(N-hydroxycarbamimidoyl)phenylamino]acetamide as a colorless solid. ISP-MS: 435.5 ([M+H]$^+$, 100).

13.i) (R,S)-N-benzyl-2-(4-benzyloxy-3-methoxy-phenyl)-2-(4-cyanophenylamino)acetamide (Example 17.c) gave (R,S)-N-benzyl-2-(4-benzyloxy-3-methoxyphenyl)-2-[4-(N-hydroxycarbamimidoyl)phenylamino]acetamide as a colorless solid. ISP-MS: 511.6 ([M+H]$^+$, 100).

13.j) (R,S)-N-benzyl-2-(4-benzyloxy-3-ethoxy-phenyl)-2-(4-cyanophenylamino)acetamide (Example 17.d) gave (R,S)-N-benzyl-2-(4-benzyloxy-3-ethoxyphenyl)-2-(4-(N-hydroxycarbamimidoyl)phenylamino]acetamide as a colorless solid. ISP-MS: 525.5 ([M+H]$^+$, 100).

EXAMPLE 14

995 mg of 2-(2-phenylsulphonylamino-4-benzyl-oxy-5-methoxyphenyl)-N-benzyl-2-(4-cyanophenylamino) acetamide (1.57 mmol) (Example 28), 547 mg of hydroxylamine hydrochloride (7.87 mmol) and 2.2 ml of triethylamine (15.7 mmol) were initially charged in 5 ml of EtOH. The reaction mixture was heated under reflux for 5 hours. The solvent was subsequently distilled off under reduced pressure. The residue was taken up in water and extracted with EtOAc. The organic phase was washed with saturated NaCl solution, dried over MgSO$_4$, filtered and concentrated under reduced pressure. This gave 885 mg (85%) of 2-(2-phenylsulphonylamino-4-benzyloxy-5-methoxyphenyl)-N-benzyl-2-[4-(N-hydroxycarbamimidoyl)phenylamino]) acetamide as an oily yellow solid. ISP-MS: 666 (M+H).

EXAMPLE 15

By the method of Example 14, N-benzyl-2-(4-benzyloxy-2-methanesulphonylamino-5-methoxyphenyl)-2-(4-cyanophenylamino)acetamide (Example 29) gave N-benzyl-2-(4-benzyloxy-2-methanesulphonylamino-5-methoxyphenyl)-2-[4-(N-hydroxycarbamimidoyl) phenylamino]acetamide as a yellow oil in a yield of 95%. ISP-MS: 604 (M+H).

EXAMPLE 16

10 g of 4-benzyloxy-5-methoxy-2-nitrobenz-aldehyde (34.8 mmol) and 4.11 g of 4-aminobenzonitrile (34.8 mmol) were dissolved in 140 ml of methanol and stirred at room temperature for one hour. The mixture was then admixed with 4.25 ml of benzylisonitrile (34.8 mol). 12.9 ml of boron trifluoride etherate (104.4 mmol) were subsequently added to this mixture, dropwise and with ice-bath cooling, over a period of half an hour. After 30 min, the ice bath was removed. The reaction mixture was stirred at room temperature for another 2 days. The solvent was subsequently distilled off under reduced pressure. The residue was taken up in EtOAc and washed with water. The organic phase was dried over MgSO$_4$, filtered and concentrated under reduced pressure. The crude product was purified by silica gel chromatography using acetone/toluene (3/97). This gave 8.9 g (48%) of N-benzyl-2-(4-benzyloxy-5-methoxy-2-nitrophenyl)-2-(4-cyanophenylamino)acetamide as an oily orange solid. ISP-MS: 523 (M+H).

EXAMPLE 17

By the method of Example 16:

17.a) 4-aminobenzonitrile, 3,4,5-trimethoxybenzaldehyde and benzylisonitrile gave (R,S)-N-benzyl-2-(4-cyanolphenylamino-2-(3,4,5-trimethoxyphenyl)acetamide as colorless crystals. $^1$H NMR (DMSO-D$_6$): 8.80 (t;NH;1H), 5.02 (d;CH;1H), 4.28 (d;CH$_2$;2H), 3.75 (s;CH$_3$;6H), 2.61 (s; CH$_3$;3H).

17.b) 4-aminobenzonitrile, 3,5-dimethoxybenzaldehyde and benzylisonitrile gave (R,S)-N-benzyl-2-(3,5-dimethoxyphenyl)-2-(4-cyanophenylamino)acetamide as colorless crystals. $^1$H NMR (DMSO-D$_6$): 8.82 (t;NH;1H), 5.15 (d;CH;1H), 4.28 (d;CH$_2$;2H), 3.72 (s;CH$_3$;6H).

17.c) 4-aminobenzonitrile, 4-benzyloxy-3-methoxybenzaldehyde and benzylisonitrile gave (R,S)-N-benzyl-2-(4-benzyloxy-3-methoxyphenyl)-2-(4-cyanophenylamino)acetamide as colorless crystals. $^1$H NMR (DMSO-D$_6$): 8.80 (t;NH;1H), 5.07 (d;CH;2H), 4.99 (d;CH;2H), 4.28 (s;CH$_2$;2H), 3.73 (s;CH$_3$;3H).

17.d) 4-aminobenzonitrile, 4-benzyloxy-3-ethoxybenzaldehyde and benzylisonitrile gave (R,S)-N-benzyl-2-(4-benzyloxy-3-ethoxyphenyl)-2-(4-cyanophenylamino)acetamide as colorless crystals. $^1$H NMR (DMSO-D$_6$): 8.75 (t;NH;1H), 5.10 (s;CH$_2$;2H), 4.95 (d;CH;1H), 4.28 (d;CH$_2$;2H), 4.05 (q;CH$_2$;2H), 1.32 (t;CH$_3$;3H).

EXAMPLE 18

Under an atmosphere of argon, a solution of 290 mg (0.75 mmol) of (R,S)-N-benzyl-2-(4-cyanophenylamino)-2-(4-hydroxy-3-methoxyphenyl)acetamide (Example 20), 110 ml (0.9 mmol) of 3-methoxybenzyl alcohol and 236 mg (0.9 mmol) of triphenylphosphine in 15 ml of THF were admixed with 140 ml (0.9 mmol) of diethyl azodicarboxylate, and the mixture was stirred at room temperature overnight. The reaction solution was concentrated under reduced pressure. The residue was purified by silica gel chromatography (CH$_2$Cl$_2$/EtOAc 9:1). This gave 326 mg (86%) of (R,S)-N-benzyl-2-(4-cyanophenylamino)-2-[3-methoxy-4-(3-methoxybenzyloxy)phenyl]acetamide as a colorless solid. ISP-MS: 530.2 ([M+Na]), 525.2 ([M+NH$_4$]), 508.4 ([M+H]), 390.2.

EXAMPLE 19

By the method of Example 18, (R,S)-N-benzyl-2-(4-cyanophenylamino)-2-(4-hydroxy-3-methoxyphenyl) acetamide 19.a) and 4-hydroxymethylpyridine gave (R,S)-N-benzyl-2-(4-cyanophenylamino-2-[3-methoxy-4-(pyridin-4-ylmethoxy)phenyl]acetamide in a yield of 72%. ISP-MS: 479.3 [M+H].

19.b) and N-(2-hydroxyethyl)morpholine gave (R,S)-N-benzyl-2-(4-cyanophenylamino)-2-[3-methoxy-4-(2- morpholin-4-ylethoxy)phenyl]acetamide in a yield of 66%. Colorless resin. ISP-MS: 501.3 [M+H].

19.c) and N-(2-hydroxyethyl)thiomorpholine [L. A. Burrows et al., *J. Am. Chem. Soc.*, 56: 1720 (1934)] gave (R,S)-N-benzyl-2-(4-cyanophenylamino)-2-(3-methoxy-4-(2-thiomorpholin-4-ylethoxy)phenyl]acetamide in a yield of 84%. Colorless solid foam. ISP-MS: 517.3 [M+H].

19.d) and 3-phenoxybenzylalcohol gave (R,S)-N-benzyl-2-(4-cyanophenylamino)-2-[3-methoxy-4-(3-phenoxybenzyloxy)phenyl]acetamide in a yield of 44%. Colorless solid foam. ISN-MS: 628.3 ([M+AcOH—H]), 568.3 [M–H].

19.e) and 5-hydroxymethylindole [M. Somei et al., *Chem. Pharm. Bull.*, 34: 4116 (1986)] gave (R,S)-N-benzyl-2-(4-cyanophenylamino)-2-[4-(1H-indol-5-ylmethoxy)-3-methoxyphenyl]acetamide in a yield of 67%. Light-yellow solid foam. ISP-MS: 539.3 ([M+Na]), 534.3 ([M+NH$_4$]), 517.2 ([M+H]), 399.3.

19.f) and 7-hydroxymethylquinoline [C. E. Kaslow et al., *J. Org. Chem.*, 18: 55 (1953)] gave (R,S)-N-benzyl-2-(4-cyanophenylamino)-2-[3-methoxy-4-(quinolin-7-ylmethoxy)phenyl]acetamide in a yield of 100%. Colorless solid. ISP-MS: 529.2 [M+H].

19.g) and 2-phenylethyl alcohol gave (R,S)-N-benzyl-2-(4-cyanophenylamino)-2-[3-methoxy-4-phenethyloxyphenyl)acetamide in a yield of 90%. Light-green resin. ISP-MS: 492.2 [M+H].

19.h) and 4-hydroxymethylbiphenyl gave (R,S)-N-benzyl-2-[4-(biphenyl-4-ylmethoxy)-3-methoxyphenyl]-2-(4-cyanophenylamino)acetamide in a yield of 25%. Colorless solid. ISN-MS: 612.3 ([M+AcOH—H]), 552.2 [M–H].

19.i) and 2,6-dichlorobenzyl alcohol gave (R,S)-N-benzyl-2-(4-cyanophenylamino)-2-[4-(2,6-dichlorobenzyloxy)-3-methoxyphenyl]acetamide in a yield of 70%. Colorless crystals. ISN-MS: 604.1 ([M+AcOH—H]), 544.1 [M–H].

19.j) and 3,5-dichlorobenzyl alcohol gave (R,S)-N-benzyl-2-(4-cyanophenylamino)-2-[4-(3,5-dichlorobenzyloxy)-3-methoxyphenyl]acetamide in a yield of 74%. Colorless crystals. ISN-MS: 604.1 ([M+AcOH—H]), 544.1 [M–H].

19.k) and 3-bromobenzyl alcohol gave (R,S)-N-benzyl-2-[4-(3-bromobenzyloxy)-3-methoxyphenyl]-2-(4-cyanophenylamino)acetamide in a yield of 51%. Colorless crystals. ISN-MS: 614.2 ([M+AcOH—H]), 556.0 [M–H].

19.l) and 2-hydroxymethylpyridine gave (R,S)-N-benzyl-2-(4-cyanophenylamino)-2-[3-methoxy-4-(pyridin-2-ylmethoxy)phenyl]acetamide in a yield of 89%. Colorless resin. ISP-MS: 479.3 [M+H].

19.m) and 6-hydroxymethylisoquinoline (EP 385 662) gave (R,S)-N-benzyl-2-(4-cyanophenylamino)-2-[4-(isoquinolin-6-ylmethoxy)-3-methoxyphenyl]acetamide in a yield of 100%. Colorless solid. ISP-MS: 529.3 [M+H].

19.n) and 4-nitrobenzyl alcohol gave (R,S)-N-benzyl-2-(4-cyanophenylamino)-2-[3-methoxy-4-(4-nitrobenzyloxy) phenyl]acetamide in a yield of 71%. Light-yellow, solid foam. ISN-MS: 581.2 ([M+AcOH—H]), 521.2 [M+H].

EXAMPLE 20

460 mg (0.4 mmol) of tetrakis(triphenylphosphine) palladium were added to a solution of 8.5 g (20 mmol) of (R,S)-2-(4-allyloxy-3-methoxyphenyl)-N-benzyl-2-(4-cyanophenylamino)acetamide (Example 21) in 250 ml of THF. The solution was stirred at room temperature for 10 min and then admixed with 1.13 g (30 mmol) of NaBH$_4$. The mixture was stirred at room temperature for 2 h and then concentrated under reduced pressure. The residue was taken up in CH$_2$Cl$_2$/EtOAc 9:1 and stirred in the presence of activated carbon for 30 min. The suspension was filtered through Dicalite. The filtrate was concentrated under reduced pressure and the residue was recrystallized from EtOAc/hexane. This gave 6.81 g (88%) of (R,S)-N-benzyl-2-(4-cyanophenylamino)-2-(4-hydroxy-3-methoxyphenyl) acetamide as colorless crystals. ISN-MS: 386.1 ([M–H]), 268.3.

EXAMPLE 21

A solution of 17.8 g (35 mmol) of methyl (R,S)-2-(4-allyloxy-3-methoxyphenyl)-N-benzyl-2-(4-cyanophenylamino)acetamidate (Example 22) in 35 ml of DMSO was stirred at room temperature overnight. The solvent was evaporated off under high vacuum. The residue was purified by silica gel chromatography (CH$_2$Cl$_2$/EtOAc 19:1. This gave 10.6 g (71%) of (R,S)-2-(4-allyloxy-3-methoxyphenyl)-N-benzyl-2-(4-cyanophenylamino) acetamide as a colorless solid. ISN-MS: 486.1 ([M+AcOH—H]), 426.1 [M–H].

EXAMPLE 22

Under an atmosphere of argon, a solution of 17.72 g (150 mmol) of 4-aminobenzonitrile and 28.8 g of 4-allyloxy-3-methoxybenzaldehyde (W. A. Ayer, P. A. Craw, Can. J. Chem. (1991) 69, 1909) was stirred at room temperature for 1 h. 18.3 ml (150 mmol) of benzylisonitrile were added. At 0° C., 56 ml (450 mmol) of boron trifluoride ethyl etherate were subsequently slowly added dropwise. After a short period of time, crystals formed, which were filtered off under an atmosphere of argon and dried under high vacuum. This gave 74.1 g (87%) of methyl (R,S)-2-(4-allyloxy-3-methoxyphenyl)-N-benzyl-2-(4-cyanophenylamino) acetimidate as a light-yellow solid. ISP-MS: 442.3 [M+H].

EXAMPLE 23

Under an atmosphere of argon, 144 mg (0.75 mmol) of N-(3-dimethylaminopropyl)-N'-ethylcarbodiimide hydrochloride were added to a solution of 194 mg (0.5 mmol) of (R,S)-(4-benzyloxy-3-methoxyphenyl)-(4-cyanophenylamino) acetic acid (Example 25), 75 ml (0.6 mmol) of phenethylamine, 115 mg (0.75 mmol) of 1-hydroxybenzotriazole and 128 ml (0.75 mmol) of N,N-diisopropylethylamine in 2.5 ml of THF. The reaction mixture was stirred at room temperature for 5 h and then concentrated under reduced pressure. The residue was taken up in EtOAc and washed with saturated KHCO$_3$ solution, with 2% strength citric acid solution, with H$_2$O and then with saturated NaCl solution. The organic phase was dried over MgSO$_4$, filtered and concentrated under reduced pressure. The crude product was purified by silica gel chromatography (cyclohexane/EtOAc 2:1). This gave 210 mg (86%) of (R,S)-2-(4-benzyloxy-3-methoxyphenyl)-2-(4-cyano-phenylamino)-N-phenethylacetamide as a colorless solid foam. ISP-MS: 492.3 ([M+Na]), 509.4 ([M+NH4]), 523.3 ([M+H]).

EXAMPLE 24

By the method of Example 23, (R,S)-(4-benzyloxy-3-methoxyphenyl)-(4-cyanophenylamino)acetic acid 24 a) and veratrylamine gave (R,S)-2-(4-benzyloxy-3-methoxyphenyl)-2-( 4-cyanophenylamino)-N-(3,4-dimethoxybenzyl)acetamide in a yield of 80%. Light-yellow, solid foam. ISP-MS: 560.4 ([M+Na]), 555.3 ([M+NH4]), 538.4 ([M+H]).

24 b) and 4-nitrobenzylamine hydrochloride gave (R,S)-2-(4-benzyloxy-3-methoxyphenyl)-2-(4-cyanophenylamino)-N-(4-nitrobenzyl)acetamide in a yield of 43%. Colorless solid. ISP-MS: 545.2 ([M+Na]), 540.3 ([M+NH$_4$]), 523.2 ([M+H]).

24 c) and aniline gave (R,S)-2-(4-benzyloxy-3-methoxyphenyl)-2-(4-cyanophenylamino)-N-phenylacetamide in a yield of 52%. Colorless solid. ISP-MS: 486.2 ([M+Na]), 464.2 ([M+H]).

24 d) and 4-aminobenzonitrile gave (R,S)-2-(4-benzyloxy-3-methoxyphenyl)-N-(4-cyanophenyl)-2-(4-cyanophenylamino)acetamide in a yield of 10%. Colorless solid, ISN-MS: 547.2 ([M+AcOH—H]), 487.2 ([M–H]).

24 e) and histamine dihydrochloride gave (R,S)-2-(4-benzyloxy-3-methoxyphenyl)-2-(4-cyanophenylamino)-N-[2-(3H-imidazole-4-yl)ethyl]acetamide in a yield of 74%. Colorless solid foam. ISP-MS: 482.4 ([M+H]).

24 f) and tryptamine gave (R,S)-2-(4-benzyloxy-3-methoxyphenyl)-2-(4-cyanophenylamino)-N-[2-(1H-indol-3-yl)ethyl]acetamide in a yield of 92%. Orange solid foam. ISP-MS: 553.3 ([M+Na]), 548.3 ([M+NH4]), 531.3 [M+H].

EXAMPLE 25

A solution of 1.17 g (2.9 mol) of methyl (R,S)-(4-benzyloxy-3-methoxyphenyl)-(4-cyanophenylamino)acetate in 6 ml of THF was cooled to 0° C. and admixed with 14.5 ml (14.5 mmol) of 1N LiOH solution. The mixture was stirred at 0° C. for 30 min and at room temperature for 2 h. The THF was distilled off under reduced pressure. The solution that remained was adjusted to pH 3 using 1N HCl. A colorless precipitate formed, which was filtered off and washed with water. The solid was recrystallized in EtOH/H$_2$O. This gave 788 mg (70%) of (R,S)-(4-benzyloxy-3-methoxyphenyl)-(4-cyanophenylamino)acetic acid as a colorless solid. ISN-MS: 387.1 ([M–H]).

EXAMPLE 26

Under an atmosphere of argon, a solution of 970 mg (4 mmol) of 4-benzyloxy-3-methoxybenzaldehyde and 473 mg (4 mmol) of 4-aminobenzonitrile in 16 ml of MeOH was stirred at room temperature for 1 h. A light-yellow precipitate formed. The suspension was admixed with 488 ml (4 mmol) of benzylisonitrile and cooled to 0° C. 1.52 ml (12 mmol) of boron trifluoride ethyl etherate were then slowly added dropwise. After 2 h, the mixture was allowed to warm to room temperature and concentrated under reduced pressure. The residue was taken up in MeOH. The solution was slowly admixed with water until crystallization set in. The mixture was allowed to stand at 4° C. overnight. The solid was filtered off and dried under high vacuum. The residue was recrystallized from cyclohexane/EtOAc. This gave 1.17 g (73%) of methyl (R,S)-(4-benzyloxy-3-methoxyphenyl)-(4-cyanophenylamino)acetate as a colorless solid. ISP-MS: 425 ([M+Na]), 420.2 ([M+NH$_4$]).

EXAMPLE 27

2.0 g of N-benzyl-2-(4-benzyloxy-5-methoxy-2-nitrophenyl)-2-(4-cyanophenylamino)acetamide (3.8 mmol) (Example 16) were dissolved in 50 ml of EtOAc and 50 ml of EtOH, admixed with 1.2 g of 5% Pt/C and hydrogenated for 3 h. The catalyst was filtered off. The filtrate was concentrated under reduced pressure. This gave 1.42 g (76%) of 2-(2-amino-4-benzyloxy-5-methoxyphenyl)-N-benzyl-2-(4-cyanophenylamino)acetamide as an oily yellow solid. ISP-MS: 493 (M+H).

EXAMPLE 28

1.7 g of 2-(2-amino-4-benzyloxy-5-methoxyphenyl)-N-benzyl-2-(4-cyanophenylamino)acetamide (3.4 mmol) (Example 27) were dissolved in 60 ml of CH$_2$Cl$_2$ and 20 ml of DMF and admixed with 0.7 ml of Hünig base. At 0° C., 0.7 ml of phenylsulphonyl chloride (3.8 mmol) were subsequently added dropwise. The reaction mixture was stirred at room temperature for 4 hours and subsequently diluted with 100 ml of CH$_2$Cl$_2$ and washed with 5% NaHCO$_3$ solution. The organic phase was washed with saturated NaCl solution, dried over MgSO$_4$, filtered and concentrated under reduced pressure. The residue was purified by silica gel chromatography using acetone/toluene (10/90). This gave 995 mg (46%) of 2-(2-phenylsulphonylamino-4-benzyloxy-5-methoxyphenyl)-N-benzyl-2-(4-cyanophenylamino)acetamide as an oily orange solid. ISN-MS: 631 (M–H).

EXAMPLE 29

By the method of Example 28, 2-(2-amino-4-benzyloxy-5-methoxyphenyl)-N-benzyl-2-(4-cyanophenyl-amino)acetamide (Example 27) and methanesulphonyl chloride gave N-benzyl-2-(4-benzyloxy-2-methane-sulphonylamino-5-methoxyphenyl)-2-(4-cyanophenylamino)-acetamide as an orange solid in a yield of 36%. ISN-MS: 569 (M–H).

EXAMPLE 30

Under argon and at 0° C., 0.2 mmol of (R,S)-N-benzyl-2-(4-benzyloxy-3-methoxyphenyl)-2-(4-carbamimidoylphenylamino)acetamide trifluoroacetate (Example 3) (120 mg) in 1.3 ml of tetrahydrofuran are admixed with 0.335 mmol of O-methyl O'-(4-nitrophenyl) carbonate (66 mg). The reaction mixture is then allowed to warm to room temperature overnight, the solvent is removed under reduced pressure and the residue is extracted with ethyl acetate and water. The combined organic phases are dried over sodium sulphate. The mixture is filtered and the solvent is removed, and the residue is then suspended in diethyl ether and filtered off. This gaves 88 mg (82%) of methyl [amino-(4-{[benzylcarbamoyl-(4-benzyloxy-3-methoxyphenyl)-methyl]amino}phenyl)methylene] carbamate as a colorless solid. ISP-MS: 553.3 ([M+H]$^+$, 100).

EXAMPLE 31

By the method of Example 30, the following compounds are prepared:

31 a) (R,S)-N-benzyl-2-(4-carbamimidoylphenylamino)-1-(3,4-dimethoxyphenyl)acetamide hydrochloride (Example 2) gaves methyl [amino-(4-{[benzylcarbamoyl-(3,4-dimethoxyphenyl)methyl]-amino}phenyl)methylene] carbamate as a colorless solid. ISP-MS: 477.5 ([M+H]$^+$, 100).

31 b) (R,S)-N-benzyl-2-(4-carbamimidoylphenylamino)-2-(3,5-dimethoxyphenyl)acetamide hydrochloride (Example 5b) gaves methyl [amino-(4-{[benzylcarbamoyl-(3,5-dimethoxyphenyl)methyl]-amino}phenyl)methylene] carbamate as a colorless solid. ISP-MS: 477.5 ([M+H]$^+$, 100).

31 c) (R,S)-N-benzyl-2-(4-carbamimidoylphenylamino)-2-(3,4,5-trimethoxyphenyl)acetamide hydrochloride (Example 5a) gaves methyl [amino-(4-{[benzylcarbamoyl-(3,4,5-trimethoxyphenyl)methyl]-amino}phenyl)

methylene]carbamate as a colorless solid. ISP-MS: 507.6 ([M+H]+, 100).

A compound of the formula I, a hydrate, a solvate or a salt thereof can be used as an active ingredient for preparing pharmaceutical preparations, like those below.

EXAMPLE 32

A degassed solution of 369 mg of the material prepared according to the Example 36.3 in 5 ml of EtOH, 5 ml of THF, 2 ml of $H_2O$ and 1 ml of HOAc was admixed with a spatula tip of Raney nickel and hydrogenated for 5 hours. The catalyst was filtered off. The filtrate was concentrated. The residue was purified by silica gel chromatography (EtOAc/acetone/$H_2O$/HOAc 6:2:1:1). This gave the two epimers:

1. (S)-2-[(R)-2-(4-benzyloxy-3-methoxyphenyl)-2-(4-carbamimidoylphenylamino)acetylamino]propionic acid acetate (1:1) and
2. (S)-2-[(S)-2-(4-benzyloxy-3-methoxyphenyl)-2-(4-carbamimidoylphenylamino)acetylamino]propionic acid acetate (1:1) both as colorless lyophilizates, ISP-MS: 477.3 [M+H].

EXAMPLE 33

By the method of Example 32, 33.a

The mixture of epimers from Example 37.a.1 gave:
1. (S)-2-[(R)-2-(4-benzyloxy-3-methoxyphenyl)-2-(4-carbamimidoylphenylamino)acetylamino]-3-phenylpropionic acid acetate (1:1) and the mixture of epimers from Example 37.a gave
2. (S)-2-[(S)-2-(4-benzyloxy-3-methoxyphenyl)-2-(4-carbamimidoylphenylamino)acetylamino]-3-phenylpropionic acid acetate (1:1), ISP-MS: 553.3 [M+H], 33.b the product from Example 37.b gave, after chromatographic separation, the two epimers:
1. (S)-2-[(R)-2-(4-benzyloxy-3-methoxyphenyl)-2-(4-carbamimidoylphenylamino)acetylamino]-3-(4-hydroxy-phenyl)propionic acid acetate (1:2) and
2. (S)-2-[(S)-2-(4-benzyloxy-3-methoxyphenyl)-2-(4-carbamimidoylphenylamino)acetylamino]-3-(4-hydroxy-phenyl)propionic acid acetate (1:1), ISP-MS: 569.3 [M+H], 33.c the product from Example 37.c gave a mixture of (S)-1-[(R)- and -[(S)-(4-benzyloxy-3-methoxyphenyl)-(4-carbamimidoylphenylamino)acetyl]pyrrolidine 2-carboxylic acid acetate, ISP-MS: 503.3 [M+H], 33.d the product from Example 37.d gave (RS)-2-[2-(4-benzyloxy-3-methoxyphenyl)-2-(4-carbamimidoyl-phenylamino)acetylamino]-2-methylpropionic acid acetate (1:0.5), ISP-MS: 491.5 [M+H], 513.5 [M+Na], 33.e the product from Example 37.e gave, after chromatographic separation, the two epimers:
1. (S)-[[(R)-(4-benzyloxy-3-methoxyphenyl)-(4-carbamimidoylphenylamino)acetyl]methylamino]phenylacetic acid acetate (1:2) and
2. (S)-[[(S)-(4-benzyloxy-3-methoxyphenyl)-(4-carbamimidoylphenylamino)acetyl]methylamino]phenylacetic acid acetate (1:1), ISP-MS: 553.3 [M+H], 575.1 [M+Na], 33.f the product from Example 37.f gave the mixture of (RS)- and (SR)-1-[(RS)-(4-benzyloxy-3-methoxyphenyl)-(4-carbamimidoylphenylamino)acetyl]pyrrolidine-3-carboxylic acid, ISP-MS: 503.3 [M+H], 33.g the product from Example 37.g gave, after chromatographic separation, the two diastereomeric racemates of (RS)- or (SR)-2-[(RS)-(4-benzyloxy-3-methoxyphenyl)-(4-carbamimidoylphenylamino)acetyl]-1,2,3,4-tetrahydroisoquinoline-3-carboxylic acid acetate (1:1), ISP-MS: 565.3 [M+H], 587.2 [M+Na], 33.h the product from Example 37.h gave (RS)-1-[2-(4-benzyloxy-3-methoxyphenyl)-2-(4-carbamimidoyl-phenylamino)acetylamino]cyclopentanecarboxylic acid acetate (1:2),ISP-MS: 517.2 [M+H], 539.3 [M+Na], 33.i the product from Example 37.i gave (RS)-[2-(4-benzyloxy-3-methoxyphenyl)-2-(4-carbamimidoylphenylamino)acetylamino] diphenylacetic acid acetate (1:1), ISP-MS: 615.3 [M+H], 33.j the product from Example 37.j gave, after chromatographic separation, the two epimers:
1. (S)-2-[(R)-2-(4-benzyloxy-3-methoxyphenyl)-2-(4-carbamimidoylphenylamino)acetylamino]-4-tert-butoxycarbonylaminobutyric acid acetate (1:3) and
2. (S)-2-[(S)-2-(4-benzyloxy-3-methoxyphenyl)-2-(4-carbamimidoylphenylamino)acetylamino]-4-tert-butoxycarbonylaminobutyric acid acetate (1:3), ISP-MS: 606.1 [M+H], 628.2 [M+H], 33.k the product from Example 37.k gave, after chromatographic separation, the two epimers:
1. (S)-2-[(R)-2-(4-benzyloxy-3-methoxyphenyl)-2-(4-carbamimidoylphenylamino)acetylamino]-3-tert-butoxycarbonylaminopropionic acid acetate (1:1) and
2. (S)-2-[(S)-2-(4-benzyloxy-3-methoxyphenyl)-2-(4-carbamimidoylphenylamino)acetylamino]-3-tert-butoxycarbonylaminopropionic acid acetate (1:1), ISP-MS: 592.2 [M+H].

EXAMPLE 34

By the method of Example 32, 34.a the product from Example 38.a gave (RS)-2-[2-(4-benzyloxy-3-methoxyphenyl)-2-(4-carbamimidoylphenylamino)acetylamino]benzoic acid acetate (1:1), ISP-MS: 525.1 [M+H], 34.b the product from Example 38.b gave (RS)-3-[2-(4-benzyloxy-3-methoxyphenyl)-2-(4-carbamimidoylphenylamino)acetylamino]benzoic acid acetate (1:1), ISP-MS: 525.1 [M+H], 34.c the product from Example 38.c gave (RS)-4-[2-(4-benzyloxy-3-methoxyphenyl)-2-(4-carbamimidoylphenylamino)acetylamino]benzoic acid acetate (1:1), ISP-MS: 525.1 [M+H].

EXAMPLE 35

By the method of Example 32, the product from Example 39 gave a mixture of (RS)- and (SR)-3-[(RS)-2-(4- benzyloxy-3-methoxyphenyl)-2-(4-carbamimidoylphenylamino)acetylamino]-3-phenylpropionic acid.

EXAMPLE 36

36.1

335 mg of methyl L-alaninate hydrochloride, 1.03 ml of diisopropylethylamine and 1.06 g of (benzotriazol-1-yloxy)tris(dimethylamino)phosphonium hexafluorophosphate were added to a solution of 777 mg of the material prepared in Example 25 in 10 ml of DMF. The reaction solution was stirred at RT for 2 hours and subsequently concentrated under high vacuum. The residue was taken up in ethyl acetate and then washed with 10% strength KHCO$_3$ solution, with 2% strength citric acid, water and saturated NaCl solution. The organic phase was dried over MgSO$_4$ and concentrated under reduced pressure. The residue was purified by silica gel chromatography. This gave 823 mg (87%) of a 1:1 mixture of methyl (S)-2-[(R)- and -[(S)-2-(4-benzyloxy-3-methoxyphenyl)-2-(4-cyanophenylamino)acetylamino]propionate as a solid colorless foam. ISP-MS: 474.3 [M+H], 496.1 [M+Na], 512.2 [M+K].

36.2

8.4 ml of 1N LiOH solution were added to a solution, coded to 0° C., of 792 mg of the material which had been prepared according to Example 36.1 in 10 ml of THF. The mixture was stirred at 0° C. for 30 min and at RT for 2 hours. The THF was distilled off under reduced pressure. The aqueous solution that remained was acidified using 1N HCl, and a colorless precipitate formed. This was filtered off and dried under high vacuum. This gave 712 mg (91%) of a 1:1 mixture of (S)-2-[(R)- and -[(S)-2-(4-benzyloxy-3-methoxyphenyl)-2-(4-cyanophenylamino)acetylamino]propionic acid as a colorless solid. ISN-MS: 458.3 [M–H].

36.3

4.1 ml of triethylamine and then 683 mg of the material prepared according to Example 36.2 were added to a suspension of 1.04 g of hydroxylamine hydrochloride in 25 ml of EtOH. The reaction mixture was heated under reflux overnight and subsequently concentrated under reduced pressure. The residue was purified by silica gel chromatography (EtOAC/acetone/H$_2$O/HOAc 6:2:1:1). This gave 625 mg (86%) of a 1:1 mixture of (E)- and/or (Z)-(S)-2-[(R)- and -[(S)-2-(4-benzyloxy-3-methoxyphenyl)-2-[4-(N-hydroxycarbamimidoyl)phenylamino]acetylamino] propionic acid as a slightly pink lyophilizate. ISP-MS: 493.3 [M+H], 515.3 [M+Na].

EXAMPLE 37

By the method of Example 36, the material prepared in Example 25

37.a and methyl L-phenylalaninate hydrochloride gave a 1:1 mixture of methyl (S)-2-[(R)- and -[(S)-2-(4-benzyloxy-3-methoxyphenyl)-2-(4-cyanophenylamino)-acetylamino]-3-phenylpropionate which gave a 1:1 mixture of (S)-2-[(R)- and -[(S)-2-(4-benzyloxy-3-methoxyphenyl)-2-(4-cyanophenylamino)acetylamino]-3-phenylpropionic acid and from this, after chromatographic separation, the two products:

1. (E)- and/or (Z)-(S)-2-[(R)-2-(4-benzyloxy-3-methoxyphenyl)-2-[4-(N-hydroxycarbamimidoyl)phenylamino]acetylamino]-3-phenylpropionic acid and
2. (E)- and/or (Z)-(S)-2-[(S)-2-(4-benzyloxy-3-methoxyphenyl)-2-(4-(N-hydroxycarbamimidoyl)phenylamino]acetylamino]-3-phenylpropionic acid, 37.b and ethyl L-tyrosinate hydrochloride gave a 1:1 mixture of ethyl (S)-2-[(R)- and -[(S)-2-(4-benzyloxy-3-methoxyphenyl)-2-(4-cyanophenylamino)acetylamino]-3-(4-hydroxyphenyl)propionate which gave a 1:1 mixture of (S)-2-[(R)- and -[(S)-2-(4-benzyloxy-3-methoxyphenyl)-2-(4-cyanophenylamino)acetylamino]-3-(4-hydroxyphenyl)propionic acid which gave a 1:1 mixture of (E)- and/or (Z)-(S)-2-[(R)- and -[(S)-2-(4-benzyloxy-3-methoxyphenyl)-2-[4-(N-hydroxycarbamimidoyl)phenylamino]acetylamino]-3-(4-hydroxyphenyl)propionic acid, 37.c and methyl L-prolinate gave a 1:1 mixture of methyl (S)-1-[(R)- and -[(S)-(4-benzyloxy-3-methoxyphenyl)-(4-cyanophenylamino)acetyl]pyrrolidine-2-carboxylate which gave a mixture of (S)-1-[(R)- and [(S)-(4-benzyloxy-3-methoxyphenyl)-(4-cyanophenylamino)acetyl]pyrrolidine-2-carboxylic acid which gave a 1:1 mixture of (E)- and/or (Z)-(S)-1-[(R)- and -[(S)-(4-benzyloxy-3-methoxyphenyl)-[4-(N-hydroxycarbamimidoyl)phenylamino]acetyl]pyrrolidine-2-carboxylic acid, 37.d and methyl 2-aminoisobutyrate hydrochloride gave methyl (RS)-2-[2-(4-benzyloxy-3-methoxyphenyl)-2-(4-cyanophenylamino)acetylamino]-2-methylpropionate which gave (RS)-2-[2-(4-benzyloxy-3-methoxyphenyl)-2-(4-cyanophenylamino)acetylamino]-2-methylpropionic acid which gave (E)-and/or (Z)-(RS)-2-[2-(4-benzyloxy-3-methoxyphenyl)-2-[4-(N-hydroxycarbamimidoyl)phenylamino]acetylamino]-2-methylpropionic acid, 37.e and ethyl N-methyl-L-phenylglycinate hydrochloride gave a 1:1 mixture of ethyl (S)-[[(R)- and -[[(S)-(4-benzyloxy-3-methoxyphenyl)-(4-cyanophenylamino)acetyl]methylamino]phenyl acetate which gave a 1:1 mixture of (S)-[[(R)- and [[(S)-(4-benzyloxy-3-methoxyphenyl)-(4-cyanophenylamino)acetyl]methylamino]phenylacetic acid which gave a mixture of (E)- and/or (Z)-(S)-[[(R)- and -[[(S)-(4-benzyloxy-3-methoxyphenyl)-[4-(N-hydroxycarbamimidoyl)phenylamino]acetyl]methylamino]phenylacetic acid, 37.f and ethyl beta-D,L-prolinate hydrochloride gave a mixture of ethyl (RS)- and (SR)-1-[(RS)-(4-benzyloxy-3-methoxyphenyl)-(4-cyanophenylamino)acety] pyrrolidine-3-carboxylate which gave a mixture of (RS)- and (SR)-1-[(RS)-(4-benzyloxy-3-methoxyphenyl)-(4-cyanophenylamino)acetyl] pyrrolidine-3-carboxylic acid which gave a mixture of (E)- and/or (Z)-(RS)- and -(SR)-1-[(RS)-(4-benzyloxy-3-methoxyphenyl)-[4-(N-hydroxycarbamimidoyl)phenylamino]acetyl]pyrrolidine-3-carboxylic acid, 37.g and ethyl 1,2,3,4-tetrahydro-3-isoquinolinecarboxylate hydrochloride gave a mixture of ethyl (RS)- and (SR)-2-[(RS)-(4-benzyloxy-3-methoxyphenyl)-(4-cyanophenylamino)acetyl]-1,2,3,4-tetrahydroisoquinoline-3-carboxylate which gave a mixture of (RS)- and (SR)-2-[(RS)-(4-benzyloxy-3-methoxyphenyl)-(4-cyanophenylamino)acetyl]-1,2,3,4-tetrahydroisoquinoline-3-carboxylic acid which gave a mixture of (E)- and/or (Z)-(RS)- and -(SR)-2-[(RS)-

(4-benzyloxy-3-methoxyphenyl)-[4-(N-hydroxycarbamimidoyl)phenylamino]acetyl]-1,2,3,4-tetrahydroisoquinoline-3-carboxylic acid, 37.h
and ethyl 1-amino-1-cyclopentanecarboxylate hydrochloride gave ethyl (RS)-1-[2-(4-benzyloxy-3-methoxyphenyl)-2-(4-cyanophenylamino)acetylamino]cyclopentanecarboxylate which gave (RS)-1-[2-(4-benzyloxy-3-methoxyphenyl)-2-(4-cyanophenylamino)acetylamino]cyclopentanecarboxylic acid which gave (E)- and/or (Z)-(RS)-1-[2-(4-benzyloxy-3-methoxyphenyl)-2-(4-(N-hydroxycarbamimidoyl)phenylamino]acetylamino]cyclopentanecarboxylic acid, 37.i
and methyl α,α-diphenylglycinate hydrochloride gave methyl (RS)-[2-(4-benzyloxy-3-methoxyphenyl)-2-(4-cyanophenylamino)acetylamino]diphenylacetate which gave (RS)-[2-(4-benzyloxy-3-methoxyphenyl)-2-(4-cyanophenylamino)acetylamino]diphenylacetic acid which gave (E)- and/or (Z)-(RS)-[2-(4-benzyloxy-3-methoxyphenyl)-2-[4-(N-hydroxycarbamimidoyl)phenylamino]acetylamino]diphenylacetic acid, 37.j
and methyl N-γ-Boc-L-α,γ-diaminobutyrate hydrochloride gave a 1:1 mixture of methyl (S)-2-[(R)- and -[(S)-2-(4-benzyloxy-3-methoxyphenyl)-2-(4-cyanophenylamino)acetylamino]-4-tert-butoxycarbonylaminobutyrate which gave a 1:1 mixture of (S)-2-[(R)- and -[(S)-2-(4-benzyloxy-3-methoxyphenyl)-2-(4-cyanophenylamino)acetylamino]-4-tert-butoxycarbonylaminobutyric acid which gave a 1:1 mixture of (S)-2-[(R)- and -[(S)-2-(4-benzyloxy-3-methoxyphenyl)-2-[4-[(E)- and/or -[(Z)-N-hydroxycarbamimidoyl]phenylamino]acetylamino]-4-tertbutoxycarbonylaminobutyric acid, 37.k
and methyl N-β-Boc-L-α,β-diaminopropionate hydrochloride gave a 1:1 mixture of methyl (S)-2-[(R)- and -[(S)-2-(4-benzyloxy-3-methoxyphenyl)-2-(4-cyanophenylamino)acetylamino]-3-tert-butoxycarbonylaminopropionate which gave a 1:1 mixture of (S)-2-[(R)- and -[(S)-2-(4-benzyloxy-3-methoxyphenyl)-2-(4-cyanophenylamino)acetylamino]-3-tert-butoxycarbonylaminopropionic acid which gave a 1:1 mixture of (S)-2-[(R)- and -[(S)-2-(4-benzyloxy-3-methoxyphenyl)-2-[4-[(E)- and/or -[(Z)-N-hydroxycarbamimidoyl]phenylamino]acetylamino]-3-tertbutoxycarbonylaminopropionic acid.

EXAMPLE 38

By the method of Example 36, the material prepared in Example 25

38.a
and ethyl 2-aminobenzoate gave ethyl (RS)-2-[2-(4-benzyloxy-3-methoxyphenyl)-2-(4-cyanophenylamino)acetylamino]benzoate which gave (RS)-2-[2-(4-benzyloxy-3-methoxyphenyl)-2-(4-cyanophenylamino)acetylamino]benzoic acid which gave (E)- and/or (Z)-(RS)-2-[2-(4-benzyloxy-3-methoxyphenyl)-2-[4-(N-hydroxycarbamimi-doyl)phenylamino]acetylamino]benzoic acid, 38.b
and ethyl 3-aminobenzoate gave ethyl (RS)-3-[2-(4-benzyloxy-3-methoxyphenyl)-2-(4-cyanophenylamino)acetylamino]benzoate which gave (RS)-3-[2-(4-benzyloxy-3-methoxyphenyl)-2-(4-cyanophenylamino)acetylamino]benzoic acid which gave (E)- and/or (Z)-(RS)-3-[2-(4-benzyloxy-3-methoxyphenyl)-2-[4-(N-hydroxycarbamimi-doyl)phenylamino]acetylamino]benzoic acid, 38.c
and ethyl 4-aminobenzoate gave ethyl (RS)-4-[2-(4-benzyloxy-3-methoxyphenyl)-2-(4-cyanophenylamino)acetylamino]benzoate which gave (RS)-4-[2-(4-benzyloxy-3-methoxyphenyl)-2-(4-cyanophenylamino)acetylamino]benzoic acid which gave (E)- and/or (Z)-(RS)-4-[2-(4-benzyloxy-3-methoxyphenyl)-2-[4-(N-hydroxycarbamimidoyl)phenylamino]acetylamino]benzoic acid.

EXAMPLE 39

By the method of Example 36, the material prepared in Example 25 and methyl D,L-3-amino-3-phenylpropionate hydrochloride gave the mixtures of the diastereomers of the corresponding nitrile esters which gave the corresponding nitrile acids and finally a mixture of (E)- and/or (Z)-(RS)- and -(SR)-3-[(RS)-2-(4-benzyloxy-3-methoxyphenyl)-2-[4-(N-hydroxycarb-amimidoyl)phenylamino]acetylamino]-3-phenylpropionic acid.

EXAMPLE 40

40.a
A suspension of 107 mg of the mixture of epimers obtained according to Example 33.j in 3 ml of CH$_2$Cl$_2$ was admixed with 0.5 ml of trifluoroacetic acid and stirred at RT for 1 hour. The reaction mixture was concentrated. The residue was purified by silica gel chromatography (EtOAc/acetone/H$_2$O/HOAc 6:2:2:4). This gave 79 mg (85%) of a mixture of (S)-4-amino-2-[(R)- and -[(S)-2-(4-benzyloxy-3-methoxyphenyl)-2-(4-carbam-imidoylphenylamino)acetylamino]butyric acid acetate (1:1) as a beige lyophilizate.

40.b
By the method of Example 40.a, the mixture of epimers obtained according to Example 33.k gave a 1:1 mixture of (S)-3-amino-2-[(R)- and -[(S)-2-(4-benzyloxy-3-methoxyphenyl)-2-(4-carbamimidoylphenylamino)acetylamino]propionic acid acetate (1:1) in a yield of 44% as a beige lyophilizate.

EXAMPLE 41

41.a
By the method of Example 32 and via (E)- and/or (Z)-(S)-[(R)- or -[(S)-2-(4-benzyloxy-3-methoxyphenyl)-2-[4-(N-hydroxycarbamimidoyl)phenylamino]acetylamino]phenylacetic acid, the following compounds were obtained:

a) (S)-[(R)-2-(4-benzyloxy-3-methoxyphenyl)-2-(4-carbamimidoylphenylamino)acetylamino]phenylacetic acid and b) (S)-[(S)-2-(4-benzyloxy-3-methoxyphenyl)-2-(4-carbamimidoylphenylamino)acetylamino]phenylacetic acid.

41.b
The amidoxime used in 41.a was prepared by the method of Example 37 starting from material obtained according to Example 25 and methyl (S)-phenylglycinate via the corresponding nitrile esters and the corresponding nitrile acids prepared therefrom.

EXAMPLE 42

42.a

By the method of Example 41, but using methyl (R)-phenylglycinate hydrochloride instead of methyl (S)-phenylglycinate hydrochloride, the two epimers 1. (R)-[(R)-2-(4-benzyloxy-3-methoxyphenyl)-2-(4-carbamimidoylphenylamino)acetylamino]phenylacetic acid and
2. (R)-[(S)-2-(4-benzyloxy-3-methoxyphenyl)-2-(4-carbamimidoylphenylamino)acetylamino]phenylacetic acid are obtained.

42.b

By the method of Example 41, but using ethyl p-amino-L-phenylalaninate dihydrochloride instead of methyl (S)-phenylglycinate hydrochloride, a 1:1 mixture of ethyl (S)-3-(4-aminophenyl)-2-[(R)- and -[(S)-2-(4-benzyloxy-3-methoxyphenyl)-2-(4-cyanophenylamino)acetylamino] propionate are obtained, which gaves 1. a 1:1 mixture of ethyl (E)- and/or (Z)-(S)-3-(4-aminophenyl)-2-[(R)- and -[(S)-2-(4-benzyloxy-3-methoxyphenyl)-2-[4-(N-hydroxycarbamimidoyl)phenylamino]acetylamino]propionate which gaves
2. a 1:1 mixture of ethyl (S)-3-(4-aminophenyl)-2-[(R)- and -[(S)-2-(4-benzyloxy-3-methoxyphenyl)-2-(4-carbam-imidoylphenylamino)acetylamino]propionate acetate (1:1) which finally gaves, after chromatographic separation,
3. (S)-3-(4-aminophenyl)-2-[(R)-2-(4-benzyloxy-3-methoxyphenyl)-2-(4-carbamimidoylphenylamino) acetylamino]propionic acid acetate (1:3) and
4. (S)-3-(4-aminophenyl)-2-[(S)-2-(4-benzyloxy-3-methoxyphenyl)-2-(4-carbamimidoylphenylamino)-acetylamino]propionic acid acetate (1:3), ISP-MS: 568.3 [M+H], 590.3 [M+Na].

EXAMPLE 43

43.1

By the method of Example 26, 3,5-dimethoxybenzaldehyde, 4-aminobenzonitrile and benzylisonitrile gave methyl (RS)-(4-cyanophenylamino)-(3,5-dimethoxyphenyl)acetate.

43.2

By the method of Example 25, the product prepared under 43.1 gave (RS)-(4-cyanophenylamino)-(3,5-dimethoxyphenyl)acetic acid.

43.3

By the method of Example 41, the acid prepared under 43.2 and methyl (S)-phenylglycinate hydrochloride gave, after chromatographic separation of the mixture of epimers, the two products a) (S)-[(R)-2-(4-carbamimidoylphenylamino)-2-(3,5-dimethoxyphenyl)acetylamino]phenylacetic acid acetate (1:1.6) and
b) (S)-[(S)-2-(4-carbamimidoylphenylamino)-2-(3,5-dimethoxyphenyl)acetylamino]phenylacetic acid acetate (1:1.75), ISP-MS: 463.2 [M+H].

EXAMPLE 44

By the method of Example 26, 3,4-diethoxybenzaldehyde, 4-aminobenzonitrile and benzylisonitrile gave (RS)-(4-cyanophenylamino)-(3,4-diethoxyphenyl)acetic acid.

EXAMPLE 45

A degassed solution of 147 mg of the product from Example 47.b in 5 ml of EtOH, 5 ml of THF, 2 ml of H$_2$O and 1 ml of HOAc was admixed with a spatula tip of Raney nickel and hydrogenated for 5 hours. The catalyst was filtered off. The filtrate was concentrated. The residue was purified by silica gel chromatography (EtOAc/acetone/H$_2$O/HOAc 6:2:1:1). This gave 80 mg (56%) of (RS)-2-(4-benzyloxy-3-methoxyphenyl)-2-(4-carbamimidoylphenylamino)-N-[2-(3,4-dihydroxyphenyl)ethyl] acetamide acetate (1:1) as a colorless lyophilizate. ISP-MS: 541.2 [M+H].

EXAMPLE 46

Using the method of Example 45

46.a the product from Example 48.a gave (RS)-N-benzyl-2-(4-benzyloxy-3-methoxyphenyl)-2-(4-carbamimidoylphenylamino)-N-methylacetamide, ISP-MS: 509.5 [M+H], 46.b the product from Example 48.b gave (RS)-2-(4-benzyloxy-3-methoxyphenyl)-2-(4-carbamimidoylphenylamino)-N-[2-(4-sulphamoylphenyl)ethyl]acetamide, ISP-MS: 588.4 [M+H], 46.c the product from Example 48.c gave (RS)-2-(4-benzyloxy-3-methoxyphenyl)-2-(4-carbamimidoylphenylamino)-N-(2-pyridin-2-ylethyl) acetamide acetate (1:1), ISP-MS: 510.3 [M+H], 46.d the product from Example 48.d gave (RS)-N-[2-(4-aminophenyl)ethyl]-2-(4-benzyloxy-3-methoxyphenyl)-2-(4-carbamimidoylphenylamino) acetamide acetate (1:1), ISP-MS: 523.4 [M+H], 46.e 1. the diastereomer from Example 48.e.1 gave the corresponding (R)-2-(4-benzyloxy-3-methoxyphenyl)-2-(4-carbamimidoylphenylamino)-N-[(R)-2-hydroxy-1-phenyl-ethy]acetamide acetate (1:1) and
2. the diastereomer from Example 48.e.2 gave the corresponding (S)-2-(4-benzyloxy-3-methoxyphenyl)-2-(4-carbamimidoylphenylamino)-N-[(R)-2-hydroxy-1-phenylethyl]acetamide acetate (1:1), ISP-MS: 525.2 [M+H], 46.f 1. the diastereomer from Example 48.f.1 gave the corresponding (R)-2-(4-benzyloxy-3-methoxyphenyl)-2-(4-carbamimidoylpheny]amino)-N-[(S)-2-hydroxy-1-phenylethyl]acetamide acetate (1:1) and
2. the diastereomer from Example 48.f.2 gave the corresponding (S)-2-(4-benzyloxy-3-methoxyphenyl)-2-(4-carbamimidoylphenylamino)-N-[(S)-2-hydroxy-1-phenylethyl]acetamide acetate (1:1), ISP-MS: 525.4 [M+H], 46.g 1. the diastereomer from Example 48.g.1 gave the corresponding (R)-2-(4-benzyloxy-3-methoxyphenyl)-2-(4-carbamimidoylphenylamino)-N-[(R)-1-phenylethyl] acetamide acetate (1:1) and
2. the diastereomer from Example 48.g.2 gave the corresponding (S)-2-(4-benzyloxy-3-methoxyphenyl)-2-(4-carbamimidoylphenylamino)-N-[(R)-1-phenylethyl] acetamide acetate (1:1), ISP-MS: 509.4 [M+H], 46.h 1. the diastereomer from Example 48.h.1 gave the corresponding (R)-2-(4-benzyloxy-3-methoxyphenyl)-2-(4- carbamimidoylphenylamino)-N-[(S)-1-phenylethyl] acetamide acetate (1:1) and 2. the diastereomer from Example 48.h.2 gave the corresponding (S)-2-(4-benzyloxy-3-methoxyphenyl)-2-(4-carbamimidoylphenylamino)-N-[(S)-1-phenylethyl] acetamide acetate (1:1), ISP-MS: 509.4 [M+H].

EXAMPLE 47

47.a

By the method of Example 36.1, 388 mg of the product from Example 25 and 184 mg of 3-hydroxythyramine gave 323 mg (62%) of (RS)-2-(4-benzyloxy-3-methoxyphenyl)-2-(4-cyanophenylamino)-N-[2-(3,4-dihydroxyphenyl)ethyl] acetamide as a solid colorless foam. ISN-MS: 522.1 [M–H].

47.b

By the method of Example 36.3, 258 mg of the product obtained according to Example 47.a gave 222 mg (81%) of (RS)-2-(4-benzyloxy-3-methoxyphenyl)-2-(4-cyanophenylamino)-N-[2-(3,4-dihydroxyphenyl)ethyl]-acetamide as a colorless powder. ISP-MS: 557.2 [M+H].

EXAMPLE 48

By the method of the process described in Examples 36.1 and 36.3, the following compounds were prepared:

From the product of Example 25:

48.a and N-benzylmethylamine, via the intermediate (RS)-N-benzyl-2-(4-benzyloxy-3-methoxyphenyl)-2-(4-cyanophenylamino)-N-methylacetamide, (E)- and/or (Z)-(RS)-N-benzyl-2-(4-benzyloxy-3-methoxyphenyl)-2-[4-(N-hydroxycarbamimidoyl) phenylamino]-N-methylacetamide, 48.b and 4-(2-aminoethyl)benzenesulphonamide, via the intermediate (RS)-2-(4-benzyloxy-3-methoxyphenyl)-2-(4-cyanophenylamino)-N-[2-(4-sulphamoylphenyl)ethyl] acetamide, (E)- and/or (Z)-(RS)-2-(4-benzyloxy-3-methoxyphenyl)-2-[4-(N-hydroxycarbamimidoyl) phenylamino]-N-[2-(4-sulphamoylphenyl)ethyl] acetamide, 48.c and 2-(2-aminoethyl)pyridine, via the intermediate (RS)-2-(4-benzyloxy-3-ethoxyphenyl)-2-(4-cyanophenylamino)-N-(2-pyridin-2-ylethyl)acetamide, (E)- and/or (Z)-(RS)-2-(4-benzyloxy-3-methoxyphenyl)-2-[4-(N-hydroxycarbamimidoyl)-phenylamino]-N-(2-pyridin-2-ylethyl)acetamide, 48.d and 4-nitrophenethylamine, via the intermediate (RS)-2-(4-benzyloxy-3-methoxyphenyl)-2-(4-cyanophenylamino)-N-[2-(4-nitrophenyl)ethyl] acetamide, (E)- and/or (Z)-(RS)-2-(4-benzyloxy-3-methoxyphenyl)-2-[4-(N-hydroxycarbamimidoyl)-phenylamino]-N-[2-(4-nitrophenyl)ethyl]acetamide, 48.e and (R)-phenylglycinol, after chromatographic separation, the two diastereomers (R)-2-(4-benzyloxy-3-methoxyphenyl)-2-(4-cyanophenylamino)-N-[(R)-2-hydroxy-1-phenylethyl]acetamide and (S)-2-(4-benzyloxy-3-methoxyphenyl)-2-(4-cyanophenylamino)-N-[(R)-2-hydroxy-1-phenylethyl] acetamide;

1. the first diastereomer gave (E)- and/or (Z)-(R)-2-(4-benzyloxy-3-methoxyphenyl)-2-[4-(N-hydroxycarbamimidoyl)phenylamino]-N-[(R)-2-hydroxy-1-phenylethyl]acetamide, and 2. the second diastereomer gave (E)- and/or (Z)-(S)-2-(4-benzyloxy-3-methoxyphenyl)-2-[4-(N-hydroxycarbamimidoyl)phenylamino]-N-[(R)-2-hydroxy-1-phenylethyl]acetamide, 48.f and (S)-phenylglycinol, after chromatographic separation, the two diastereomers (R)-2-(4-benzyloxy-3-methoxyphenyl)-2-(4-cyanophenylamino)-N-[(S)-2-hydroxy-1-phenylethyl]acetamide and (S)-2-(4-benzyloxy-3-methoxyphenyl)-2-(4-cyanophenylamino)-N-[(S)-2-hydroxy-1-phenylethyl] acetamide;

1. the first diastereomer gave (E)- and/or (Z)-(R)-2-(4-benzyloxy-3-methoxyphenyl)-2-[4-(N-hydroxycarbamimidoyl)phenylamino]-N-[(S)-2-hydroxy-1-phenylethyl]acetamide and 2. the second diastereomer gave (E)- and/or (Z)-(S)-2-(4-benzyloxy-3-methoxyphenyl)-2-[4-(N-hydroxycarbamimidoyl)phenylamino]-N-[(S)-2-hydroxy-1-phenylethyl]acetamide, 48.g and (R)-1-phenylethylamine, after chromato-graphic separation, the two diastereomers 1. (E)- and/or (Z)-(R)-2-(4-benzyloxy-3-methoxyphenyl)-2-[4-(N-hydroxycarbamimidoyl)phenylamino]-N-[(R)-1-phenylethyl]acetamide and 2. (E)- and/or (Z)-(S)-2-(4-benzyloxy-3-methoxyphenyl)-2-[4-(N-hydroxycarbamimidoyl)phenylamino]-N-[(R)-1-phenylethyl]acetamide, 48.h and (S)-1-phenylethylamine, after chromato-graphic separation, the two diastereomers (R)-2-(4-benzyloxy-3-methoxyphenyl)-2-(4-cyanophenylamino)-N-[(S)-1-phenylethyl)acetamide and (S)-2-(4-benzyloxy-3-methoxyphenyl)-2-(4-cyanophenylamino)-N-[(S)-1-phenylethyl)acetamide;

1. the first diastereomer gave (E)- and/or (Z)-(R)-2-(4-benzyloxy-3-methoxyphenyl)-2-[4-(N-hydroxycarbamimidoyl)phenylamino]-N-[(S)-1-phenylethyl]-acetamide, 2. the second diastereomer gave (E)- and/or (Z)-(S)-2-(4-benzyloxy-3-methoxyphenyl)-2-[4-(N-hydroxycarbamimidoyl)phenylamino]-N-[(S)-1-phenylethyl]acetamide.

EXAMPLE 49

By the method of Example 45

49.a the product from Example 50.2 gave (RS)-N-[2-[benzylcarbamoyl-(4-carbamimidoylphenylamino) methyl]-5-benzyloxy-4-methoxyphenyl]benzamide acetate (1:1.5) as a colorless solid, 49.b the product from Example 51.a gave methyl (RS)-[2-[benzylcarbamoyl-(4-carbamimidoylphenylamino) methyl]-5-benzyloxy-4-methoxyphenyl]carbamate acetate (1:1.3) as a colorless solid, 49.c the product from Example 51.b gave (RS)-2-(2-acetylamino-4-benzyloxy-5-methoxyphenyl)-N-benzyl-2-(4-carbamimidoylphenylamino)acetamide acetate (1:1) as a colorless solid, 49.d the product from Example 51.c gave (RS)-N-benzyl-2-(4-benzyloxy-5-methoxy-2- phenylacetylaminophenyl)-2-(4-carbamimidoylphenylamino)acetamide acetate (1:1) as a slightly brown solid, 49.e the product from Example 52.3 gave (RS)-N-benzyl-2-(4-carbamimidoylphenylamino)-2-(4,5-dimethoxy-2-phenylacetylaminophenyl)acetamide acetate (1:1) as a colorless solid, 49.f the product from Example 53.a gave methyl (RS)-[2-[benzylcarbamoyl-(4-carbamimidoylphenylamino)methyl]-4,5-dimethoxyphenyl]carbamate acetate (1:1) as a slightly brown solid, 49.g the product from Example 53.b gave (RS)-N-[2-[benzylcarbamoyl-(4-carbamimidoylphenylamino)methyl]-4,5-dimethoxyphenyl]benzamide acetate (1:1) as a colorless solid, ISP-MS: 588.3 [M+H], 49.h the product from Example 54.3 gave (RS)-N-[2-[benzylcarbamoyl-(4-carbamimidoylphenylamino)methyl]-4-methoxyphenyl]benzamide acetate (1:1) as a colorless lyophilizate, ISP-MS: 508.3 [M+H], 49.i the product from Example 55 gave (RS)-2-(2-benzenesulphonylamino-5-methoxyphenyl)-N-benzyl-2-(4-carbamimidoylphenylamino)acetamide acetate (1:1) as a colorless lyophilizate, ISP-MS: 544.1 [M+H].

EXAMPLE 50

50.1

0.26 ml of diisopropylethylamine and 0.08 ml of benzoyl chloride were added to a solution of 300 mg of the nitrile obtained according to Example 27 in 10 ml of THF. The reaction solution was stirred at RT for 3 hours. The THF was subsequently distilled off under reduced pressure. The residue was taken up in $CH_2Cl_2$ and washed with saturated NaCl solution. The organic phase was dried over $Na_2SO_4$, filtered and concentrated under reduced pressure. The residue was crystallized from cyclohexane/toluene/acetone. This gave 288 mg (79%) of (RS)-N-{2-[benzylcarbamoyl-(4-cyanophenylamino)methyl]-5-benzyloxy-4-methoxyphenyl}benzamide as a slightly brown solid.

50.2

By the method of Example 36.3, 280 mg of the material prepared above gave 254 mg (86%) of (RS)-N-(2-{benzylcarbamoyl-[4-(N-hydroxycarbamimidoyl)phenylamino]methyl}-5-benzyloxy-4-methoxyphenyl)benzamide as a slightly brown solid.

EXAMPLE 51

By the method of Example 50.1, the product from Example 27 and 51.a methyl chloroformate gave methyl (RS)-(2-{benzylcarbamoyl-[4-(N-hydroxycarbamimidoyl)phenylamino]methyl}-5-benzyloxy-4-methoxyphenyl)carbamate, 51.b acetyl chloride gave (E)- and/or (Z)-(RS)-2-(2-acetylamino-4-benzyloxy-5-methoxyphenyl)-N-benzyl-2-[4-(N-hydroxycarbamimidoyl)phenylamino]acetamide, 51.c phenylacetyl chloride gave (E)- and/or (Z)-(RS)-N-benzyl-2-(4-benzyloxy-5-methoxy-2-phenylacetylaminophenyl)-2-[4-(N-hydroxycarbamimidoyl)phenylamino]-acetamide.

EXAMPLE 52

52.1

By the method of Example 16 and starting from 6-nitroveratraldehyde, 4-aminobenzonitrile and benzylisonitrile, (RS)-N-benzyl-2-(4-cyanophenylamino)-2-(4,5-dimethoxy-2-nitrophenyl)acetamide was obtained in a yield of 10% as yellow crystals.

52.2

By the method of Example 27, the nitro compound prepared in 52.1 gave (RS)-2-(2-amino-4,5-dimethoxyphenyl)-N-benzyl-2-(4-cyanophenylamino)acetamide in a yield of 25%. Slightly grey crystals.

52.3

By the method of Example 50, the aniline compound prepared above and phenylacetyl chloride gave (E)- and/or (Z)-(RS)-N-benzyl-2-(4,5-dimethoxy-2-phenylacetylaminophenyl)-2-[4-(N-hydroxycarbamimidoyl)phenylamino]acetamide.

EXAMPLE 53

By the method of Example 50, the aniline compound prepared in 52.2 and:

53.a methyl chloroformate gave methyl (E)- and/or (Z)-(RS)-[2-[benzylcarbamoyl-[4-(N-hydroxycarbamimi-doyl)phenylamino]methyl]-4,5-dimethoxyphenyl]carbamate, 53.b benzoyl chloride gave (E)- and/or (Z)-(RS)-N-[2-[benzylcarbamoyl-[4-(N-hydroxycarbamimidoyl)phenylamino]methyl]-4,5-dimethoxyphenyl)benzamide.

EXAMPLE 54

54.1

By the method of Example 16 and starting from 6-nitroveratraldehyde, 4-aminobenzonitrile and benzylisonitrile, (RS)-N-benzyl-2-(4-cyanophenylamino)-2-(5-methoxy-2-nitrophenyl)acetamide is obtained in a yield of 24%. Yellow crystals.

54.2

By the method of Example 27, the nitro compound prepared above gave (RS)-N-benzyl-2-(4-cyanophenylamino)-2-(2-amino-5-methoxyphenyl)acetamide in a yield of 79%. ISP-MS: 387.1 [M+H], 409.2 [M+Na].

54.3

By the method of Example 50, the nitrile obtained in Example 54.2 and benzoyl chloride gave (E)- and/or (Z)-(RS)-N-[2-[benzylcarbamoyl-[4-(N-hydroxycarbamimidoyl)phenylamino]methyl]-4-methoxyphenyl]benzamide.

EXAMPLE 55

By the method of Example 50, the nitrile obtained in Example 54.2 and phenylsulphonyl chloride gave (E)- and/or (Z)-(RS)-2-(2-benzenesulphonylamino-5-methoxyphenyl)-N-benzyl-2-[4-(N-hydroxycarbamimidoyl)phenylamino]acetamide.

EXAMPLE 56

56.1

By the method of Example 36.1, the material obtained according to Example 27 and methoxyacetic acid gave (RS)-N-benzyl-2-[4-benzyloxy-5-methoxy-2-(2-methoxyacetylamino)phenyl]-2-(4-cyanophenylamino) acetamide in a yield of 66%. Solid.

56.2

By the method of Example 36.3, the nitrile prepared in Example 56.1 was reacted in a yield of 81% to gave (RS)-N-benzyl-2-[4-benzyloxy-5-methoxy-2-(2-methoxyacetylamino)phenyl]-2-[4-(N-hydroxycarbamimidoyl)phenylamino]acetamide. Slightly brown solid.

56.3

By the method of Example 45, the amidoxime obtained in Example 56.2 was reduced to (RS)-N-benzyl-2-[4-benzyloxy-5-methoxy-2-(2-methoxyacetylamino)-phenyl]-2-(4-carbamimidoylphenylamino)acetamide hydrochloride (1:2).

EXAMPLE 57

57.1

By the method of Example 36.1, the product from Example 27 and N-Boc-glycine gave tert-butyl (RS)-{(2[-benzylcarbamoyl-(4-cyanophenylamino)methyl]-5-benzyloxy-4-methoxyphenylcarbamoyl}methyl)carbamate in a yield of 65%.

57.2

The product obtained above was reacted by the method of Example 36.3 to gave tert-butyl (RS)-[(2-{benzylcarbamoyl-[4-(N-hydroxycarbamimidoyl) phenylamino]methyl}-5-benzyloxy-4-methoxyphenylcarbamoyl)methyl]carbamate in a yield of 65%. Slightly brown solid.

57.3

A solution of 170 mg of the amidoxime obtained according to Example 57.2 in 10 ml of EtOH was admixed with a spatula tip of Raney nickel and a few drops of acetic acid. The mixture was then hydrogenated for 2 hours and subsequently filtered off from the catalyst. The filtrate was concentrated. The residue was purified by silica gel chromatography (EtOAc/acetone/$H_2O$/HOAc 6:2:1:1). The product fractions were concentrated. The residue was dissolved in $CH_2Cl_2$, admixed with 5 ml of trifluoroacetic acid and stirred at 0° C. for 3 hours. The mixture was then concentrated under reduced pressure. The residue was crystallized from $Et_2O$. This gave 107 mg (76%) of (RS)-2-[2-(2-aminoacetylamino)-4-benzyloxy-5-methoxyphenyl]-N-benzyl-2-(4-carbamimidoylphenylamino)acetamide trifluoroacetate (1:2) as a slightly brown solid.

EXAMPLE 58

By the method of Example 45:

58.a
the product obtained in Example 59.5 gave (RS)-3-[2-[benzylcarbamoyl-( 4-carbamimidoylphenylamino) methyl]-4,5-dimethoxyphenoxymethyl]benzoic acid acetate (1:1), ISP-MS: 569.3 [M+H], 58.b
the product obtained in Example 60.a gave (RS)-[2-[benzylcarbamoyl-(4-carbamimidoylphenylamino) methyl]-4,5-dimethoxyphenoxy]acetic acid acetate (1:1), 58.c
the product obtained in Example 60.b gave (RS)-4-[2-[benzylcarbamoyl-(4-carbamimidoylphenylamino) methyl]-4,5-dimethoxyphenoxymethyl]benzoic acid acetate (1:1), ISP-MS: 569.3 [M+H], 58.d
the product obtained in Example 60.c gave (RS)-4-[2-[benzylcarbamoyl-(4-carbamimidoylphenylamino) methyl]-4,5-dimethoxyphenoxy]butyric acid, 58.e
the product obtained in Example 61 gave (RS)-[2-[benzylcarbamoyl-(4-carbamimidoylphenylamino) methyl]-4-methoxyphenoxy]acetic acid, ISP-MS: M+H [463.2], 58.f
the product obtained in Example 62 gave (RS)-[2-[benzylcarbamoyl-(4-carbamimidoylphenylamino) methyl]-4,6-dimethylphenoxy]acetic acid acetate (1:0.5), ISP-MS: 461.3 [M+H], 483.4 [M+Na].

EXAMPLE 59

59.1

1.18 g of 4-aminobenzonitrile and 1.22 ml of benzylisonitrile were added to a solution of 2.78 mg of 2-benzyloxy-4,5-dimethoxybenzaldehyde in 36 ml of THF and 4 ml of $H_2O$. The mixture was stirred at RT for 5 min and then admixed with 2.85 g of p-toluenesulphonic acid. The reaction solution was stirred at RT for 24 hours and then concentrated under reduced pressure. The residue was taken up in $CH_2Cl_2$ and then washed with saturated $NaHCO_3$ solution and saturated NaCl solution. The organic phase was dried over $Na_2SO_4$, filtered off and concentrated under reduced pressure. The residue was purified by silica gel chromatography (toluene/acetone 9:1). This gave 2.13 g (42%) of (RS)-N-benzyl-2-(2-benzyloxy-4,5-dimethoxyphenyl)-2-(4-cyanophenylamino)acetamide as a light-yellow solid.

59.2

A solution of 1.4 g of the material obtained in 59.1 in 140 ml of EtOH was admixed with 420 mg of Pd/C 10% and hydrogenated for 5 hours, during which a colorless precipitate formed. This was redissolved by addition of 75 ml of dioxane. The catalyst was subsequently removed by filtration. The filtrate was concentrated under reduced pressure. The residue was crystallized from EtOH. This gave 907 mg (79%) of (RS)-N-benzyl-2-(4-cyanophenylamino)-2-(2-hydroxy-4,5-dimethoxyphenyl)acetamide as colorless crystals.

59.3

A solution of 418 mg of the material obtained in 59.2 in 30 ml of acetone was admixed with 415 mg of $K_2CO_3$ and 252 mg of methyl 3-bromomethylbenzoate. The reaction mixture was heated under reflux for 3 hours and subsequently filtered. The filtrate was concentrated. The residue was taken up in $CH_2Cl_2$ and washed with $H_2O$. The organic phase was dried over $Na_2SO_4$, filtered and concentrated under reduced pressure. The residue was purified by silica gel chromatography (EtOAc/hexane 2:3). This gave 365 mg (65%) of methyl (RS)-3-[2-[benzylcarbamoyl-(4-cyanophenylamino)methyl]-4,5-dimethoxyphenoxymethyl] benzoate as a colorless solid.

59.4

By the method of Example 36.2, the material obtained in 59.3 gave (RS)-3-[2-[benzylcarbamoyl-(4-cyanophenylamino)methyl]-4,5-dimethoxyphenoxymethyl] benzoic acid in quantitative yield. Colorless solid.

59.5

By the method of Example 36.3, the material obtained according to 59.4 gave (E)- and/or (Z)-(RS)-3-[2-[benzylcarbamoyl-[4-(N-hydroxycarbamimidoyl)

phenylamino]methyl]-4,5-dimethoxyphenoxymethyl] benzoic acid in a yield of 70%. Colorless solid.

EXAMPLE 60

By the methods of Examples 59.3–59.5, the material obtained according to Example 59.2 and 60.a
  ethyl bromoacetate gave, via the nitriles ethyl (RS)-[2-[benzylcarbamoyl-(4-cyanophenylamino)methyl]-4,5-dimethoxyphenoxy]acetate and (RS)-[2-[benzylcarbamoyl-(4-cyanophenylamino)methyl]-4,5-dimethoxyphenoxy]acetic acid, (E)- and/or (Z)-(RS)-[2-[benzylcarbamoyl-[4-(N-hydroxycarbamimidoyl) phenylamino]methyl]-4,5-dimethoxyphenoxy]acetic acid, 60.b
  methyl 4-bromomethylbenzoate gave, via the nitriles methyl (RS)-4-[2-[benzylcarbamoyl-(4-cyanophenylamino)methyl]-4,5-dimethoxyphenoxymethyl]benzoate and (RS)-4-[2-[benzylcarbamoyl-(4-cyanophenylamino)methyl]-4,5-dimethoxyphenoxymethyl]benzoic acid, (E)- and/or (Z)-(RS)-4-[2-[benzylcarbamoyl-[4-(N-hydroxycarbamimidoyl)phenylamino]methyl]-4,5-dimethoxyphenoxymethyl]benzoic acid, 60.c
  ethyl 4-bromobutyrate gave, via the nitriles ethyl (RS)-4-(2-[benzylcarbamoyl-(4-cyanophenylamino) methyl]-4,5-dimethoxyphenoxy]butyrate and (RS)-4-[2-[benzylcarbamoyl-(4-cyanophenylamino)methyl]-4,5-dimethoxyphenoxy]butyric acid, (E)- and/or (Z)-(RS)-4-[2-[benzylcarbamoyl-[4-(N-hydroxycarbamimidoyl)phenylamino]methyl]-4,5-dimethoxyphenoxy]butyric acid.

EXAMPLE 61

By the method of Example 60, (RS)-N-benzyl-2-(4-cyanophenylamino)-2-(2-hydroxy-5-methoxyphenyl) acetamide and ethyl bromoacetate gave, via the nitriles ethyl (RS)-[2-[benzylcarbamoyl-(4-cyanophenylamino)methyl]-4-methoxyphenoxy]acetate and (RS)-[2-[benzylcarbamoyl-(4-cyanophenylamino)methyl]-4-methoxyphenoxy]acetic acid, (E)- and/or (Z)-(RS)-[2-[benzylcarbamoyl-[4-(N-hydroxycarbamimidoyl)phenylamino]methyl]-4-methoxyphenoxy]acetic acid.

The starting material was prepared as follows:

61.1

A solution of 30 g of 2-hydroxy-5-methoxybenzaldehyde in 200 ml of acetone was admixed with 51.2 ml of allyl bromide and 81.75 g of $K_2CO_3$ and heated under reflux for 2 hours. The reaction mixture was subsequently filtered. The filtrate was concentrated under reduced pressure. The residue was taken up in $CH_2Cl_2$ and washed with $H_2O$. The organic phases were dried over $Na_2SO_4$, filtered and concentrated under reduced pressure. The residue was distilled under high vacuum. This gave 24.5 g (65%) of 2-allyloxy-5-methoxybenzaldehyde as a slightly green oil.

61.2

By the method of Example 59.1, the aldehyde obtained above, 4-aminobenzonitrile and benzylisonitrile gave (RS)-2-(2-allyloxy- 5-methoxyphenyl)-N-benzyl-2-(4-cyanophenylamino)acetamide in a yield of 35%. ISP-MS: 428.3 [M+H], 450.1 [M+Na].

61.3

A solution of 4.6 9 of the nitrile obtained above in 140 ml of THF was admixed with 249 mg of tetrakis (triphenylphosphine)palladium(0). The mixture was stirred at RT for 10 min, and 626 mg of $NaBH_4$ were then added a little at a time. The mixture was stirred at RT for 2 hours and subsequently concentrated under reduced pressure. The residue was taken up in EtOAc and washed with $H_2O$. The organic phase was dried over $Na_2SO_4$, filtered and concentrated under reduced pressure. The residue was dissolved in $CH_2Cl_2$/EtOAc 9:1 and decolorized with activated carbon. The product was subsequently crystallized from $Et_2O/CH_2Cl_2$. This gave 3.22 g (77%) of (RS)-N-benzyl-2-(4-cyanophenylamino)-2-(2-hydroxy-5-methoxyphenyl) acetamide as a slightly brown crystalline solid. ISN-MS: 386.1 [M–H].

EXAMPLE 62

By the method of Example 60, (RS)-N-benzyl-2-(4-cyanophenylamino)-2-(2-hydroxy-3,5-dimethylphenyl)-acetamide and ethyl bromoacetate gave ethyl (RS)-[2-[benzylcarbamoyl-(4-cyanophenylamino)methyl]-4,6-dimethylphenoxy]acetate, which gave (E)- and/or (Z)-(RS)-[2-[benzylcarbamoyl-[4-(N-hydroxycarbamimidoyl) phenylamino]methyl]-4,6-dimethylphenoxy]acetic acid.

The starting material was prepared by the method of Example 16 from 3,5-dimethyl-2-hydroxybenzaldehyde (G. Casiraghi et al., *J. Chem. Soc.*, 1862 (1980)] 4-aminobenzonitrile and benzylisonitrile.

EXAMPLE 63

63.1

A solution of 1.04 g of the nitrile obtained in Example 59.2, 0.35 ml of methyl (S)-lactate and 785 mg of triphenylphosphine in 75 ml of THF was admixed with 0.475 ml of diethyl azodicarboxylate and stirred at RT for 4 hours. The THF was subsequently distilled off under reduced pressure. The residue was taken up in EtOAc and washed with saturated NaCl solution. The organic phase was dried over $MgSO_4$, filtered and concentrated under reduced pressure. The residue was purified by silica gel chromatography ($CH_2Cl_2$/EtOAc 9:1). This gave 1.145 g (88%) of a 1:1 mixture of ethyl (R)-2-[2-[(R)- and -[(S)-benzylcarbamoyl-(4-cyanophenylamino)methyl]-4,5-dimethoxyphenoxy] propionate as a yellow foam. ISP-MS: 518.2 [M+H], 540.3 [M+Na].

63.2

By the method of Example 36.2, the ester prepared above gave, after chromatographic separation over silica gel, the two diastereomers (R)-2-[2-[(R)-benzylcarbamoyl-(4-cyanophenylamino)methyl]-4,5-dimethoxyphenoxy] propionic acid and (R)-2-(2-[(S)-benzylcarbamoyl-(4-cyanophenylamino)methyl]-4,5-dimethoxyphenoxy] propionic acid in a yield of 49%, both as light-yellow resins. ISP-MS: 490.3 [M+H], 512.3 [M+Na].

63.3

By the method of Example 36.3, the first of the diastereomers obtained above gave
  a) (E)- and/or (Z)-(R)-2-[2-[(R)-benzylcarbamoyl-[4-(N-hydroxycarbamimidoyl)phenylamino]methyl]-4,5-dimethoxyphenoxy]propionic acid and the second of the diastereomers obtained above gave
  a) (E)- and/or (Z)-(R)-2-[2-[(S)-benzylcarbamoyl-[4-(N-hydroxycarbamimidoyl)phenylamino]methyl]-4,5-dimethoxyphenoxy]propionic acid, both as colorless powders. ISP-MS: 523.2 [M+H], 545.2 [M+Na], 567.2 [M+2Na].

63.4

By the method of Example 33, the respective diastereomeric amidoximes from Example 63.3 gave the amidines a) (R)-2-[2-[(R)-benzylcarbamoyl-(4-carbamimidoylphenylamino)methyl]-4,5-dimethoxyphenoxy]propionic acid acetate (1:1) and
b) (R)-2-[2-[(S)-benzylcarbamoyl-(4-carbamimidoylphenylamino)methyl1-4,5-dimethoxyphenoxy]propionic acid acetate (1:1), ISP-MS: 507.4 [M+H].

EXAMPLE 64

64.1

By the method of Examples 63.1–63.3, the material obtained in Example 59.2 and ethyl (R)-lactate gave, via the mixture of epimers of the corresponding nitrile ester, the two diastereomeric nitrile acids, which gave the respective epimers a) (E)- and/or (Z)-(S)-2-[2-[(R)-benzylcarbamoyl-[4-(N-hydroxycarbamimidoyl)phenylamino]methyl]-4,5-dimethoxyphenoxy]propionic acid and
b) (E)- and/or (Z)-(S)-2-[2-[(S)-benzylcarbamoyl-[4-(N-hydroxycarbamimidoyl)phenylamino]methyl]-4,5-dimethoxyphenoxy]propionic acid, both as colorless lyophilizates.

64.2

By the method of Example 33, the amidoximes obtained above gave the respective amidines a) (S)-2-[2-[(R)-benzylcarbamoyl-(4-carbamimidoylphenylamino)methyl]-4,5-dimethoxyphenoxy]propionic acid and
b) (S)-2-(2-[(S)-benzylcarbamoyl-(4-carbamimidoylphenylamino)methyl]-4,5-dimethoxyphenoxy]propionic acid, both as colorless lyophilizates. ISP-MS: 507.4 [M+H], 529.2 [M+Na].

EXAMPLE 65

By the method of Example 45, 65.a the product from Example 66.4 gave (RS)-3-{4-[benzylcarbamoyl-(4-carbamimidoylphenylamino)methyl]-2-methoxyphenoxy}benzoic acid in a yield of 44%. Colorless solid, ISP-MS: 525.2 [M+H], 65.b the product from Example 67.a gave (RS)-2-{4-[benzylcarbamoyl-(4-carbamimidoylphenylamino)methyl]-2-methoxyphenoxy}benzoic acid, ISP-MS: 525.2 [M+H], 65.c the product from Example 67.b gave (RS)-4-{4-[benzylcarbamoyl-(4-carbamimidoylphenylamino)methyl]-2-methoxyphenoxy}benzoic acid. Slightly brown solid. ISP-MS: 525.2 [M+H].

EXAMPLE 66

66.1

A solution of 3 g of vanillin, 11 g of ethyl 3-iodobenzoate and 2.9 g of Cu$_2$O in 5 ml of dimethylacetamide was heated at 165° C. for 24 hours. The mixture was allowed to cool to RT and filtered. The filtrate was concentrated under high vacuum. The residue was purified by silica gel chromatography (EtOAc/hexane 3:7). This gave 1.93 g (32%) of ethyl 3-(4-formyl-2-methoxyphenoxy)benzoate as a slightly brown oil.

66.2

By the method of Example 59.1, the aldehyde obtained above gave ethyl (RS)-3-{4-[benzylcarbamoyl-(4-cyanophenylamino)methyl]-2-methoxyphenoxy}benzoate in a yield of 58%. Colorless solid.

66.3

By the method of Example 36.2, the nitrile ester obtained above gave (RS)-3-{4-[benzylcarbamoyl-(4-cyanophenylamino)methyl]-2-methoxyphenoxy}benzoic acid in a yield of 51%. Colorless solid. ISN-MS: 506.2 [M–H].

66.4

By the method of Example 36.3, the nitrile acid obtained above gave (RS)-3-(4-{benzylcarbamoyl-[4-(N-hydroxycarbamimidoyl)phenylamino]methyl}-2-methoxyphenoxy)benzoic acid in a yield of 94%. Colorless solid. ISP-MS: 541.2 [M+H], 563.3 [M+Na].

EXAMPLE 67

By the method of Example 66

67.a and using methyl 2-iodobenzoate instead of ethyl 3-iodobenzoate, (RS)-2-(4-{benzylcarbamoyl-[4-(N-hydroxycarbamimidoyl)phenylamino]methyl}-2-methoxyphenoxy)benzoic acid was obtained via the corresponding intermediates 4-(2-carbomethoxy)phenoxy-3-methoxybenzaldehyde, methyl (RS)-2-[4-[benzylcarbamoyl-(4-cyanophenylamino)methyl]-2-methoxyphenoxy]benzoate and (RS)-2-{4-[benzylcarbamoyl-(4-cyanophenylamino)methyl]-2-methoxyphenoxy}benzoic acid, 67.b and using methyl 4-iodobenzoate instead of ethyl 3-iodobenzoate, (RS)-4-(4-{benzylcarbamoyl-[4-(N-hydroxycarbamimidoyl) phenylamino]methyl}-2-methoxyphenoxy)benzoic acid was obtained via the corresponding intermediates methyl 4-(4-formyl-2-methoxyphenoxy)benzoate, methyl (RS)-4-{4-[benzylcarbamoyl-( 4-cyano-phenylamino)methyl]-2-methoxyphenoxy}benzoate and (RS)-4-{4-[benzylcarbamoyl-(4-cyanophenylamino)methyl]-2-methoxyphenoxy}benzoic acid.

EXAMPLE 68

By the method of Examples 66.2–66.4, methyl 5-formyl-2,3-dimethoxybenzoate [F. Y. Wu, et al., *Food Chem.*, 25: 692 (1977)] gave, via the intermediate methyl (RS)-5-[benzylcarbamoyl-(4-cyanophenylamino)methyl]-2,3-dimethoxybenzoate, a) methyl (RS)-5-{benzylcarbamoyl-[4-(N-hydroxycarbamimidoyl)phenylamino]methyl}-2,3-dimethoxybenzoate and
b) methyl (RS)-5-[benzylcarbamoyl-(4-carbamimidoylphenylamino)methyl]-2,3-dimethoxybenzoate and
c) (RS)-5-[benzylcarbamoyl-(4-carbamimidoylphenylamino)methyl]-2,3-dimethoxybenzoic acid. Slightly brown solid.

EXAMPLE 69

69.1

By the method of Example 59.1, 6-bromoveratrumaldehyde, 4-aminobenzonitrile and benzylisonitrile gave (RS)-N-benzyl-2-(2-bromo-4,5-dimethoxyphenyl)-2-(4-cyanophenylamino)acetamide in a yield of 47%. Colorless solid.

69.2

A solution of 2.4 g of the nitrile obtained in Example 69.1 in 10 ml of dimethylacetamide was admixed with 0.41 ml of acrylic acid, 1.51 ml of triethylamine, 22 mg of palladium acetate and 122 mg of tri-o-tolylphosphine and heated at 120° C. for 2 hours. The reaction mixture was diluted with water, adjusted to pH 1 using 1N HCl and then extracted with EtOAc. The organic phase was concentrated under reduced pressure. The residue was dissolved in MeOH and filtered. The filtrate was concentrated under reduced pressure. The residue was stirred in Et$_2$O. The solid was filtered off and dried under high vacuum. This gave 1.71 g (73%) of (E)-(RS)-3-[2-[benzylcarbamoyl-(4-cyanophenylamino) methyl]-4,5-dimethoxyphenyl]acrylic acid as a beige solid.

69.3

A solution of 236 mg of the nitrile obtained above in 2 ml of EtOH and 3 ml of THF was admixed with 5 ml of 1N HCl and 106 mg of Pd/C 10% and hydrogenated for 2 hours. The reaction mixture was filtered. The filtrate was extracted with EtOAc. The organic phase was dried over MgSO$_4$ and concentrated under reduced pressure. The residue was purified by silica gel chromatography. This gave 44 mg (18%) of (RS)-3-[2-[benzylcarbamoyl-(4-cyanophenylamino) methyl]-4,5-dimethoxyphenyl]propionic acid as a slightly yellow solid.

69.4

By the method of Example 36.3, the nitrile obtained in Example 69.3 gave (E)- and/or (Z)-(RS)-3-[2-[benzylcarbamoyl-[4-(N-hydroxycarbamimidoyl) phenylamino]methyl]-4,5-dimethoxyphenyl]propionic acid in a yield of 26%. Beige lyophilizate.

69.5

Reduction by the method of Example 45 of the amidoxime obtained above gave (RS)-3-[2-[benzylcarbamoyl-(4-carbamimidoylphenylamino)methyl]-4,5-dimethoxyphenyl]propionic acid in a yield of 63%. White lyophilizate.

EXAMPLE 70

70.1

By the method of Example 16, 3-nitro-benzaldehyde, 4-aminobenzonitrile and benzylisonitrile gave (RS)-N-benzyl-2-(4-cyanophenylamino)-2-(3-nitrophenyl) acetamide in a yield of 11%. Light-yellow crystalline solid. ISP-MS: 387.2 [M+H], 409.3 [M+Na].

70.2

A solution of 1.4 g of the nitro compound obtained above in 80 ml of THF was admixed with 140 mg of Pd/C 10% and hydrogenated for 6 hours. The catalyst was filtered off and the filtrate was concentrated under reduced pressure. The residue was purified by silica gel chromatography (CH$_2$Cl$_2$/MeOH 19:1). This gave 1.15 g (89%) of (RS)-2-(3-aminophenyl)-N-benzyl-2-(4-cyanophenylamino)acetamide as a yellow foam. ISP-MS: 357.2 [M+H], 379.3 [M+Na].

70.3

By the method of Example 50.1, the amine obtained above was reacted with acetyl chloride to gave colorless (RS)-2-(3-acetylaminophenyl)-N-benzyl-2-(4-cyanophenylamino)acetamide in a yield of 99%. ISP-MS: 399.4 [M+H], 421.3 [M+Na], 437.3 [M+K].

70.4

By the method of Example 36.3 and starting from the above nitrile, (E)- and/or (Z)-(RS)-2-(3-acetylaminophenyl)-N-benzyl-2-[4-(N-hydroxycarbamimidoyl)phenylamino]acetamide was obtained in quantitative yield. Colorless solid.

70.5

By the method of Example 45, the amidoxime obtained according to Example 70.4 was reduced to (RS)-2-(3-acetylaminophenyl)-N-benzyl-2-(4-carbamimidoylphenylamino)acetamide acetate (1:1) in a yield of 65%. Colorless powder.

EXAMPLE 71

At 5–10° C., dry HCl gas was introduced into a solution of 386 mg of the nitrile from Example 70.1 in 20 ml of MeOH and 10 ml of CHCl$_3$ for 2 hours. The reaction solution was subsequently concentrated under reduced pressure. The residue was taken up in 30 ml of NH$_3$-saturated MeOH. The solution was allowed to stand at RT overnight and then heated at 40° C. for 4 hours and finally concentrated under reduced pressure. The residue was purified by silica gel chromatography. This gave 160 mg (35%) of (RS)-N-benzyl-2-(4-carbamimidoylphenylamino)-2-(3-nitrophenyl)acetamide acetate (1:1) as a yellow solid. ISP-MS: 404.4 [M+H].

EXAMPLE 72

A solution of 201 mg of 2,6-dimethoxyisonicotinaldehyde [I. Kompis et al., *Eur. J. Med. Chem.—Chim. Ther.*, 12: 531 (1977)] and 575 mg of 4-aminobenzamidine ditoluenesulphonate in 4.8 ml of THF/H$_2$O 9:1 was admixed with 0.15 ml of benzylisonitrile. The reaction mixture was stirred at RT for 6 hours and subsequently concentrated under reduced pressure. The residue was suspended in diethyl ether. The solid was filtered off and recrystallized from EtOH/water. This gave 2.02 g (28%) of (RS)-N-benzyl-2-(4-carbamimidoylphenylamino)-2-(2,6-dimethoxypyridin-4-yl)acetamide as a colorless crystalline solid.

EXAMPLE 73

By the method of Example 72, 73.a 4,6-dimethoxypicolinaldehyde [I. Kompis et al., *Eur. J. Med. Chem.—Chim. Ther.*, 12: 531 (1977)], 4-amidinobenzamidine ditoluenesulphonate and benzylisonitrile gave (RS)-N-benzyl-2-(4-carbamimidoylphenylamino)-2-(4,6-dimethoxypyridin-2-yl)acetamide in a yield of 41%, colorless crystalline solid, 73.b 4-benzyloxy-3,5-dimethoxybenzaldehyde, 4-amidinobenzamidine ditoluenesulphonate and benzylisonitrile gave (RS)-N-benzyl-2-(4-benzyloxy-3,5-dimethylphenyl)-2-(4-carbamimidoylphenylamino) acetamide in a yield of 23%. Colorless crystalline solid.

EXAMPLE 74

By the method of Example 1, 74.a 3-benzyloxy-5-propoxybenzaldehyde, 4-aminobenzamidine dihydrochloride and benzylisonitrile gave (RS)-N-benzyl-2-(3-benzyloxy-5-propoxyphenyl)-2-(4-carbamimidoylphenylamino)acetamide hydrochloride.

74.b 3,5-bis(benzyloxy)benzaldehyde, 4-aminobenzamidine dihydrochloride and benzylisonitrile gave (RS)-N-benzyl-2-(3,5-bis-benzyloxyphenyl)-2-(4-carbamimidoylphenylamino)acetamide hydrochloride.

EXAMPLE 75

75.a

By the method of Example 59.1, 2,6-diethoxypyridine-4-carbaldehyde [I. Kompis et al., *Eur. J. Med. Chem.—Chim. Ther.*, 12: 531 (1977)], 4-aminobenzonitrile and benzylisonitrile gave (RS)-N-benzyl-2-(4-cyanophenylamino)-2-(2,6-diethoxypyridin-4-yl)acetamide.

75.b

By the method of Example 71, the product from Example 75.a gave (RS)-N-benzyl-2-(4-carbamimidoylphenylamino)-2-(2,6-diethoxypyridin-4-yl)acetamide hydrochloride.

EXAMPLE 76

76.1

A solution of 5 g of 2-hydroxy-4-nitrobenzonitrile [W. Borsche, *Ann. Chem.*, 390: 1 (1912)] in 80.5 ml of isopropanol was admixed with 1 g of Pd/C 10% and hydrogenated for 1.5 hours. The mixture was subsequently filtered off from the catalyst and the filtrate was concentrated. This gave 3.3 g (80%) of 4-amino-2-hydroxybenzonitrile.

76.2

By the method of Example 59.1, the nitrile from Example 76.1, 4-benzyloxy-3-ethoxybenzaldehyde and benzylisonitrile gave (RS)-N-benzyl-2-(4-benzyloxy-3-ethoxyphenyl)-2-(4-cyano-3-hydroxyphenylamino)-acetamide.

76.3

By the method of Example 13, the material obtained above gave (RS)-N-benzyl-2-(4-benzyloxy-3-ethoxyphenyl)-2-[3-hydroxy-4-(N-hydroxycarbamimidoyl) phenylamino]acetamide.

76.4

Reduction of the amidoxime from Example 76.3 by the method of Example 45 gave (RS)-N-benzyl-2-(4-benzyloxy-3-ethoxyphenyl)-2-(4-carbamimidoyl-3-hydroxyphenylamino)acetamide.

EXAMPLE 77

77.1

A solution of 14.35 g of 4-benzyloxy-5-methoxy-2-nitrobenzaldehyde in 175 ml of MeOH was admixed with 5.9 g of 4-aminobenzonitrile and stirred at RT for 1 hour. This gave a suspension which was admixed with 6.1 ml of benzylisonitrile and then cooled to 0° C. 19 ml of boron trifluoride ethyl etherate were subsequently added dropwise over a period of 15 min. The mixture was allowed to warm to RT and stirred for another 1.5 hours, giving a solution. This was concentrated under reduced pressure. The residue was dissolved in 330 ml of MeOH and 3.6 ml of $H_2O$. The reaction mixture was stirred at RT overnight, and a solid crystallized out. This was filtered off, washed with MeOH/$H_2O$ 8:2 and $Et_2O$ and dried under high vacuum. This gave 16.3 g (61%) of methyl (RS)-(4-benzyloxy-5-methoxy-2-nitrophenyl)-(4-cyanophenylamino)acetate as a slightly yellow crystalline solid.

77.2

A solution of 4.47 g of the nitrile obtained above in 100 ml of THF was admixed with 1.79 g of Pt/C 5% and hydrogenated for 1 day. The mixture was subsequently filtered off from the catalyst and concentrated under reduced pressure. The residue was purified by silica gel chromatography (toluene/EtOAc 2:1). This gave 2.24 g (50%) of methyl (RS)-(2-amino-4-benzyloxy-5-methoxyphenyl)-(4-cyanophenylamino)acetate as a slightly orange solid. ISP-MS: 440.3 [M+Na].

77.3

A solution of 1.79 g of the material obtained in Example 77.2 in 60 ml of $CH_2Cl_2$ was admixed with 4 ml of DMF and 2.21 ml of diisopropylethylamine and cooled to 0° C. 1.21 ml of phenylsulphonyl chloride in 10 ml of $CH_2Cl_2$ were then added dropwise over a period of 20 min. The mixture was then allowed to warm to RT over a period of 3 hours. The reaction solution was concentrated under reduced pressure. The residue was purified by silica gel chromatography (toluene/EtOAc 4:1). This gave 635 mg (21%) of methyl (RS)-[4-benzyloxy-2-(bisphenylsulphonylamino)-5-methoxyphenyl]-(4-cyanopheny]amino)acetate as a slightly brown solid. ISP-MS: 698.2 [M+H], 720.2 [M+Na].

77.4

By the method of Example 25, 795 mg of the nitrile obtained in Example 77.3 gave (RS)-[4-benzyloxy-2-(bisphenylsulphonylamino)-5-methoxyphenyl]-(4-cyanophenylamino)acetic acid. This was reacted by the method of Example 36.1, but using methyl (S)-phenylglycinate instead of methyl L-alaninate hydrochloride, to gave a 1:1 mixture of methyl (S)-[(R)- and -[(S)-2-[4-benzyloxy-2-(bisphenylsulphonylamino)-5-methoxyphenyl]-2-(4-cyanophenylamino)acetylamino] phenyl acetate. The latter in turn was dissolved in 20 ml of THF and admixed with 11 ml of 1N LiOH solution. The reaction mixture was heated at 60° C. for 6 hours and at 40° C. overnight. The THF was subsequently distilled off under reduced pressure. The aqueous solution that remained was diluted with 2% strength citric acid and extracted with EtOAc. The organic phase was washed with saturated NaCl solution, dried over $MgSO_4$, filtered off and concentrated under reduced pressure. The residue was dissolved in 25 ml of EtOH and mixed with 3.07 ml of triethylamine and 794 mg of hydroxylamine hydrochloride. The reaction solution was heated under reflux overnight and then concentrated under reduced pressure. The residue was purified by two-fold silica gel chromatography (EtOAc/acetone/$H_2O$/HOAc 6:2:1:1). This gave 256 mg (29%) of a 1:1 mixture of (S)-[(R)- and -[(S)-2-(2-phenylsulphonylamino-4-benzyloxy-5-methoxyphenyl)-2-[4-[(E)- and/or -[(Z)-N-hydroxycarbamimidoyl)phenylamino]acetylamino] phenylacetic acid as a slightly brown lyophilizate. ISP-MS: 710:1 [M+H], 732.2 [M+Na].

77.5

A solution of 190 mg of the amidoxime obtained above in 8 ml of EtOH and 1 ml of HOAc was admixed with a spatula tip of Raney nickel and hydrogenated overnight. The catalyst was filtered off and the filtrate was concentrated under reduced pressure. The residue was purified by silica gel chromatography. This gave the two epimers a) (S)-[(R)-2-(2-phenylsulphonylamino-4-benzyloxy-5-methoxyphenyl)-2-(4-carbamimidoylphenylamino) acetylamino]phenylacetic acid acetate (1:1) and b) (S)-[(S)-2-(2-phenylsulphonylamino-4-benzyloxy-5-methoxyphenyl)-2-(4-carbamimidoylphenylamino) acetylamino]phenylacetic acid acetate (1:1), both as colorless lyophilisates. ISP-MS: 694.2 [M+H].

EXAMPLE 78

78.1

5.9 g of 4-aminobenzonitrile were added to a solution of 14.3 g of 4-benzyloxy-5-methoxy-2-nitrobenzaldehyde in 350 ml of allyl alcohol. The yellow suspension was stirred at RT for 1.5 hours. 6.1 ml of benzylisonitrile were then added and the reaction mixture was cooled to 0° C. 19 ml of boron trifluoride etherate were added dropwise. The suspension was allowed to warm to RT. The solid was subsequently filtered off, washed with diethyl ether and suspended in 200 ml of allyl alcohol and 18 ml of water. The reaction mixture was stirred at RT overnight and then concentrated under reduced pressure. The residue was purified by silica gel chromatography (toluene/acetone 9:1). The product was recrystallized from THF/hexane. This gave 7.35 g (45%) of allyl (RS)-(4-benzyloxy-5-methoxy-3-nitrophenyl)-(4-cyanophenylamino)acetate as light-yellow crystals. ISN-MS: 472.1 [M−H].

78.2

2 g of dimedone(5,5-dimethyl-1,3-cyclo-hexanedione) and 1.8 g of tetrakis(triphenyl-phosphine)palladium were added to a solution of 7.1 g of the nitrile obtained according to Example 78.1 in 75 ml of THF. The reaction mixture was stirred at RT for 30 min and subsequently admixed with activated carbon, stirred at RT for another 30 min and then filtered. The filtrate was concentrated under reduced pressure. The residue was purified by two-fold silica gel chromatography (first CH$_2$Cl$_2$/MeOH 19:1, then EtOAc). This gave 2.25 g (35%) of (RS)-(4-benzyloxy-5-methoxy-2-nitrophenyl)-(4-cyanophenylamino)acetic acid as yellow solid. ISP-MS: 434.3 [M+H].

78.3

By the method of Example 36.1, using 1.67 g of the nitrile obtained according to Example 78.2 and methyl (S)-phenylglycinate instead of methyl L-alaninate hydrochloride, 1.03 g (46%) of a 1:1 mixture of methyl (S)-[(R)- and -[(S)-2-(4-benzyloxy-5-methoxy-2-nitrophenyl)-2-(4-cyanophenylamino)acetylamino]phenyl acetate were obtained as a red-brown solid foam. ISP-MS: 581.1 [M+H], 603.0 [M+Na].

78.4

By the method of Example 27, 636 mg of the nitrocompound from Example 78.3 gave 235 mg (40%) of a 1:1 mixture of methyl (S)-[(R)- and -[(S)-2-(2-amino-4-benzyloxy-5-methoxyphenyl)-2-(4-cyanophenylamino)-acetylamino]phenylacetate as a colorless crystalline solid. ISN-MS: 549.1 [M+H].

78.5

By the method of Example 50.1, 100 mg of the above aminonitrile and phenylacetyl chloride gave 118 mg (98%) of a 1:1 mixture of methyl (S)-[(R)- and -[(S)-2-(4-benzyloxy-5-methoxy-2-phenylacetylaminophenyl)-2-(4-cyanophenylamino)acetylamino]phenylacetate as a colorless solid foam. ISN-MS: 667.2 [M−H].

78.6

By the method of Example 36.2, 108 mg of the nitrile obtained in Example 78.5 gave 104 mg (98%) of a 1:1 mixture of (S)-[(R)- and -[(S)-2-(4-benzyloxy-5-methoxy-2-phenylacetylaminophenyl)-2-( 4-cyanophenylamino) acetylamino]phenylacetic acid as a solid, slightly yellow foam. ISP-MS: 655.1 [M+H].

78.7

By the method of Example 36.3,180 mg of the above nitrile gave 133 mg (70%) of a 1:1 mixture of (S)-[(R)- and -[(S)-2-(4-benzyloxy-5-methoxy-2-phenylacetylaminophenyl)-2-[4-[(E)- and/or -[(Z)-N-hydroxycarbamimidoyl]phenylamino]acetylamino] phenylacetic acid as a colorless powder. ISP-MS: 688.2 [M+H], 710.1 [M+Na].

78.8

The epimer mixture from Example 78.7 gave, by the method of Example 33 and after chromatographic separation of the product over silica gel, the two epimers a) (S)-[(R)-2-(2-phenylacetylamino-4-benzyloxy-5-methoxyphenyl)-2-(4-carbamimidoylphenylamino)acetylamino]phenylacetic acid acetate (1:1) and b) (S)-[(S)-2-(2-phenylacetylamino-4-benzyloxy-5-methoxyphenyl)-2-(4-carbamimidoylphenylamino)acetylamino]phenylacetic acid acetate (1:1), both as colorless powder. ISP-MS: 672.3 [M+H].

EXAMPLE 79

By the methods of Examples 78.5–78.8, but using acetic anhydride instead of phenylacetyl chloride, the product from Example 78.4 gave, after chromatographic separation, the two epimers (S)-[(R)-2-(2-acetylamino-4-benzyloxy-5-methoxyphenyl)-2-(4-cyanophenylamino)-acetylamino] phenylacetic acid and (S)-[(S)-2-(2-acetylamino-4-benzyloxy-5-methoxyphenyl)-2-(4-cyanophenylamino) acetylamino]phenylacetic acid. Via the respective amidoximes, these were reacted to gave the two epimers a) (S)-[(R)-2-(2-acetylamino-4-benzyloxy-5-methoxyphenyl)-2-( 4-carbamimidoylphenylamino) acetylamino]-phenylacetic acid acetate and b) (S)-[(S)-2-(2-acetylamino-4-benzyloxy-5-methoxyphenyl)-2-(4-carbamimidoylphenylamino) acetylamino]-phenylacetic acid acetate. ISP-MS: 596.2 [M+H].

EXAMPLE 80

A solution of 0.024 ml of 4-fluorobenzoyl chloride in 1.0 ml of THF and 0.5 ml of DMF was admixed with 0.038 ml of N,N-diisopropylethylamine and stirred at RT for 5 minutes. 100 mg of the product from Example 5.g were then added. The reaction mixture was stirred at RT overnight. Another 0.024 ml of 4-fluorobenzoyl chloride and 0.1 ml of N,N-diisopropylethylamine were added, and the mixture was stirred at RT for 3 hours. The reaction mixture was concentrated under reduced pressure. The residue was taken up in saturated NaHCO$_3$ solution and extracted with EtOAc. The organic phase was dried over MgSO$_4$, filtered and concentrated under reduced pressure. The residue was purified by silica gel chromatography (hexane/EtOAc 2:1). The product was crystallized from Et$_2$O. This gave 20 mg (17%) of (RS)-N-[amino-(4-{[benzylcarbamoyl-(4-benzyloxy-3-ethoxyphenyl)methyl]amino}phenyl)methylene]-4-fluorobenzamide as a crystalline solid. ISP-MS: 631.2 [M+H].

EXAMPLE 81

By the method of Example 80, the product from Example 5.g and 2-benzyloxymethylbenzoyl chloride gave (RS)-2-{[amino-(4-{[benzylcarbamoyl-(4-benzyloxy-3-ethoxyphenyl)methyl]amino}phenyl)methylene] carbamoyl}-benzyl benzoate in a yield of 21%. Yellow crystalline solid. ISP-MS: 747.4 [M+H].

EXAMPLE 82

By the method of Example 80, the product from Example 5.g and p-nitrophenyl 2,2,2-trichloroethyl-carbonate gave 2,2,2-trichloroethyl (RS)-[amino-(4-{[benzylcarbamoyl-(4-benzyloxy-3-ethoxyphenyl)-methyl]amino}phenyl) methylene]carbamate in a yield of 60%. Crystalline solid. ISP-MS: 683.1 [M+H].

EXAMPLE 83

By the method of Example 80, the product from Example 5.g and methyl 4-nitrophenylcarbonate gave methyl (RS)-[amino-(4-{[benzylcarbamoyl-(4-benzyloxy-3-ethoxyphenyl)methyl]amino}phenyl)methylene]carbamate in a yield of 91% as a solid. ISP-MS: 567.3 [M+H].

A compound of the formula I, a hydrate, a solvate or a salt thereof can be used as active ingredient for preparing pharmaceutical preparations like those below.

| Example A | |
| --- | --- |
| | per tablet |
| Active ingredient | 200 mg |
| Microcrystalline cellulose | 155 mg |
| Maize starch | 25 mg |
| Talc | 25 mg |
| Hydroxypropylmethylcellulose | 20 mg |
| | 425 mg |

-continued

Example B

|  | per capsule |
| --- | --- |
| Active ingredient | 100.0 mg |
| Maize starch | 20.0 mg |
| Lactose | 95.0 mg |
| Talc | 4.5 mg |
| Magnesium stearate | 0.5 mg |
|  | 220.0 mg |

The subject invention has been described in terms of its preferred embodiments. Upon reading the specification, various alternative embodiments will become obvious to the skilled artisan. These variations are to be considered within the scope and spirit of the subject invention which is only to be limited by the claims that follow and their equivalents.

What is claimed is:

1. A compound of the formula:

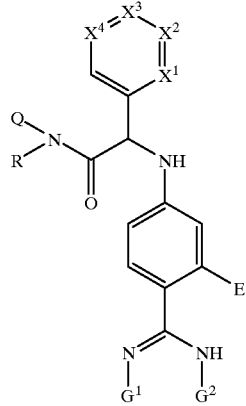

I wherein

| E | is hydrogen or OH; |
| --- | --- |
| Q | is hydrogen or alkyl; |
| R | is aryl, cycloalkyl, or alkyl substituted by $R^1$, $R^2$ and $R^3$; |
| $R^1$ | is hydrogen, COOH, COO-alkyl, or aryl; |
| $R^2$ | is hydrogen, aryl, cycloalkyl, or heteroaryl; |
| $R^3$ | is hydrogen, aryl, or (in a position different from the α-position to the nitrogen atom to which the alkyl group R is attached) OH, alkoxy, amino, or protected amino; or |

N(Q,R) is COOH— or COO-alkyl-substituted pyrrolidino, piperidino, or 1,2,3,4-tetrahydroisoquinolin-3-yl;

three of $X^1$ to $X^4$, independent of one another, are a group $C(R^a)$, $C(R^b)$ or $C(R^c)$, and the fourth is a group $C(R^d)$ or N, $R^a$ to $R^d$ independent of one another are H, OH, $NO_2$, dialkylamino, halogen, alkyl, alkoxy, aryloxy, aralkyloxy, heteroarylalkyloxy, heterocyclylalkyloxy, COOH, COO-alkyl, $NHSO_2$-alkyl, $NHSO_2$-aryl, NHCO-alkyl, NHCO-aryl, NHCOO-alkyl, NHCO-alkyl-$NH_2$, NHCO-alkyl-NH—G, aralkyl-CONH, alkyl-O-alkyl-CONH, aryl-O-alkyl-CONH, alkyl-COOH, alkyl-COO-alkyl, O-alkyl-COOH, or O-alkyl-COO-alkyl, or two adjacent groups $R^a$ to $R^d$ together are alkylenedioxy, where not more than three of the groups $R^a$ to $R^d$ shall have the same meaning and $X^1$ shall not be CCOOH or CCOO-alkyl;

one of $G^1$ and $G^2$ is hydrogen and the other is hydrogen, alkyl, OH, alkoxy, aroyl, alkanoyl-$OCH_2$, aroyl-$OCH_2$ or a group COO—$R^g$ or OCO—$R^g$, where $R^g$ is alkyl or alkyl substituted by halogen, OH, alkoxy, COOH or COO-alkyl; and its hydrates or solvates, and physiologically acceptable salts thereof.

2. The compound according to claim 1, wherein

E, $G^2$ and Q are hydrogen;

R is alkyl, aryl, aralkyl, benzhydryl, cycloalkylalkyl, or heteroarylalkyl;

$G^1$ is hydrogen, OH, or COO-alkyl;

$X^1$ to $X^4$ are a group $C(R^a)$ to $C(R^d)$ and $R^a$ to $R^d$ independent of one another are H, OH, $NO_2$, dialkylamino, halogen, alkyl, alkoxy, aryloxy, aralkyloxy, heteroarylalkyloxy, heterocyclylalkyloxy, COO-alkyl, $NHSO_2$-alkyl, or $NHSO_2$-aryl, where not more than three of $R^a$ to $R^d$ have the same meaning; and $X^1$ is not COO-alkyl.

3. The compound according to claim 2, wherein E, $G^1$, $G^2$ and Q are hydrogen.

4. The compound according to claim 1, wherein R is alkyl which is substituted by $R^1$, $R^2$ and $R^3$, and $R^1$ is aryl or COOH, $R^2$ is hydrogen or aryl, and $R^3$ is hydrogen.

5. The compound according to claim 4, wherein R is methyl or ethyl, which is substituted by $R^1$, $R^2$ and $R^3$, and $R^1$ is phenyl or COOH, $R^2$ is hydrogen or phenyl, and $R^3$ is hydrogen.

6. The compound according to claim 1, wherein $X^1$ to $X^4$ are each a group $C(R^a)$ to $C(R^d)$; $R^a$ is H, aralkyloxy, $NHSO_2$-aryl, $NHSO_2$-alkyl, aralkyl-CONH, or O-alkyl-COOH; $R^b$ is H or alkoxy; $R^c$ is H, alkoxy or aralkyloxy; and $R^d$ is H or alkoxy.

7. The compound according to claim 6, wherein $X^1$ to $X^4$ are each a group $C(R^a)$ to $C(R^d)$; $R^a$ is H, carboxybenzyloxy; phenylsulphonylamino; methylsulphonylamino, phenylacetylamino, or carboxymethoxy; $R^b$ is H, methoxy, or ethoxy; $R^c$ is H, methoxy; or benzyloxy; and $R^d$ is H or methoxy.

8. The compound according to claim 1 which has the formula:

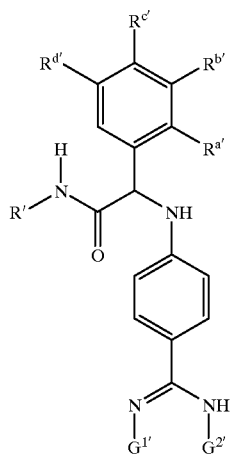

Ia wherein

| R' | is CH₂C₆H₅, CH(C₆H₅)COOH or C(C₆H₅)₂COOH; |
|---|---|
| Rᵃ' | H, carboxybenzyloxy; phenylsulphonylamino; methylsulphonyl-amino, phenylacetylamino, or carboxymethoxy; |
| Rᵇ' | is H, methoxy, or ethoxy; |
| Rᶜ' | is H, methoxy; or benzyloxy; |
| Rᵈ' | is H or methoxy; and | one of $G^{1'}$ and $G^{2'}$ is H and the other is H, OH, or COOCH₃; and
its hydrate or solvate, and a physiologically acceptable salt thereof.

9. The compound according to claim 8, wherein $R^{a'}$ is H, phenylsulphonylamino; or methylsulphonylamino.

10. The compound according to claim 9, wherein $R^{b'}$ is H or ethoxy.

11. The compound according to claim 10, wherein $G^{1'}$ is H or OH.

12. The compound according to claim 11, wherein $R^{c'}$ is benzyloxy.

13. The compound according to claim 12, wherein $R^{d'}$ is H.

14. The compound according to claim 13 which is (R,S)-N-benzyl-2-(4-benzyloxy-3-ethoxyphenyl)-2-(4-carbamimidoylphenylamino)acetamide.

15. The compound according to claim 13 which is (R,S)-N-benzyl-2-(4-benzyloxy-3-ethoxyphenyl)-2-[4-(N-hydroxycarbamimidoyl)phenylamino]acetamide.

16. The compound according to claim 12, wherein $R^{d'}$ is methoxy.

17. The compound according to claim 16 which is 2-(2-phenylsulphonylamino-4-benzyloxy-5-methoxyphenyl)-N-benzyl-2-[4-(N-hydroxycarbamimidoyl)phenylamino]acetamide.

18. The compound according to claim 16 which is N-benzyl-2-(4-benzyloxy-2-methanesulphonylamino-5-methoxyphenyl)-2-[4-(N-hydroxycarbamimidoyl)phenylamino]acetamide.

19. The compound according to claim 1 which is 2-(2-phenylsulphonylamino-4-benzyloxy-5-methoxyphenyl)-N-benzyl-2-(4-carbamimidoylphenylamino)acetamide.

20. The compound according to claim 1 which is (RS)-[2-(4-benzyloxy-3-methoxyphenyl)-2-(4-carbamimidoylphenylamino)acetylamino]diphenylacetic acid.

21. The compound according to claim 1 which is (RS)- and (SR)-3-[(RS)-2-(4-benzyloxy-3-methoxyphenyl)-2-(4-carbamimidoylphenylamino)acetylamino]-3-phenylpropionic acid.

22. The compound according to claim 1 which is (S)-[(R)-2-(4-benzyloxy-3-methoxyphenyl)-2-(4-carbamimidoylphenylamino)acetylamino]phenylacetic acid.

23. The compound according to claim 1 which is (S)-[(S)-2-(4-carbamimidoylphenylamino)-2-(3,5-dimethoxyphenyl)acetylamino]phenylacetic acid.

24. The compound according to claim 1 which is (RS)-3-[2-[benzylcarbamoyl-(4-carbamimidoylphenylamino)methyl]-4,5-dimethoxyphenoxymethyl]benzoic acid.

25. The compound according to claim 1 which is (RS)-[2-[benzylcarbamoyl-(4-carbamimidoylphenylamino)methyl]-4,5-dimethoxyphenoxy]acetic acid.

26. The compound according to claim 1 which is (S)-[(R)-2-(2-phenylsulphonylamino-4-benzyloxy-5-methoxyphenyl)-2-(4-carbamimidoylphenylamino)acetylamino]phenylacetic acid.

27. The compound according to claim 1 which is (S)-[(S)-2-(2-phenylsulphonylamino-4-benzyloxy-5-methoxyphenyl)-2-(4-carbamimidoylphenylamino)acetylamino]phenylacetic acid.

28. The compound according to claim 1 which is (S)-[(R)-2-(4-benzyloxy-5-methoxy-2-phenylacetylaminophenyl)-2-(4-carbamimidoylphenylamino)acetylaminophenylacetic acid.

29. The compound according to claim 1 which is (S)-[(S)-2-(4-benzyloxy-5-methoxy-2-phenylacetylaminophenyl)-2-(4-carbamimidoylphenylamino)acetylamino]phenylacetic acid.

30. A pharmaceutical composition, which comprises:
(a) an effective amount of the compound of formula:

I

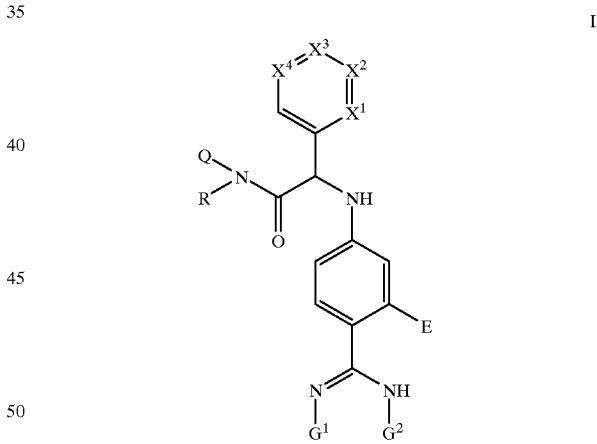

wherein

| E | is hydrogen or OH; |
|---|---|
| Q | is hydrogen or alkyl; |
| R | is aryl, cycloalkyl, or alkyl substituted by $R^1$, $R^2$ and $R^3$; |
| $R^1$ | is hydrogen, COOH, COO-alkyl, or aryl; |
| $R^2$ | is hydrogen, aryl, cycloalkyl, or heteroaryl; |
| $R^3$ | is hydrogen, aryl, or (in a position different from the α-position to the nitrogen atom to which the alkyl group R is attached) OH, alkoxy, amino, or protected amino; or |

N(Q,R) is COOH- or COO-alkyl-substituted pyrrolidino, piperidino, or 1,2,3,4-tetrahydroisoquinolin-3-yl;

three of $X^1$ to $X^4$, independent of one another, are a group $C(R^a)$, $C(R^b)$ or $C(R^c)$, and the fourth is a group $C(R^d)$ or N, $R^a$ to $R^d$ independent of one another are H, OH, $NO_2$, dialkylamino, halogen, alkyl, alkoxy, aryloxy, aralkyloxy, heteroarylalkyloxy, heterocyclylalkyloxy, COOH, COO-alkyl, $NHSO_2$-alkyl, $NHSO_2$-aryl, NHCO-alkyl, NHCO-aryl, NHCOO-alkyl, NHCO-alkyl-$NH_2$, NHCO-alkyl-NH—G, aralkyl-CONH, alkyl-O-alkyl-CONH, aryl-O-alkyl-CONH, alkyl-COOH, alkyl-COO-alkyl, O-alkyl-COOH, or O-alkyl-COO-alkyl, or two adjacent groups $R^a$ to $R^d$ together are alkylenedioxy, where not more than three of the groups $R^a$ to $R^d$ shall have the same meaning and $X^1$ shall not be CCOOH or CCOO-alkyl;

one of $G^1$ and $G^2$ is hydrogen and the other is hydrogen, alkyl, OH, alkoxy, aroyl, alkanoyl-$OCH_2$, aroyl-$OCH_2$ or a group COO—$R^g$ or OCO—$R^g$, where $R^g$ is alkyl or alkyl substituted by halogen, OH, alkoxy, COOH or COO-alkyl; and its hydrate or solvate, and a physiologically acceptable salt thereof; and (b) a pharmaceutically acceptable carrier.

31. A compound of the formula:

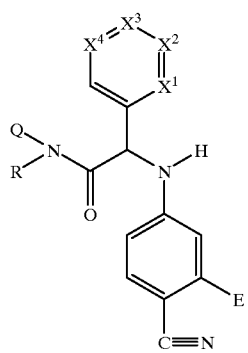

IV wherein

| | |
|---|---|
| E | is hydrogen or OH; |
| Q | is hydrogen or alkyl; |
| R | is aryl, cycloalkyl, or alkyl substituted by $R^1$, $R^2$ and $R^3$; |
| $R^1$ | is hydrogen, COOH, COO-alkyl, or aryl; |
| $R^2$ | is hydrogen, aryl, cycloalkyl, or heteroaryl; |
| $R^3$ | is hydrogen, aryl, or (in a position different from the α-position to the nitrogen atom to which the alkyl group R is attached) OH, alkoxy, amino, or protected amino; or N(Q,R) is COOH- or COO-alkyl-substituted pyrrolidino, piperidino, or 1,2,3,4-tetrahydroisoquinolin-3-yl; | three of $X^1$ to $X^4$, independent of one another, are a group $C(R^a)$, $C(R^b)$ or $C(R^c)$, and the fourth is a group $C(R^d)$ or N, $R^a$ to $R^d$ independent of one another are H, OH, $NO_2$, dialkylamino, halogen, alkyl, alkoxy, aryloxy, aralkyloxy, heteroarylalkyloxy, heterocyclylalkyloxy, COOH, COO-alkyl, $NHSO_2$-alkyl, $NHSO_2$-aryl, NHCO-alkyl, NHCO-aryl, NHCOO-alkyl, NHCO-alkyl-$NH_2$, NHCO-alkyl-NH—G, aralkyl-CONH, alkyl-O-alkyl-CONH, aryl-O-alkyl-CONH, alkyl-COOH, alkyl-COO-alkyl, O-alkyl-COOH, or O-alkyl-COO-alkyl, or two adjacent groups $R^a$ to $R^d$ together are alkylenedioxy, where not more than three of the groups $R^a$ to $R^d$ shall have the same meaning and $X^1$ shall not be CCOOH or CCOO-alkyl; and its hydrates or solvates, and physiologically acceptable salts thereof.

32. The compound according to claim 31, wherein
E and Q are hydrogen;
R is alkyl, aryl, aralkyl, benzhydryl, cycloalkylalkyl, or heteroarylalkyl;
$X^1$ to $X^4$ are a group $C(R^a)$ to $C(R^d)$ and
$R^a$ to $R^d$ independent of one another are H, OH, $NO_2$, dialkylamino, halogen, alkyl, alkoxy, aryloxy, aralkyloxy, heteroarylalkyloxy, heterocyclylalkyloxy, COO-alkyl, $NHSO_2$-alkyl, or $NHSO_2$-aryl, where not more than three of $R^a$ to $R^d$ have the same meaning; and $X^1$ is not COO-alkyl.

33. The compound according to claim 31, wherein E and Q are hydrogen.

34. The compound according to claim 31, wherein R is alkyl which is substituted by $R^1$, $R^2$ and $R^3$, and $R^1$ is aryl or COOH, $R^2$ is hydrogen or aryl, and $R^3$ is hydrogen.

35. The compound according to claim 34, wherein R is methyl or ethyl, which is substituted by $R^1$, $R^2$ and $R^3$, and $R^1$ is phenyl or COOH, $R^2$ is hydrogen or phenyl, and $R^3$ is hydrogen.

36. The compound according to claim 31, wherein $X^1$ to $X^4$ are each a group $C(R^a)$ to $C(R^d)$; $R^a$ is H, aralkyloxy, $NHSO_2$-aryl, $NHSO_2$-alkyl, aralkyl-CONH, or O-alkyl-COOH; $R^b$ is H or alkoxy; $R^c$ is H, alkoxy or aralkyloxy; and $R^d$ is H or alkoxy.

37. The compound according to claim 36, wherein $X^1$ to $X^4$ are each a group $C(R^a)$ to $C(R^d)$; $R^a$ is H, carboxybenzyloxy; phenylsulphonylamino; methylsulphonylamino, phenylacetylamino, or carboxymethoxy; $R^b$ is H, methoxy, or ethoxy; $R^c$ is H, methoxy; or benzyloxy; and $R^d$ is H or methoxy.

38. A compound of the formula:

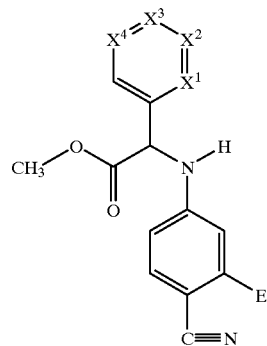

V wherein
E is hydrogen or OH;
three of $X^1$ to $X^4$, independent of one another, are a group $C(R^a)$, $C(R^b)$ or $C(R^c)$, and the fourth is a group $C(R^d)$ or N, $R^a$ to $R^d$ independent of one another are H, OH, $NO_2$, dialkylamino, halogen, alkyl, alkoxy, aryloxy, aralkyloxy, heteroarylalkyloxy, heterocyclylalkyloxy, COOH, COO-alkyl, $NHSO_2$-alkyl, $NHSO_2$-aryl, NHCO-alkyl, NHCO-aryl, NHCOO-alkyl, NHCO-alkyl-$NH_2$, NHCO-alkyl-NH—G, aralkyl-CONH, alkyl-O-alkyl-CONH, aryl-O-alkyl-CONH, alkyl-COOH, alkyl-COO-alkyl, O-alkyl-COOH, or O-alkyl-COO-alkyl, or two adjacent groups $R^a$ to $R^d$ together are alkylenedioxy, where not more than three of the groups $R^a$ to $R^d$ shall have the same meaning and $X^1$ shall not be CCOOH or CCOO-alkyl; and its hydrates or solvates, and physiologically acceptable salts thereof.

39. The compound according to claim 38, wherein $X^1$ to $X^4$ are each a group $C(R^a)$ to $C(R^d)$; $R^a$ is H, aralkyloxy, NHSO$_2$-aryl, NHSO$_2$-alkyl, aralkyl-CONH, or O-alkyl-COOH; $R^b$ is H or alkoxy; $R^c$ is H, alkoxy or aralkyloxy; and $R^d$ is H or alkoxy.

40. The compound according to claim 39, wherein $X^1$ to $X^4$ are each a group $C(R^a)$ to $C(R^d)$; $R^a$ is H, carboxybenzyloxy; phenylsulphonylamino; methylsulphonylamino, phenylacetylamino, or carboxymethoxy; $R^b$ is H, methoxy, or ethoxy; $R^c$ is H, methoxy; or benzyloxy; and $R^d$ is H or methoxy.

41. A compound of the formula:

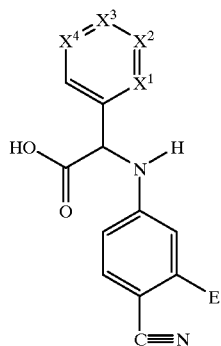

VI wherein

E is hydrogen or OH;

three of $X^1$ to $X^4$, independent of one another, are a group $C(R^a)$, $C(R^b)$ or $C(R^c)$, and the fourth is a group $C(R^d)$ or N, $R^a$ to $R^d$ independent of one another are H, OH, NO$_2$, dialkylamino, halogen, alkyl, alkoxy, aryloxy, aralkyloxy, heteroarylalkyloxy, heterocyclylalkyloxy, COOH, COO-alkyl, NHSO$_2$-alkyl, NHSO$_2$-aryl, NHCO-alkyl, NHCO-aryl, NHCOO-alkyl, NHCO-alkyl-NH$_2$, NHCO-alkyl-NH—G, aralkyl-CONH, alkyl-O-alkyl-CONH, aryl-O-alkyl-CONH, alkyl-COOH, alkyl-COO-alkyl, O-alkyl-COOH, or O-alkyl-COO-alkyl, or two adjacent groups $R^a$ to $R^d$ together are alkylenedioxy, where not more than three of the groups $R^a$ to $R^d$ shall have the same meaning and $X^1$ shall not be CCOOH or CCOO-alkyl; and its hydrates or solvates, and physiologically acceptable salts thereof.

42. The compound according to claim 41, wherein $X^1$ to $X^4$ are each a group $C(R^a)$ to $C(R^d)$; $R^a$ is H, aralkyloxy, NHSO$_2$-aryl, NHSO$_2$-alkyl, aralkyl-CONH, or O-alkyl-COOH; $R^b$ is H or alkoxy; $R^c$ is H, alkoxy or aralkyloxy; and $R^d$ is H or alkoxy.

43. The compound according to claim 42, wherein $X^1$ to $X^4$ are each a group $C(R^a)$ to $C(R^d)$; $R^a$ is H, carboxybenzyloxy; phenylsulphonylamino; methylsulphonylamino, phenylacetylamino, or carboxymethoxy; $R^b$ is H, methoxy, or ethoxy; $R^c$ is H, methoxy; or benzyloxy; and $R^d$ is H or methoxy.

44. A process for preparing a compound of the formula:

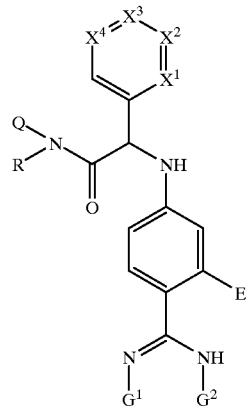

I wherein

| | |
|---|---|
| E | is hydrogen or OH; |
| Q | is hydrogen or alkyl; |
| R | is aryl, cycloalkyl, or alkyl substituted by $R^1$, $R^2$ and $R^3$; |
| $R^1$ | is hydrogen, COOH, COO-alkyl, or aryl; |
| $R^2$ | is hydrogen, aryl, cycloalkyl, or heteroaryl; |
| $R^3$ | is hydrogen, aryl, or (in a position different from the α-position to the nitrogen atom to which the alkyl group R is attached) OH, alkoxy, amino, or protected amino; or |

N(Q,R) is COOH- or COO-alkyl-substituted pyrrolidino, piperidino, or 1,2,3,4-tetrahydroisoquinolin-3-yl;

three of $X^1$ to $X^4$, independent of one another, are a group $C(R^a)$, $C(R^b)$ or $C(R^c)$, and the fourth is a group $C(R^d)$ or N, $R^a$ to $R^d$ independent of one another are H, OH, NO$_2$, dialkylamino, halogen, alkyl, alkoxy, aryloxy, aralkyloxy, heteroarylalkyloxy, heterocyclylalkyloxy, COOH, COO-alkyl, NHSO$_2$-alkyl, NHSO$_2$-aryl, NHCO-alkyl, NHCO-aryl, NHCOO-alkyl, NHCO-alkyl-NH$_2$, NHCO-alkyl-NH—G, aralkyl-CONH, alkyl-O-alkyl-CONH, aryl-O-alkyl-CONH, alkyl-COOH, alkyl-COO-alkyl, O-alkyl-COOH, or O-alkyl-COO-alkyl, or two adjacent groups $R^a$ to $R^d$ together are alkylenedioxy, where not more than three of the groups $R^a$ to $R^d$ shall have the same meaning and $X^1$ shall not be CCOOH or CCOO-alkyl;

one of $G^1$ and $G^2$ is hydrogen and the other is hydrogen, alkyl, OH, alkoxy, aroyl, alkanoyl-OCH$_2$, aroyl-OCH$_2$ or a group COO—$R^g$ or OCO—$R^g$, where $R^g$ is alkyl or alkyl substituted by halogen, OH, alkoxy, COOH or COO-alkyl;

its hydrates or solvates, and physiologically acceptable salts thereof;

which comprises:
(a) (i) reacting an aldehyde of the formula:

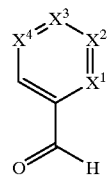

II with an isonitrile of the formula R¹NC and a 4-aminobenzamidine of the formula:

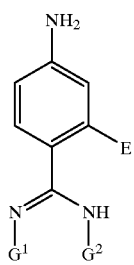

III or (ii) converting the cyano group contained in a nitrile of the formula:

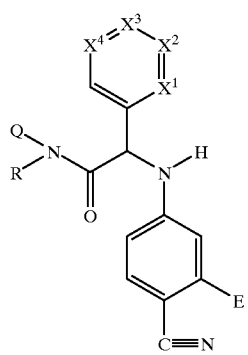

IV into an amidino group C(N—G¹)NH—G²;
(b) in the case of a compound of formula I having a functionally derivatized group, then functionally derivatizing a reactive group of the compound produced in step (a) to yield a compound of formula I having such functionally derivatized group; and
(c) in the case of a compound of formula I being a hydrate or solvate, or a physiologically acceptable salt thereof, then hydrating, solvating, or salinating the compound produced in step (a) or (b) to yield the hydrate or solvate, or physiologically acceptable salt thereof, of the compound of formula I.

45. A method of treating or preventing thromboses, apoplexy, cardiac infarction, inflammation and arteriosclerosis, or tumors influenced by the coagulation factors Xa, IXa, or thrombin, which comprises administering to a subject in need of such treatment or prevention an effective amount of the compound of formula:

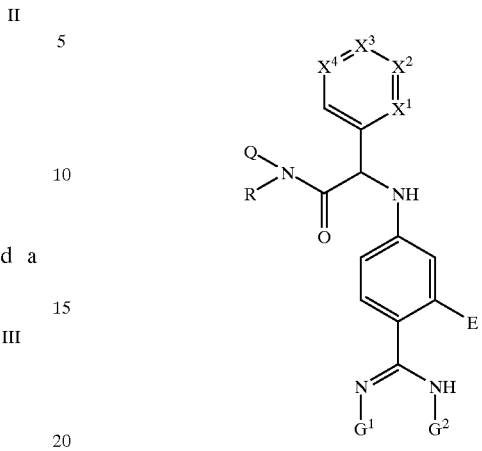

I wherein

| | |
|---|---|
| E | is hydrogen or OH; |
| Q | is hydrogen or alkyl; |
| R | is aryl, cycloalkyl, or alkyl substituted by $R^1$, $R^2$ and $R^3$; |
| $R^1$ | is hydrogen, COOH, COO-alkyl, or aryl; |
| $R^2$ | is hydrogen, aryl, cycloalkyl, or heteroaryl; |
| $R^3$ | is hydrogen, aryl, or (in a position different from the α-position to the nitrogen atom to which the alkyl group R is attached) OH, alkoxy, amino, or protected amino; or |

N(Q,R) is COOH- or COO-alkyl-substituted pyrrolidino, piperidino, or 1,2,3,4-tetrahydroisoquinolin-3-yl;

three of $X^1$ to $X^4$, independent of one another, are a group $C(R^a)$, $C(R^b)$ or $C(R^c)$, and the fourth is a group $C(R^d)$ or N, $R^a$ to $R^d$ independent of one another are H, OH, $NO_2$, dialkylamino, halogen, alkyl, alkoxy, aryloxy, aralkyloxy, heteroarylalkyloxy, heterocyclylalkyloxy, COOH, COO-alkyl, $NHSO_2$-alkyl, $NHSO_2$-aryl, NHCO-alkyl, NHCO-aryl, NHCOO-alkyl, NHCO-alkyl-$NH_2$, NHCO-alkyl-NH—G, aralkyl-CONH, alkyl-O-alkyl-CONH, aryl-O-alkyl-CONH, alkyl-COOH, alkyl-COO-alkyl, O-alkyl-COOH, or O-alkyl-COO-alkyl, or two adjacent groups $R^a$ to $R^d$ together are alkylenedioxy, where not more than three of the groups $R^a$ to $R^d$ shall have the same meaning and $X^1$ shall not be CCOOH or CCOO-alkyl;

one of $G^1$ and $G^2$ is hydrogen and the other is hydrogen, alkyl, OH, alkoxy, aroyl, alkanoyl-$OCH_2$, aroyl-$OCH_2$ or a group COO—$R^g$ or OCO—$R^g$, where $R^g$ is alkyl or alkyl substituted by halogen, OH, alkoxy, COOH or COO-alkyl; and its hydrates or solvates, and physiologically acceptable salts thereof.

* * * * *